United States Patent
Mahajan et al.

(10) Patent No.: US 10,336,734 B2
(45) Date of Patent: *Jul. 2, 2019

(54) INHIBITORS OF ACK1/TNK2 TYROSINE KINASE

(71) Applicant: H. LEE MOFFITT CANCER CENTER AND RESEARCH INSTITUTE, INC., Tampa, FL (US)

(72) Inventors: Nupam P. Mahajan, Tampa, FL (US); Kiran N. Mahajan, Tampa, FL (US); Nicholas J. Lawrence, Tampa, FL (US); Harshani R. Lawrence, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/748,214

(22) PCT Filed: Aug. 2, 2016

(86) PCT No.: PCT/US2016/045096
§ 371 (c)(1),
(2) Date: Jan. 29, 2018

(87) PCT Pub. No.: WO2017/023899
PCT Pub. Date: Feb. 9, 2017

(65) Prior Publication Data
US 2018/0215738 A1    Aug. 2, 2018

Related U.S. Application Data

(60) Provisional application No. 62/200,084, filed on Aug. 2, 2015, provisional application No. 62/299,178, filed on Feb. 24, 2016.

(51) Int. Cl.
| | | |
|---|---|---|
| A61K 31/506 | (2006.01) | |
| C07D 405/12 | (2006.01) | |
| C07D 403/12 | (2006.01) | |
| C07D 405/14 | (2006.01) | |
| C07D 401/12 | (2006.01) | |
| C07D 239/48 | (2006.01) | |
| A61P 35/00 | (2006.01) | |

(52) U.S. Cl.
CPC ............ *C07D 405/12* (2013.01); *A61P 35/00* (2018.01); *C07D 239/48* (2013.01); *C07D 401/12* (2013.01); *C07D 403/12* (2013.01); *C07D 405/14* (2013.01)

(58) Field of Classification Search
CPC .. C07D 405/12; C07D 239/48; C07D 403/12; A61K 31/506
See application file for complete search history.

(56) References Cited

U.S. PATENT DOCUMENTS

| | | |
|---|---|---|
| 4,559,157 A | 12/1985 | Smith |
| 4,608,392 A | 8/1986 | Jacquet et al. |
| 4,820,508 A | 4/1989 | Wortzman |
| 4,938,949 A | 7/1990 | Borch et al. |
| 4,992,478 A | 2/1991 | Geria |
| 5,167,649 A | 12/1992 | Zook |
| 6,960,648 B2 | 11/2005 | Bonny |
| 2002/0035243 A1 | 3/2002 | Imfeld et al. |
| 2002/0120100 A1 | 8/2002 | Bonny |
| 2003/0032594 A1 | 2/2003 | Bonny |
| 2005/0004125 A1 | 1/2005 | Freyne et al. |
| 2005/0124640 A1 | 6/2005 | Cardozo et al. |
| 2010/0130486 A1 | 5/2010 | Singh et al. |
| 2014/0031361 A1 | 1/2014 | Bauer et al. |

FOREIGN PATENT DOCUMENTS

| | | | | |
|---|---|---|---|---|
| WO | WO-2010085597 A1 | * | 7/2010 | ........... C07D 471/22 |
| WO | 2011151360 A1 | | 12/2011 | |
| WO | 2015021149 A1 | | 2/2015 | |

OTHER PUBLICATIONS

Mahajan, Kiran. Cancer Lett. (2013) 338(2) 185-192.*
MedicineNet.com (2004). Web<http://www.medterms.com>.*
National Cancer Institute. Prostate Cancer Prevention, (2010) Web: < https://www.cancer.gov/types/prostate/patient/prostate-prevention-pdq>.*
Antonarakis, et al., (2014). AR-V7 and resistance to enzalutamide and abiraterone in prostate cancer. New Engl. J. Med. 371, 1028-1038.
Aqeilan, et al., (2007). WWOX in biological control and tumorigenesis. J. Cell. Physiol. 212, 307-10.
Arora, et al. (2013). Glucocorticoid receptor confers resistance to antiandrogens by bypassing androgen receptor blockade. Cell 155, 1309-1322.
Balbas, et al., (2013). Overcoming mutation-based resistance to antiandrogens with rational drug design. eLife 2, e00499.
Bebbington, et al., (2009). The discovery of the potent aurora inhibitor MK-0457 (VX-680). Bioorg. Med. Chem. Lett. 19, 3586-92.
Bennett, et al., (2014). Enzalutamide (Xtandi) for patients with metastatic, resistant prostate cancer. The Annals of Pharmacotherapy 48, 530-537.
Bossi, et al., (2010). Crystal structures of anaplastic lymphoma kinase in complex with ATP competitive inhibitors. Biochem. 49, 6813-25.
Burgering, et al., (1995). Protein kinase B (c-Akt) in phosphatidylinositol-3-OH kinase signal transduction. Nature 376, 599-602.

(Continued)

*Primary Examiner* — Emily A Bernhardt
*Assistant Examiner* — Laura M Daniel
(74) *Attorney, Agent, or Firm* — Meunier Carlin & Curfman LLC

(57) ABSTRACT

Described are cancer therapies and anti-cancer compounds. In particular, disclosed are inhibitors of ACK1 tyrosine kinase and their use in the treatment of cancer. Methods of screening for new ACK1 tyrosine kinase inhibitors are also disclosed. In specific example, compound having Formula I are disclosed.

9 Claims, 12 Drawing Sheets

(56) References Cited

OTHER PUBLICATIONS

Burnstein, K.L. (2005). Regulation of androgen receptor levels: implications for prostate cancer progression and therapy. J. Cellular Biochem. 95, 657-669.
Cai, et al. (2011). Androgen receptor gene expression in prostate cancer is directly suppressed by the androgen receptor through recruitment of lysine-specific demethylase 1. Cancer Cell 20, 457-471.
Carter, et al., (2005). Inhibition of drug-resistant mutants of ABL, KIT, and EGF receptor kinases. Proc. Natl. Acad. Sci. USA 102, 11011-6.
Chaboissier, et al., (2004). Functional analysis of Sox8 and Sox9 during sex determination in the mouse. Development 131, 1891-1901.
Davis, et al., (2011). Comprehensive analysis of kinase inhibitor selectivity. Nat. Biotechnol. 29, 1046-51.
Dehm, et al., (2008). Splicing of a novel androgen receptor exon generates a constitutively active androgen receptor that mediates prostate cancer therapy resistance. Cancer research 68, 5469-5477.
DiMauro EF, et al. Discovery of 4-amino-5,6-biaryl-furo[2,3-d]pyrimidines as inhibitors of Lck: development of an expedient and divergent synthetic route and preliminary SAR. Bioorg. Med. Chem. Lett. 2007, 17, 2305-9.
Drake, et al. (2012). Oncogene-specific activation of tyrosine kinase networks during prostate cancer progression. Proc. Natl. Acad. Sci. USA 109, 1643-1648.
Franke TF, et al. The protein kinase encoded by the Akt proto-oncogene is a target of the PDGF-activated phosphatidylinositol 3-kinase. Cell 1995, 81:727-36.
Galkin AV, et al. Identification of NVP-TAE684, a potent, selective, and efficacious inhibitor of NPM-ALK. Proc. Natl. Acad. Sci. USA 2007, 104:270-5.
Gao, et al. (2013). Androgen receptor promotes ligand-independent prostate cancer progression through c-Myc upregulation. PloS one 8, e63563.
Golas JM, et al. SKI-606, a 4-anilino-3-quinolinecarbonitrile dual inhibitor of Src and Abl kinases, is a potent antiproliferative agent against chronic myelogenous leukemia cells in culture and causes regression of K562 xenografts in nude mice. Cancer Res. 2003, 63:375-81.
Goodwin, et al. (2013). A hormone-DNA repair circuit governs the response to genotoxic insult. Cancer Discovery 3, 1254-1271.
Grad, et al., (2001). The androgen receptor (AR) amino-terminus imposes androgen-specific regulation of AR gene expression via an exonic enhancer. Endocrinology 142, 1107-1116.
Grasso, et al., (2012). The mutational landscape of lethal castration-resistant prostate cancer. Nature 487, 239-243.
Greenlee, et al., (2000). Cancer statistics, 2000. CA: a cancer journal for clinicians 50, 7-33.
Grossmann, et al., (2001). Androgen receptor signaling in androgen-refractory prostate cancer. J. National Cancer Institute 93, 1687-697.
Guo, et al., (2006). Regulation of androgen receptor activity by tyrosine phosphorylation. Cancer Cell 10, 309-319.
Guo, et al., (2009). A novel androgen receptor splice variant is up-regulated during prostate cancer progression and promotes androgen depletion-resistant growth. Cancer Res. 69, 2305-2313.
Hu, et al., (2009). Ligand-independent androgen receptor variants derived from splicing of cryptic exons signify hormone-refractory prostate cancer. Cancer Res. 69, 16-22.
Jiao, et al. (2012). Synthesis and optimization of substituted furo[2,3-d]-pyrimidin-4-amines and 7H-pyrrolo[2,3-d]pyrimidin-4-amines as ACK1 inhibitors. Bioorg. Med. Chem. Lett. 22, 6212-7.
Jin, et al., (2013). Discovery of potent, selective and orally bioavailable imidazo[1,5-a]pyrazine derived ACK1 inhibitors. Bioorg. Med. Chem. Lett. 23, 979-84.
Joseph, et al. (2013). A clinically relevant androgen receptor mutation confers resistance to second-generation antiandrogens enzalutamide and ARN-509. Cancer Discovery 3, 1020-1029.
Kopecky DJ, et al. Identification and optimization of N3, N6-diaryl-1H-pyrazolo[3,4-d]pyrimidine-3,6-diamines as a novel class of ACK1 inhibitors. Bioorg. Med. Chem. Lett. 2008, 18:6352-6.
Korpal, et al. (2013). An F876L mutation in androgen receptor confers genetic and phenotypic resistance to MDV3100 (enzalutamide). Cancer Discovery 3, 1030-1043.
Lawrence, et al., (2012). Development of o-chlorophenyl substituted pyrimidines as exceptionally potent aurora kinase inhibitors. J. Med. Chem. 55, 7392-416.
Lawrence, et al. (2015). Development of novel ACK1/TNK2 inhibitors using a fragment-based approach. J. Med. Chem. 58, 2746-2763.
Li, et al., (2010). A chemical and phosphoproteomic characterization of dasatinib action in lung cancer. Nat. Chem. Biol. 6, 291-9.
Liu, et al., (2010). Dasatinib inhibits site-specific tyrosine phosphorylation of androgen receptor by Ack1 and Src kinases. Oncogene 29, 3208-16.
Lonergan, et al., (2011). Androgen receptor signaling in prostate cancer development and progression. J. Carcinogenesis 10, 20.
Lu, et al., (2015). Are androgen receptor variants a substitute for the full-length receptor? Nature Reviews Urology 12, 137-144.
Mahajan, et al., (2005). Activated tyrosine kinase Ack1 promotes prostate tumorigenesis: role of Ack1 in polyubiquitination of tumor suppressor Wwox. Cancer Res. 65, 10514-10523.
Mahajan, et al., (2007). Activated Cdc42-associated kinase Ack1 promotes prostate cancer progression via androgen receptor tyrosine phosphorylation. Proc. Natl. Acad. Sci. U.S.A. 104, 8438-8443.
Mahajan, et al., (2010). Ack1 mediated AKT/PKB tyrosine 176 phosphorylation regulates its activation. PloS one 5, e9646.
Mahajan, et al., (2010). Effect of Ack1 tyrosine kinase inhibitor on ligand-independent androgen receptor activity. Prostate 70, 1274-85.
Mahajan, et al., (2010). Shepherding AKT and androgen receptor by Ack1 tyrosine kinase. J. Cellular Physiol. 224, 327-333.
Mahajan, et al., (2012). Ack1 tyrosine kinase activation correlates with pancreatic cancer progression. Am. J. Pathol. 180, 1386-93.
Mahajan, et al., (2012). Ack1-mediated androgen receptor phosphorylation modulates radiation resistance in castration-resistant prostate cancer. J. Biol. Chem. 287(26), 22112-22.
Mahajan, et al., (2012). H2B Tyr37 phosphorylation suppresses expression of replication-dependent core histone genes. Nature structural & molecular biology 19, 930-937.
Mahajan, et al., (2013). ACK1 tyrosine kinase: targeted inhibition to block cancer cell proliferation. Cancer Lett. 338, 185-92.
Mahajan, et al., (2014). ACK1 tyrosine kinase interacts with histone demethylase KDM3A to regulate the mammary tumor oncogene HOXA1. J. Biol. Chem. 289, 28179-28191.
Mahajan, et al., (2015). ACK1/TNK2 tyrosine kinase: molecular signaling and evolving role in cancers. Oncogene 34, 4162-4167.
Malik, et al. (2015). Targeting the MLL complex in castration-resistant prostate cancer. Nature Med. 21, 344-352.
Manning, et al., (2007). AKT/PKB signaling: navigating downstream. Cell 129, 1261-74.
Martin, et al., (2012). A novel mechanism by which small molecule inhibitors induce the DFG flip in Aurora A. ACS Chem. Biol. 7, 698-706.
Martin, et al., (2007). Discovery of novel 2,3-diarylfuro[2,3-b]pyridin-4-amines as potent and selective inhibitors of Lck: synthesis, SAR, and pharmacokinetic properties. Bioorg. Med. Chem. Lett. 17, 2299-304.
Metz, et al., (2011). Navigating the kinome. Nat. Chem. Biol. 7, 200-2.
Miduturu, et al., (2011). High-throughput kinase profiling: a more efficient approach toward the discovery of new kinase inhibitors. Chem. Biol. 18, 868-79.
Moriarty, et al., (2006). The synthesis and SAR of 2-amino-pyrrolo[2,3-d]pyrimidines: a new class of Aurora-A kinase inhibitors. Bioorg. Med. Chem. Lett. 16, 5778-83.
Perkins, et al., (1999). Probability-based protein identification by searching sequence databases using mass spectrometry data. Electrophoresis 20, 3551-3567.
Polkinghorn, et al., (2013). Androgen receptor signaling regulates DNA repair in prostate cancers. Cancer Discovery 3, 1245-1253.

(56) References Cited

OTHER PUBLICATIONS

Remsing-Rix, et al., (2009). Global target profile of the kinase inhibitor bosutinib in primary chronic myeloid leukemia cells. Leukemia 23, 477-85.

Robinson, et al. (2015). Integrative clinical genomics of advanced prostate cancer. Cell 161, 1215-1228.

Spratt, et al., (2015). Androgen Receptor Upregulation Mediates Radioresistance after Ionizing Radiation. Cancer Res. 75, 4688-4696.

Subramanian, et al. (2005). Gene set enrichment analysis: a knowledge-based approach for interpreting genome-wide expression profiles. Proc. Natl. Acad. Sci. USA. 102, 15545-15550.

Tan, et al., (2014). Bosutinib inhibits migration and invasion via ACK1 in KRAS mutant non-small cell lung cancer. Mol. Cancer 13:13.

Tari, et al., (2007). Structural basis for the inhibition of Aurora A kinase by a novel class of high affinity disubstituted pyrimidine inhibitors. Bioorg. Med. Chem. Lett. 2007, 17:688-691.

Taylor, et al. (2010). Integrative genomic profiling of human prostate cancer. Cancer Cell 18, 11-22.

Toyoizumi, et al., (1999). Combined therapy with chemotherapeutic agents and herpes simplex virus type IICP34.5 mutant (HSV-1716) in human non-small cell lung cancer. Human Gene Therapy 10(18), 3013-3029.

Tran, et al. (2009). Development of a second-generation antiandrogen for treatment of advanced prostate cancer. Science NY 324, 787-790.

Van der Horst, et al. (2005). Metastatic properties and genomic amplification of the tyrosine kinase gene ACK1. Proc. Natl. Acad. Sci. USA. 102, 15901-15906.

Watson, et al., (2015). Emerging mechanisms of resistance to androgen receptor inhibitors in prostate cancer. Nature Rev. 15, 701-711.

Watson, et al., (2010). Constitutively active androgen receptor splice variants expressed in castration-resistant prostate cancer require full-length androgen receptor. Proc. Natl. Acad. Sci. U.S.A. 107, 16759-16765.

Wysocka, et al., (2005). WDR5 associates with histone H3 methylated at K4 and is essential for H3 K4 methylation and vertebrate development. Cell 121, 859-872.

Xu, et al. (2009). Regulation of androgen receptor transcriptional activity and specificity by RNF6-induced ubiquitination. Cancer Cell 15, 270-282.

Yang, et al., (2014). Dual Aurora A and JAK2 kinase blockade effectively suppresses malignant transformation. Oncotarget 5, 2947-61.

Yates, et al., (1995). Method to correlate tandem mass spectra of modified peptides to amino acid sequences in the protein database. Anal. Chem. 67, 1426-1436.

Zhao, et al. (2007). Whole-genome mapping of histone H3 Lys4 and 27 trimethylations reveals distinct genomic compartments in human embryonic stem cells. Cell Stem Cell 1, 286-298.

International Preliminary Report on Patentability issued for International Application No. PCT/US2016/045096, dated Feb. 15, 2018.

International Search Report and Written Opinion issued for International Application No. PCT/US2016/045096, dated Oct. 20, 2016.

Extended European Search Report issued in EP3.55.136760, dated Nov. 16, 2018.

* cited by examiner

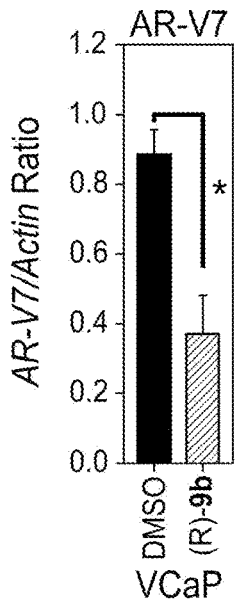 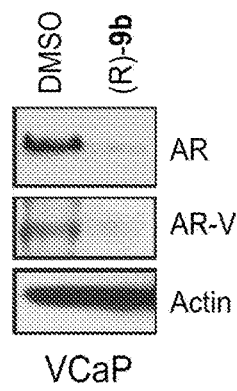 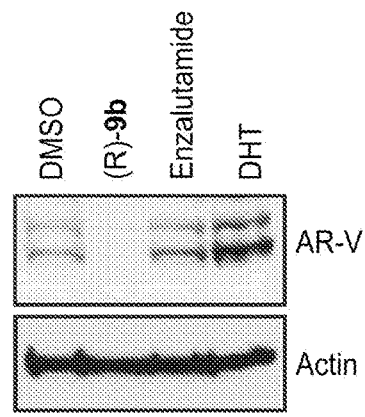
*FIG. 1A*     *FIG. 1B*     *FIG. 1C*
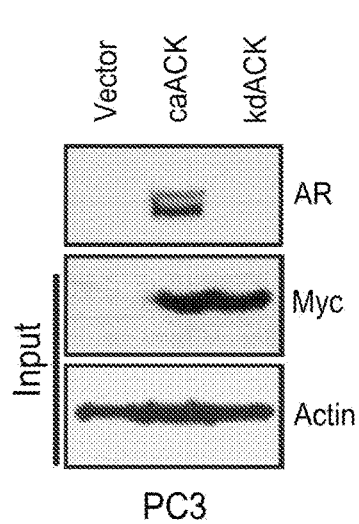 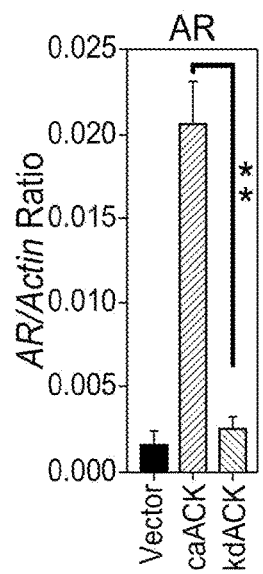 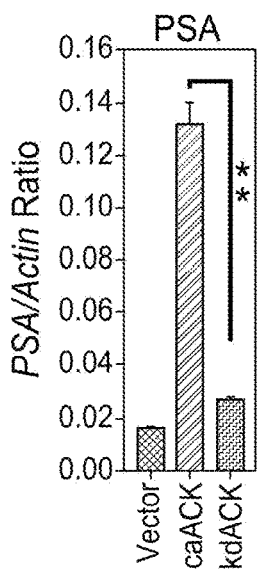
*FIG. 1D*     *FIG. 1E*     *FIG. 1F*

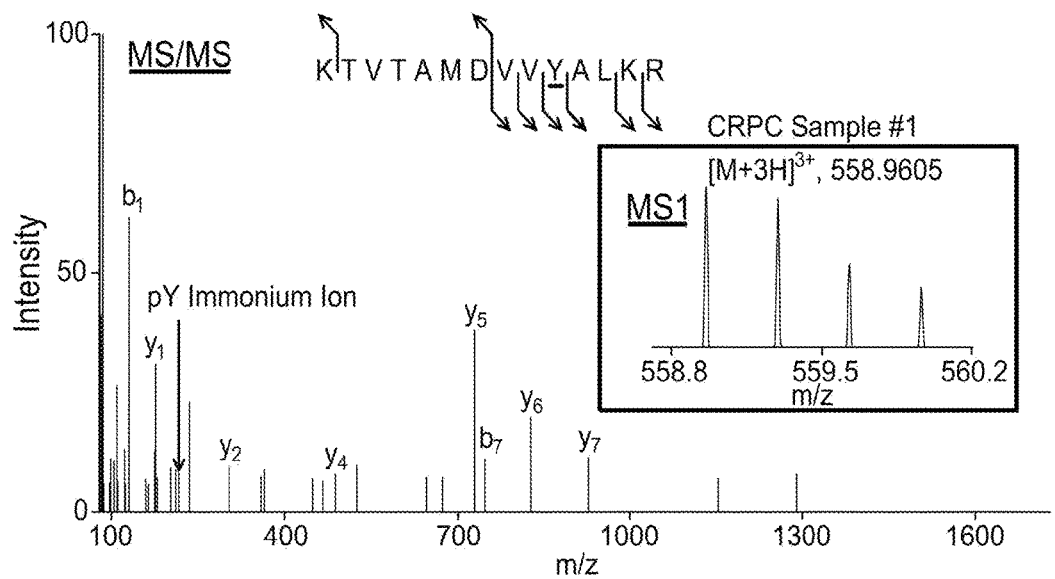
FIG. 3A
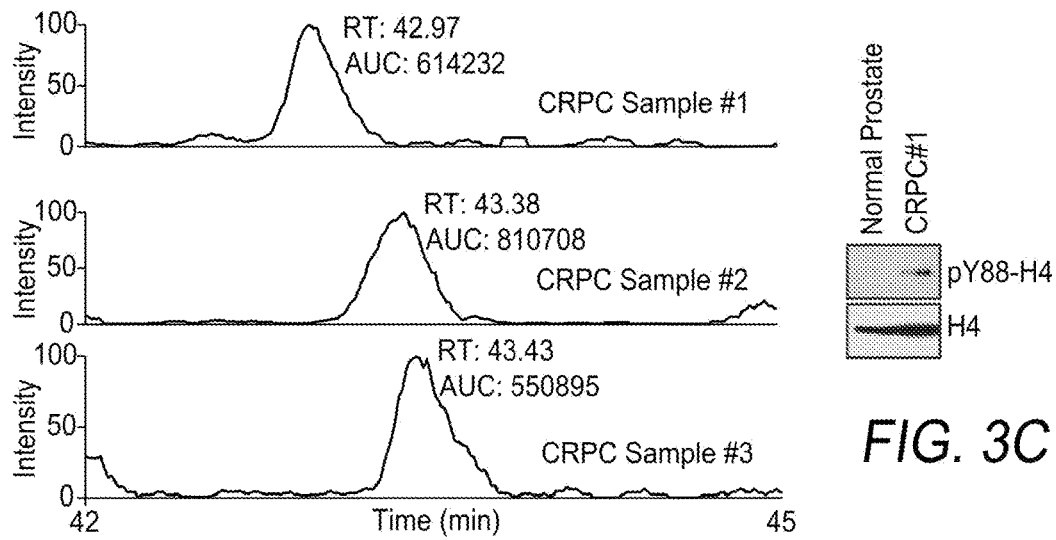
FIG. 3B
FIG. 3C

C4-2B Xenografts

INHIBITORS OF ACK1/TNK2 TYROSINE KINASE

CROSS REFERENCE TO RELATED APPLICATIONS

This application claims the benefit of priority to U.S. Provisional Applications 62/200,084, filed Aug. 2, 2015, and 62/299,178, filed Feb. 24, 2016, the disclosures of which are incorporated by reference herein in their entireties.

ACKNOWLEDGEMENT OF GOVERNMENT SUPPORT

This invention was made with Government support under Grant No. CA135328 awarded by the National Institutes of Health. The Government has certain rights in the invention.

FIELD

The subject matter disclosed herein relates generally to cancer therapy and to anti-cancer compounds. More specifically, the subject matter disclosed herein relates to inhibitors of ACK1 tyrosine kinase and their use in the treatment of cancer. Methods of screening for selective inhibitors of ACK1 kinases are also disclosed.

BACKGROUND

ACK1, also known as TNK2, is a non-receptor tyrosine kinase that is expressed in diverse cell types. It integrates signals from several important ligand-activated receptor tyrosine kinases (RTKs), for example, EGFR, MerTK, HER2, PDGFR and insulin receptor to initiate intracellular signaling cascades. The ACK1 tyrosine kinase is aberrantly activated, amplified or mutated in many types of human cancers including prostate, breast, pancreatic, ovarian and lung cancers (Mahajan K, et al. ACK1 tyrosine kinase: targeted inhibition to block cancer cell proliferation. *Cancer Lett.* 2013; 338:185-92). Aberrantly activated ACK1 drives cell growth via a number of molecular mechanisms (Mahajan K, et al. Shepherding AKT and androgen receptor by ACK1 tyrosine kinase. *J. Cell. Physiol.* 2010; 224:327-33). Several recent discoveries underscore its tumor promoting functions. For example, ACK1 phosphorylates the androgen receptor, at Tyr267 in its transactivation domain, in an androgen-independent manner to promote castration resistant prostate cancer (CRPC) growth (Mahajan K, et al. Activated Cdc42-associated kinase ACK1 promotes prostate cancer progression via androgen receptor tyrosine phosphorylation. *Proc. Natl. Acad. Sci. USA* 2007; 104:8438-43; Mahajan K, et al. ACK1-mediated androgen receptor phosphorylation modulates radiation resistance in castration-resistant prostate cancer. *J. Biol. Chem.* 2012; 287(26): 22112-22). ACK1 has been shown to promote prostate tumorigenesis by phosphorylating the WW domain-containing oxidoreductase (Wwox) tumor suppressor (Aqeilan R I, et al. WWOX in biological control and tumorigenesis. *J. Cell. Physiol.* 2007; 212:307-10) on Tyr287 leading to its polyubiquitination and subsequent degradation (Mahajan K, et al. Activated tyrosine kinase ACK1 promotes prostate tumorigenesis: role of ACK1 in polyubiquitination of tumor suppressor Wwox. *Cancer Res.* 2005; 65:10514-23). It has also been shown that ACK1 phosphorylates and activates the key signaling kinase AKT, which plays important roles in human physiology and disease (Franke T F, et al. The protein kinase encoded by the Akt proto-oncogene is a target of the PDGF-activated phosphatidylinositol 3-kinase. *Cell* 1995; 81:727-36; Burgering B M, et al. Protein kinase B (c-Akt) in phosphatidylinositol-3-OH kinase signal transduction. *Nature* 1995; 376:599-602; Manning B D, et al. AKT/PKB signaling: navigating downstream. *Cell* 2007; 129:1261-74). When AKT is phosphorylated on Tyr176 by ACK1 it functionally participates in the progression of breast cancer by suppressing pro-apoptotic pathways (Mahajan K, et al. ACK1 mediated AKT/PKB tyrosine 176 phosphorylation regulates its activation. *PloS one* 2010; 5:e9646). Conversely knockdown of ACK1 expression by siRNA suppressed AKT activation in MCF7 breast cancer cell line and increased expression of pro-apoptotic genes such as Bim and Fas (Id.). ACK1 transgenic mice developed prostatic intra-epithelial neoplasia (PINs), indicating that its activation is crucial in tumorigenesis (Id.). Significant evidence in pre-clinical models therefore validates ACK1 as a target for anticancer drugs, and has driven the development of many ACK1 inhibitors. Selected examples of ACK1 inhibitors are as follows:

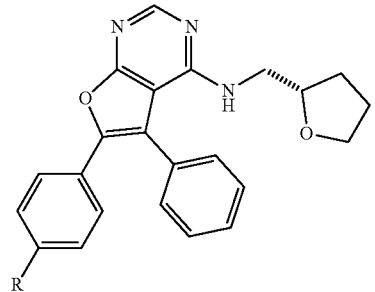

1a R = O(CH$_2$)$_2$NMe$_2$
ACK1 IC$_{50}$ 11 nM; Lck IC$_{50}$ 6 nM
1b (AIM-100), R = H
ACK1 IC$_{50}$ 24 nM; Lck IC$_{50}$ 122 nM

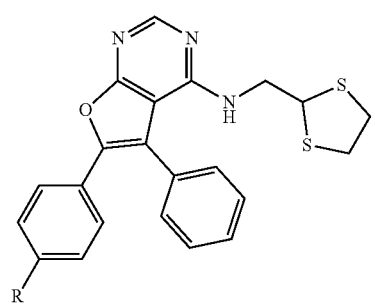

1c
R = O(CH$_2$)$_2$NMe$_2$
ACK1 K$_i$ 0.3 nM; Lck K$_i$ 138 nM

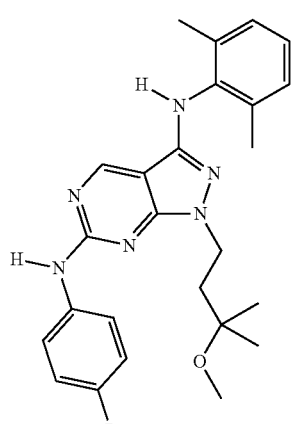

R = H ACK1 IC$_{50}$ 2 nM,

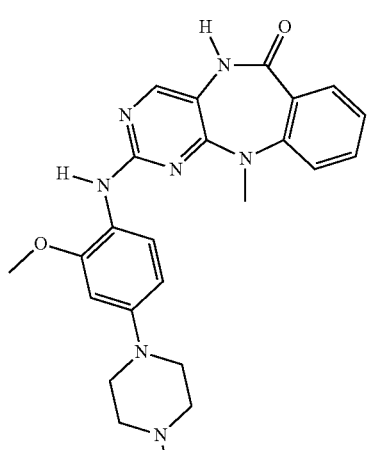

ACK1 K$_d$ 2 nM,

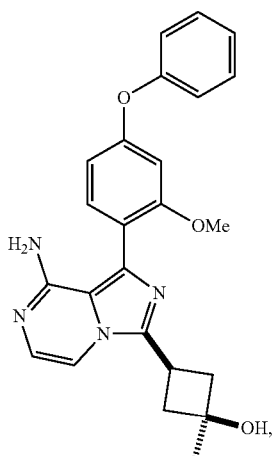

ACK1 IC$_{50}$ 110 nM;
ACK1 IC$_{50}$ (cell) 35 nM

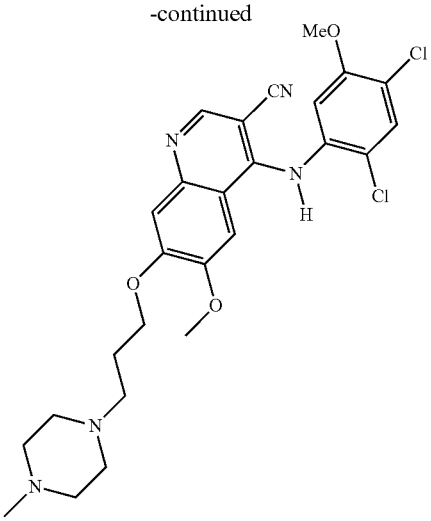

Bosutinib, ACK1 IC$_{50}$ 2.7 nM

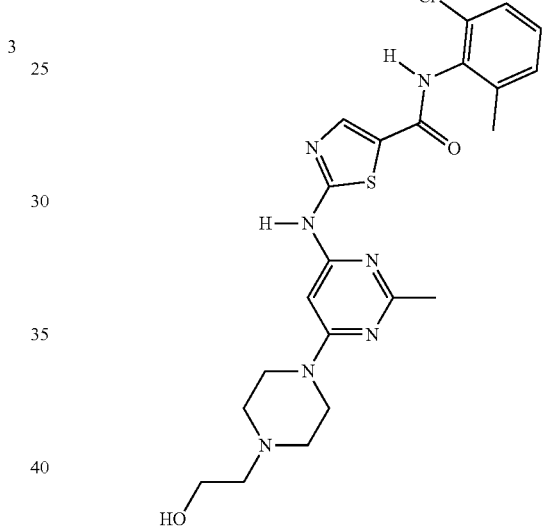

Dasatinib, ACK1 K$_D$ 6 nM

A series of 4-amino-5,6-biaryl-furo[2,3-d]pyrimidines (structures 1a-1c) were found to inhibit ACK1 and the related member of the src kinase family Lck (lymphocyte-specific kinase) (DiMauro E F, et al. Discovery of 4-amino-5,6-biaryl-furo[2,3-d]pyrimidines as inhibitors of Lck: development of an expedient and divergent synthetic route and preliminary SAR. *Bioorg. Med. Chem. Lett.* 2007; 17, 2305-9; Martin M W, et al. Discovery of novel 2,3-diaryl-furo[2,3-b]pyridin-4-amines as potent and selective inhibitors of Lck: synthesis, SAR, and pharmacokinetic properties. *Bioorg. Med. Chem. Lett.* 2007; 17:2299-304). For example, compound 1a potently inhibits both ACK1 and Lck and was useful in the development of further compounds for the treatment of T cell-mediated autoimmune and inflammatory disease as a consequence of Lck inhibition. Compound 1b (AIM-100) was used as a chemical probe for ACK1 inhibition, since it was reported to inhibit Lck to a lesser extent (ACK1:Lck 5:1) than 1a (Lck:ACK1 1.8:1). AIM-100 inhibits ACK1 dependent AKT Tyr176 (Mahajan K, et al. ACK1 tyrosine kinase activation correlates with pancreatic cancer progression. *Am. J. Pathol.* 2012; 180:1386-93) in pancreatic cancer cells and AR Tyr267 (Mahajan K, et al. Effect of ACK1 tyrosine kinase inhibitor on ligand-independent androgen receptor activity. *Prostate* 2010; 70:1274-85) phosphorylation. AIM-100 also inhibits castration and radioresistant prostate xenograft tumor growth via inhibition of AR Tyr267 phosphorylation (Mahajan K, et al. ACK1-mediated androgen receptor phosphorylation modulates radiation resistance in castration-resistant prostate cancer. *J. Biol. Chem.* 2012; 287:22112-22). A study of further members of the 4-amino-5,6-biaryl-furo[2,3-d]pyrimidine series showed that the dithiolane 1c was an exceptionally potent ACK1 inhibitor ($K_i$ 0.3 nM). This compound inhibits the growth of a cell line which is dependent upon ACK1 with an $IC_{50}$ of 5 nM. However, its poor pharmacokinetic properties (attributed to oxidation of both the dithiolane ring and $NMe_2$) precluded use in an animal model. A series of pyrazolopyrimidines of type 2 have also been developed by Amgen as ACK1 inhibitors (Kopecky D J, et al. Identification and optimization of N3,N6-diaryl-1H-pyrazolo[3,4-d]pyrimidine-3,6-diamines as a novel class of ACK1 inhibitors. *Bioorg. Med. Chem. Lett.* 2008; 18:6352-6). For example, compound 2 potently inhibits ACK1 in vitro ($IC_{50}$ 2 nM) and in intact cells, as measured by inhibition of ACK1 autophosphorylation ($IC_{50}$ 20 nM). Gray and co-workers have identified the ACK1 inhibitor 3, by high throughput kinase profiling of a focused library of pyrimidine-diazepines (Miduturu C V, et al. High-throughput kinase profiling: a more efficient approach toward the discovery of new kinase inhibitors. *Chem. Biol.* 2011; 18:868-79). This compound abolishes EGF induced ACK1 autophosphorylation (Tyr284) in HEK293 cells at concentrations of 2 μM. It also inhibits A549 lung cancer cell growth at 10 μM. A series of imidazopyrazine based ACK1 inhibitors have been developed by Jin and co-workers at OSI/Astellas (Jin M, et al. Discovery of potent, selective and orally bioavailable imidazo[1,5-a]pyrazine derived ACK1 inhibitors. *Bioorg. Med. Chem. Lett.* 2013; 23:979-84). For example, compound 4 is a potent ACK1 inhibitor orally bioavailable in mouse models and good experimental ADMET properties. It inhibits ACK1 mediated phosphorylation of poly-(GT) in an AlphaScreen assay with an $IC_{50}$ of 110 nM. It potently inhibits ACK1 in a cellular context. In NCI-H1703 human non-small cell lung cancer cells its $IC_{50}$ for ACK1 inhibition is 35 nM as measured by an ELISA assay. In this assay ACK1 from the cell lysates is captured on an ELISA plate by ACK1 antibodies. The extent of phosphorylation of ACK1 was determined using an enzyme-linked antibody that recognizes phosphotyrosine residues. Several promiscuous kinase inhibitors have been shown to inhibit ACK1. For example, the Src/Abl kinase inhibitor bosutinib (Golas J M, et al. SKI-606, a 4-anilino-3-quinolinecarbonitrile dual inhibitor of Src and Abl kinases, is a potent antiproliferative agent against chronic myelogenous leukemia cells in culture and causes regression of K562 xenografts in nude mice. *Cancer Res.* 2003; 63:375-81) inhibits ACK1 with an $IC_{50}$ of 2.7 nM (Remsing R, et al. Global target profile of the kinase inhibitor bosutinib in primary chronic myeloid leukemia cells. *Leukemia* 2009; 23:477-85). Bosutinib was found to inhibit cell migration and invasion but not viability in a panel of non-small cell lung cancer (NSCLC) cell lines (Tan D S, et al. Bosutinib inhibits migration and invasion via ACK1 in KRAS mutant non-small cell lung cancer. *Mol. Cancer* 2014; 13:13). These effects were not seen when ACK1 was knocked-down specifically in K-Ras mutant cell lines. Dasatinib, another BCR/Abl and Src family tyrosine kinase inhibitor, inhibits ACK1 with a $K_D$ of 6 nM (Carter T A, et al. Inhibition of drug-resistant mutants of ABL, KIT, and EGF receptor kinases. *Proc. Natl. Acad. Sci. USA* 2005; 102:11011-6). Dasatinib was shown to inhibit both ACK1 autophosphorylation and AR phosphorylation of Tyr-267 in heregulin-stimulated human prostate cancer LNCaP cells with $IC_{50}$s<5 nM (Liu Y, et al. Dasatinib inhibits site-specific tyrosine phosphorylation of androgen receptor by ACK1 and Src kinases. *Oncogene* 2010; 29:3208-16). Additionally, dasatinib significantly reduced the growth of LNCaP cells expressing constitutively activated ACK1 in a mouse xenograft model (Id.). Chemical and phosphoproteomic approaches revealed ACK1 to be a target of dasatinib in human lung cancer cells (Li J, et al. A chemical and phosphoproteomic characterization of dasatinib action in lung cancer. *Nat. Chem. Biol.* 2010; 6:291-9).

ACK1 inhibitors are developed by analysis of known ACK1 inhibitors including 1b (AIM-100), the pyrazolopyrimidine derivative 5 (Kopecky D J, et al. Identification and optimization of N3,N6-diaryl-1H-pyrazolo[3,4-d]pyrimidine-3,6-diamines as a novel class of ACK1 inhibitors. *Bioorg. Med. Chem. Lett.* 2008; 18:6352-6) and the ALK inhibitor 6 (TAE684) (Galkin A V, et al. Identification of NVP-TAE684, a potent, selective, and efficacious inhibitor of NPM-ALK. *Proc. Natl. Acad. Sci. USA* 2007; 104:270-5) (which strongly cross-inhibits ACK1 from published inhibitor profiling data sets; $K_d$ 2 nM (Davis M I, et al. Comprehensive analysis of kinase inhibitor selectivity. *Nat. Biotechnol.* 2011; 29:1046-51) and $K_i$ 1 nM (Metz J T, et al. Navigating the kinome. *Nat. Chem. Biol.* 2011; 7:200-2)). The binding modes of the three inhibitors are shown in FIG. 1A through 1F, as derived from the X-ray structure of 5 with ACK1 (pdb 3EQR); 1b (AIM-100) modeled from the X-ray structure of an analog with ACK1 (Jiao X, et al. Synthesis and optimization of substituted furo[2,3-d]-pyrimidin-4-amines and 7H-pyrrolo[2,3-d]pyrimidin-4-amines as ACK1 inhibitors. *Bioorg. Med. Chem. Lett.* 2012; 22:6212-7) (pdb 4EWH); 6 modeled from its X-ray structure with ALK (Bossi R T, et al. Crystal structures of anaplastic lymphoma kinase in complex with ATP competitive inhibitors. *Biochem.* 2010; 49:6813-25) (pdb 2XB7). These bind the ACK1 hinge residues Ala-208 via the pyrimidyl group, positioning groups in the hydrophobic pocket beyond the gatekeeper, and in the ribose binding region (Galkin A V, et al. Identification of NVP-TAE684, a potent, selective, and efficacious inhibitor of NPM-ALK. *Proc. Natl. Acad. Sci. USA* 2007; 104:270-5). The bisanilinopyrimidine scaffold has been long recognized as a classical kinase inhibitor motif (Bebbington D, et al. The discovery of the potent aurora inhibitor MK-0457 (VX-680). *Bioorg. Med. Chem. Lett.* 2009; 19:3586-92; Moriarty K J, et al. The synthesis and SAR of 2-amino-pyrrolo[2,3-d]pyrimidines: a new class of Aurora-A kinase inhibitors. *Bioorg. Med. Chem. Lett.* 2006; 16:5778-83; Tari L W, et al. Structural basis for the inhibition of Aurora A kinase by a novel class of high affinity disubstituted pyrimidine inhibitors. *Bioorg. Med. Chem. Lett.* 2007; 17:688-691). Aurora A inhibitors were reported using a bisanilinopyrimidine scaffold (Lawrence H R, et al. Development of o-chlorophenyl substituted pyrimidines as exceptionally potent aurora kinase inhibitors. *J. Med. Chem.* 2012; 55:7392-416; Martin M P, et al. A novel mechanism by which small molecule inhibitors induce the DFG flip in Aurora A. *ACS Chem. Biol.* 2012; 7:698-706; Yang H, et al. Dual Aurora A and JAK2 kinase blockade effectively suppresses malignant transformation. *Oncotarget* 2014; 5:2947-61). In the development of novel ACK1 inhibitors, the design process incorporated an aminopyrimidine structure as the hinge binding group (FIG. 1D) and the fragments of 1b, 5 and 6 as $R^1$, $R^2$ and $R^3$ (FIG. 1D) groups to create hybrid structures in a mix and match process (FIG. 1A through 1F).

What are needed are new compounds and methods for inhibiting ACK1 and uses of such compounds. The subject matter disclosed herein addresses these and other needs.

SUMMARY

In accordance with the purposes of the disclosed materials and methods, as embodied and broadly described herein, the disclosed subject matter, in one aspect, relates to compounds, compositions and methods of making and using compounds and compositions. In specific aspects, the disclosed subject matter relates to cancer therapy and to anti-cancer compounds. More specifically, the subject matter disclosed herein relates to inhibitors of ACK1 tyrosine kinase and their use in the treatment of cancer. Methods of screening for new ACK1 tyrosine kinase inhibitors are also disclosed.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

FIG. 1A through 1F. Inhibition of ACK1 kinase activity by (R)-9bMS (DZ1-067 mesylate salt) suppresses AR and AR-V7 expression. FIG. 1A shows qRT-PCR analysis of AR-V7 in VCaP cells treated with (R)-9bMS (3.5 µM, 16 hr). Data represent mean±s.e.m. (n=3) from one of three independent experiments. *p<0.05. FIG. 1B and FIG. 1C show immunoblot analysis of androgen-deprived VCaP and LAPC4 cells treated with (R)-9bMS. FIG. 1D shows immunoblot analysis of PC3 cells transfected with caACK or kdACK constructs. FIG. 1E and FIG. 1F show qRT-PCR analysis of AR and PSA in PC3 cells transfected with caACK or kdACK constructs. Data represent mean±s.e.m. (n=3) from one of three independent experiments. **p<0.01.

FIG. 2A shows immunoblot analysis of serum and androgen starved LNCaP and LAPC4 cells treated with (R)-9bMS (5 µM), followed by insulin like growth factor (IGF for 40 min) or platelet derived growth factor (PDGF for 60 min) treatment. FIG. 2B shows immunoblot analysis of serum and androgen starved LNCaP-C4-2B and LAPC4 cells treated with (R)-9bMS (5 µM), enzalutamide (5 µM) or DHT (10 nM), followed by IGF (40 min) or EGF (60 min) treatment. FIG. 2C shows immunoblot analysis of LNCaP cells electroporated with control or ACK1 siRNA, followed by with IGF ligand treatment.

FIG. 3A through 3C. Detection of Histone H4 Y88-phosphorylation in human CRPCs. FIG. 3A shows MS data from when histones were purified from 3 freshly frozen human CRPC samples and were digested. ArgC digested peptide KTVTAMDVVYALKR (SEQ ID No.: 1) was observed as triply charged, with m/z 558.9605, which represents a mass error of 1.2 ppm; MS/MS spectrum was identified using Mascot with a score of 32.1 in CRPC sample#1. FIG. 3B shows label-Free Quantification of pTyrosine 88 in human histone H4 in CRPC samples #1-3. Xcalibur software (Thermo) was used to extract ion chromatogram of H4 pY-88 containing Arg-C digested peptide KTVTAMDVVYALKR (SEQ ID No.: 1). m/z tolerance was set to +/−0.02 Th and retention time (RT) tolerance was set to +/−60 seconds. Area under the curve (AUC) values were used to quantify relative intensities between samples. FIG. 3C shows immunoblot analysis of total histones isolated from freshly frozen human CRPC sample#1 and a normal prostate sample.

FIG. 4A shows the ChIP-sequencing reveal deposition of pY88-H4 epigenetic marks at the three distinct locations upstream of AR gene. FIG. 4B shows the human AR gene and the pY88-H4 binding sites, AREM1-3, located upstream of AR transcription start site (TSS).

FIG. 5A through 5D show ChIP with pY88-H4 antibodies, followed by qPCR using primers corresponding to AREM1-3 and control (gene desert) sites of C4-2B cells treated with (R)-9bMS. Data represent mean±s.e.m. (n=3) from one of three independent experiments. **p<0.01. FIG. 5E shows ChIP with AR antibodies, followed by qPCR using primers corresponding to AREM1 site of C4-2B cells transfected with AR and control siRNA. Data represent mean±s.e.m. (n=3) from one of three independent experiments. *p<0.05, **p<0.01. FIGS. 5F and 5G show ChIP with pY88-H4 antibodies, followed by qPCR using primers corresponding to AREM2 and AREM1 site of C4-2B cells transfected with ACK1, AR and control siRNA. Data represent mean±s.e.m. (n=3) from one of three independent experiments. *p<0.05, **p<0.01. FIG. 5H shows ChIP with pY88-H4 antibodies, followed by qPCR using primers corresponding to AREM1 site of LAPC4 and ACK1-KO (by CRISPR/Cas9 editing) LAPC4 cells. Data represent mean±s.e.m. (n=3) from one of three independent experiments. *p<0.05. FIGS. 5I and 5J show qRT-PCR analysis of AR and PSA in LAPC4 cells transfected with FLAG-tagged H4 or Y88F mutant H4 expressing constructs. Data represent mean±s.e.m. (n=3) from one of three independent experiments.*p<0.05, **p<0.01.

FIG. 6A shows peptide pull down assays reveal an increased binding of WDR5 to the phospho-Tyr88-H4 compared to H4 peptide. FIG. 6B shows immunoprecipitation of sheared chromatin from androgen deprived LNCaP cells expressing H4 or Y88F mutant of H4 with FLAG beads followed by immunoblotting with H3K4me3 and H3K9me3 antibodies. FIG. 6C through 6F show ChIP with indicated antibodies, followed by qPCR using primers corresponding to AREM1 and control (gene desert) sites in C4-2B cells treated with (R)-9bMS. Data represent mean±s.e.m. (n=3) from one of three independent experiments. *p<0.05, **p<0.01.

FIG. 7A shows cell viability assay of PC lines treated with (R)-9bMS for 96 hr. Data represent mean±s.e.m. (n=3) from one of three independent experiments. FIG. 7B shows apoptosis assay of C4-2B cells treated with (R)-9bMS, sarcatinib or staurosporine. FIG. 7C shows that after (R)-9bMS or vehicle treatment, the C4-2B xenograft tumors were excised and representative tumors are shown. FIG. 7D shows cell viability assay for the enzalutamide-resistant C4-2B cells treated with (R)-9bMS for 96 hr. Data represent mean±s.e.m. (n=3) from one of three independent experiments. FIG. 7E shows qRT-PCR analysis of AR mRNA levels in enzalutamide-resistant cells. Data represent mean±standard error of the mean (s.e.m.) (n=3) from one of three independent experiments.*p<0.05. FIG. 7F shows immunoblot analysis of enzalutamide-resistant C4-2B cells treated with (R)-9bMS. Cell cycle analysis of prostate cell lines treated with (R)-9bMS (24 hr).

FIG. 8A shows C4-2B cells were implanted subcutaneously in castrated male SCID mice. Once formed palpable tumors, mice were injected with vehicle (10% DMSO in PBS) or (R)-9bMS (50 mg/kg of body) for 6 days a week for five weeks (n=9 mice for each treatment). Tumor volumes were measured. Data represent mean±s.e.m. FIG. 8B shows the weights of the xenograft tumors are shown. *p<0.05. FIG. 8C shows data from when xenografts tumors excised. FIG. 8D shows qRT-PCR analysis of AR, PSA and TMPRSS2 mRNA levels in xenograft tumors treated with DMSO or (R)-9bMS. Data represent mean±standard error of the mean (s.e.m.) (n=3) from one of three independent experiments. **p<0.01. FIG. 8E shows the organs from mice were excised, fixed and H&E stained. FIG. 8F shows the weights of the mice are shown.

FIGS. 10A and 10B show ACK1 knockdown causes significant increase in total splenocytes and lymph node cell count. FIGS. 10C and 10D show loss of ACK1 results in significant increase in CD4 helper, CD8 cytotoxic cells. FIGS. 10E and 10F show a significant increase in spleen and lymph node B cells was observed upon loss of ACK1 activity.

FIGS. 11A and 11B show ACK1 knockdown causes significant increase in natural killer (NK) cell and CD4+CD25+ regulatory T cells (Treg) count. FIG. 11C shows T cells were purified from WT and KO mice and were activated with anti-CD3 for 24 h. T cells were stained for IFN-g production.

DETAILED DESCRIPTION

Figure 2A:
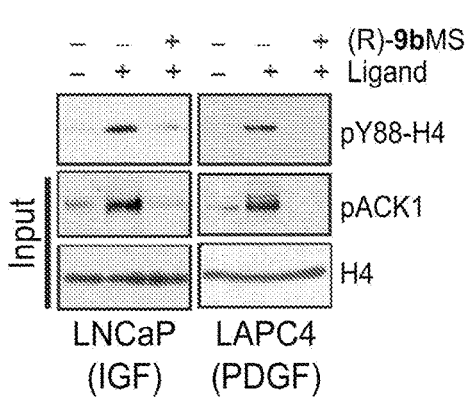
FIG. 2A through 2C. ACK1 inhibitor (R)-9bMS suppresses epigenetic modification of histone H4 at tyrosine 88.

The materials, compounds, compositions, and methods described herein may be understood more readily by reference to the following detailed description of specific aspects of the disclosed subject matter and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an inhibitor" includes mixtures of two or more such inhibitors, reference to "the kinase" includes mixtures of two or more such kinase, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., tumor growth, metastasis). It is understood that this is typically in relation to some standard or expected value, in other words it is relative, but that it is not always necessary for the standard or relative value to be referred to. For example, "reduces tumor growth" means decreasing the amount of tumor cells relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, delaying spread (e.g. metastasis) of the cancer, delaying occurrence or recurrence of cancer, delay or slowing of cancer progression, amelioration of the cancer state, and remission (whether partial or total).

The term "patient" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "heteroalkyl" as used herein is a branched or unbranched saturated hydrocarbon group of 1-24 carbon atoms where one or more of the carbon atoms and its attached hydrogen atoms, if any, have been replaced by a O, S, N, or NH. The heteroalkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The symbols $A''$ is used herein as merely a generic substitutent in the definitions below.

The term "alkoxy" as used herein is an alkyl group bound through a single, terminal ether linkage; that is, an "alkoxy" group can be defined as $-OA^1$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl and heteroaryl group can be substituted or unsubstituted. The aryl and heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "heterocycloalkyl" is a type of cycloalkyl group as defined above where at least one of the carbon atoms and its attached hydrogen atoms, if any, are replaced by O, S, N, or NH. The heterocycloalkyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with O, S, N, or NH. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for C=O.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula —C(O)O−.

The term "ester" as used herein is represented by the formula —OC(O)$A^1$ or —C(O)O$A^1$, where $A^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $A^1C(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula —$NO_2$.

The term "cyano" as used herein is represented by the formula —CN

The term "azido" as used herein is represented by the formula —$N_3$.

The term "sulfonyl" is used herein to refer to the sulfo-oxo group represented by the formula —$S(O)_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —$S(O)_2NH_2$.

The term "thiol" as used herein is represented by the formula —SH.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Reference will now be made in detail to specific aspects of the disclosed materials, compounds, compositions, articles, and methods, examples of which are illustrated in the accompanying Examples.

Compounds

It has been found that ACK1 directly phosphorylates AKT at Tyr176 resulting in AKT membrane localization and activation. In prostate cancer cells ACK1 phosphorylates AR at Tyr-267 in an androgen-independent manner. In addition, Tyr284-phosphorylated-ACK1, Tyr176-phosphorylated-AKT and Tyr267-phosphorylated-AR levels were positively correlated with the severity of disease progression, and inversely correlated with the survival of prostate cancer patients. Similarly, ACK1 mediated AKT tyrosine phosphorylation was found to correlate positively with breast cancer progression.

Further, it has been found that an inhibitor of ACK1, 4-amino-5,6-biaryl-furo[2,3-d]pyrimidine (AIM-100) not only inhibited ACK1 activation but suppresses pTyr267-AR phosphorylation and AKT Tyr176-phosphorylation, inhibiting AR and AKT activity. These findings indicate that ACK1 is prognostic of progression of prostate cancer and inhibitors of ACK1 activity are therapeutic agents to treat prostate cancer.

Focused chemical libraries of ACK1 inhibitors were developed by scaffold-hopping and fragment structure-based design. From the library, several compounds were identified as being capable of inhibiting ACK1 in vitro at low concentrations, and in many cases nanomolar concentrations. Compounds from the library were shown to inhibit, in intact cancer cells, the phosphorylation of AKT at Tyr176, a surrogate for ACK1 inhibition in vivo.

Thus, disclosed are compounds that are ACK1 tyrosine kinase inhibitors. These disclosed compounds can be used in various compositions as anti-cancer therapeutics.

In certain embodiments, the disclosed compounds have a pyrimidine based structure as shown in Formula I.

wherein
n is 1, 2, or 3;
m is 1, 2, 3, 4, or 5, preferably m is 1 or 2; and
$R^1$ is $C_5$-$C_6$ cycloalkyl, $C_4$-$C_6$ heterocycloalkyl, phenyl, or pyrimidinyl, any of which can be unsubstituted or substituted with $R^6$;
each $R^2$ is, independently, Cl, Br, F, $C_1$-$C_6$ alkyl, $C_1$-$C_6$ alkoxyl, $CH_2C(O)R^5$, $C(O)NHR^5$, or a heterocycloalkyl that is unsubstituted or substituted with $R^6$, where
$R^5$ is $C_1$-$C_6$ alkyl, heteroalkyl, cycloalkyl, heterocycloalkyl, or heteroaryl, any of which can be unsubstituted or substituted with $R^6$; and
$R^6$ is OH, Cl, Br, F, $C_1$-$C_6$ alkyl, $CO_2H$, $CO_2R^5$, $OC(O)R^5$, $(CH_2)_{1-6}CO_2H$, $C(O)(CH_2)_{1-6}CO_2H$, $(CH_2)_{1-6}CO_2R^5$, $C(O)(CH_2)_{1-6}CO_2R^5$, $OR^5$, $C(O)R^5$, $C(O)NH_2$, $C(O)NHR^5$, $SO_2NH_2$, $SO_2NHR^5$, $C(O)NHSO_2R^5$, 4-morpholinyl, 4-piperazinyl, 1-piperidinyl, 4-piperadinyl group.

The disclosed compounds can also exist as pharmaceutically acceptable salts and examples of such salts are disclosed herein.

In certain embodiments, $R^1$ can be $C_4$-$C_6$ heterocycloalkyl group containing at least one oxygen or nitrogen atom, optionally substituted with one or more $R^6$ groups. Exemplary $C_4$-$C_6$ heterocycloalkyl group including furanyl, tetrahydrofuranyl, dihydrofuranyl, pyranyl, oxepanyl and furofuranyl.

In some specific examples, $R^1$ can be cyclopentyl, cyclohexyl, furanyl, tetrahydrofuranyl, pyrrolidinyl, oxane, optionally substituted with $C_1$-$C_6$ alkyl. In some other specific examples, $R^1$ can be phenyl optionally substituted with halide.

In some examples, $R^2$ can be 4-morpholinyl, 4-piperazinyl, 1-piperidinyl, or 4-piperadinyl group that is unsubstituted or substituted with $R^6$, e.g., with a methyl. In a preferred example, $R^2$ can be N-methylpiperazinyl. In other examples with these formula, m can be 1 and $R^2$ is in the para position or m is 2 and each $R^2$ are in the para and meta positions.

Provided herein are compounds of Formula II

II wherein:
n is 1, 2, or 3;
m is 1, 2, 3, 4, or 5, preferably m is 1 or 2;
a is 1, 2 or 3;
b is 0, 1 or 2;
each $R^2$ is, independently, Cl, Br, F, $C_1$-$C_6$ alkyl, $CH_2C(O)R^5$, $C(O)NHR^5$, or a heterocycloalkyl that is unsubstituted or substituted with $R^6$;
$R^6$ when present, is independently OH, Cl, Br, F, $C_1$-$C_6$ alkyl, $CO_2H$, $CO_2R^5$, $OC(O)R^5$, $(CH_2)_{1-6}CO_2H$, $C(O)(CH_2)_{1-6}CO_2H$, $(CH_2)_{1-6}CO_2R^5$, $C(O)(CH_2)_{1-6}CO_2R^5$, $OR^5$, $C(O)R^5$, $C(O)NH_2$, $C(O)NHR^5$, $SO_2NH_2$, $SO_2NHR^5$, $C(O)NHSO_2R^5$, 4-morpholinyl, 4-piperazinyl, 1-piperidinyl, 4-piperadinyl group; and
$R^5$, when present, is $C_1$-$C_6$ alkyl, heteroalkyl, cycloalkyl, heterocycloalkyl, or heteroaryl, any of which can be unsubstituted or substituted with $R^6$;
or a pharmaceutically acceptable salt thereof.

In some embodiments are provided enantioenriched compounds of Formula IIa:

IIa wherein n, m, a, b, $R^2$ and $R^6$ have the meanings given for the compound of Formula II, or a pharmaceutically acceptable salt thereof. The compound of Formula IIa can be provided in an enantiomer excess of at least 90%, at least 95%, at least 96%, at least 97%, at least 98%, at least 99%, or at least 99.5%.

In certain preferred embodiments of the compounds of Formulas II and IIa, a is 1, b is 0, n is 1, m is 1 with $R^2$ at the para position, or m is 2 with $R^2$ (which can be the same or different) at the meta and para position.

In further examples, disclosed are compounds with Formula III:

III wherein n is 1, 2, or 3;

$R^1$ is $C_5$-$C_6$ cycloalkyl, $C_4$-$C_6$ heterocycloalkyl, phenyl, or pyrimidinyl, any of which can be unsubstituted or substituted with $R^6$;

$R^{2'}$ is H, Cl, Br, F, $C_1$-$C_6$ alkyl, $C_1$-$C_6$ alkoxyl, $CH_2C(O)R^5$, $C(O)NHR^5$, or a heterocycloalkyl that is unsubstituted or substituted with $R^6$, where $R^5$ is $C_1$-$C_6$ alkyl, heteroalkyl, cycloalkyl, heterocycloalkyl, or heteroaryl, any of which can be unsubstituted or substituted with $R^6$; and $R^6$ is OH, Cl, Br, F, $C_1$-$C_6$ alkyl, $CO_2H$, $CO_2R^5$, $OC(O)R^5$, $(CH_2)_{1-6}CO_2H$, $C(O)(CH_2)_{1-6}CO_2H$, $(CH_2)_{1-6}CO_2R^5$, $C(O)(CH_2)_{1-6}CO_2R^5$, $OR^5$, $C(O)R^5$, $C(O)NH_2$, $C(O)NHR^5$, $SO_2NH_2$, $SO_2NHR^5$, $C(O)NHSO_2R^5$, 4-morpholinyl, 4-piperazinyl, 1-piperidinyl, 4-piperadinyl group.

In certain embodiments, $R^1$ can be $C_4$-$C_6$ heterocycloalkyl group containing at least one oxygen or nitrogen atom, optionally substituted with one or more $R^6$ groups. Exemplary $C_4$-$C_6$ heterocycloalkyl group including furanyl, tetrahydrofuranyl, dihydrofuranyl, pyranyl, oxepanyl and furofuranyl.

In some specific examples, $R^1$ can be cyclopentyl, cyclohexyl, furanyl, tetrahydrofuranyl, pyrrolidinyl, oxane, optionally substituted with $C_1$-$C_6$ alkyl. In some other specific examples, $R^1$ can be phenyl optionally substituted with halide.

In some specific examples, $R^{2'}$ can be H or OMe.

Suitable compounds according to the present disclosure are provided in Table 1.

| Example, Structure | ACK1 ELISA % inhibition at 10 µM | $IC_{50}$ |
|---|---|---|
| Example 1 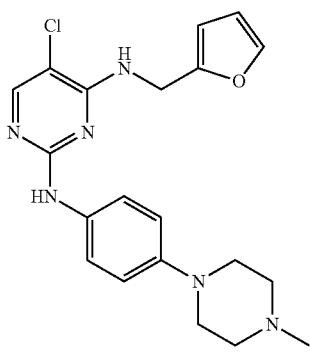 [SMILES: CN1CCN(c2ccc(Nc3ncc(Cl)c(NCc4ccco4)n3)cc2)CC1] | 95.96 | |
| Example 2 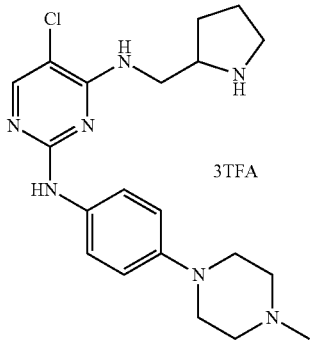 [SMILES: CN1CCN(c2ccc(Nc3ncc(Cl)c(NCC4CCCN4)n3)cc2)CC1] 3TFA | 18.27 | |
| Example 3 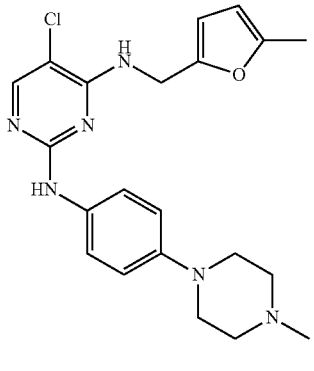 [SMILES: Cc1ccc(CNc2nc(Nc3ccc(N4CCN(C)CC4)cc3)ncc2Cl)o1] | 90.93 | |

-continued
| Example, Structure | ACK1 ELISA % inhibition at 10 μM | IC$_{50}$ |
|---|---|---|
| Example 4 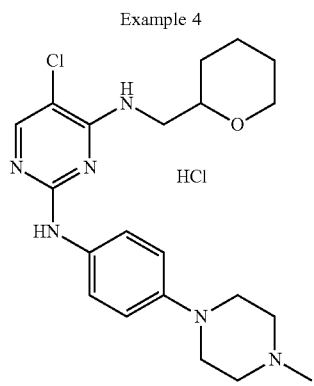 | 96.95 | |
| Example 5 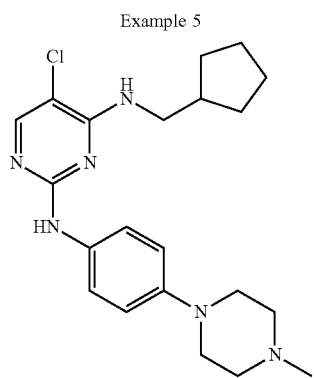 | 96.95 | |
| Example 6 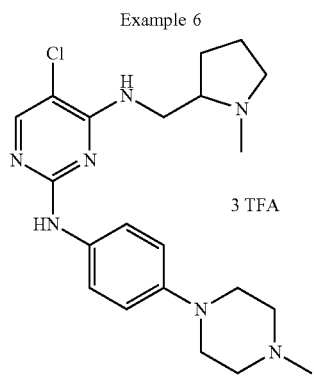 | 35.6 | |
| Example 7 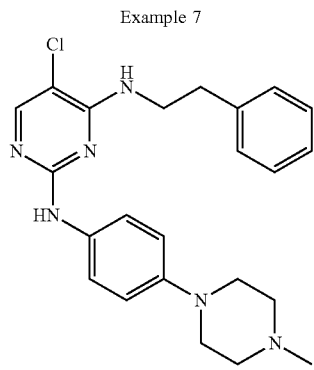 | 91.94 | |

-continued
| Example, Structure | ACK1 ELISA % inhibition at 10 μM | IC$_{50}$ |
|---|---|---|
| Example 8 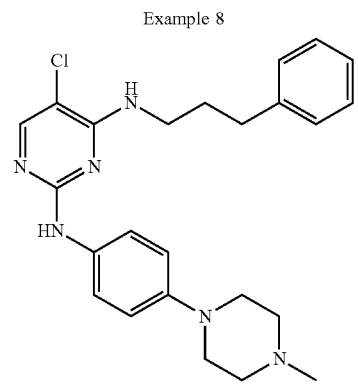 | 85.84 | |
| Example 9 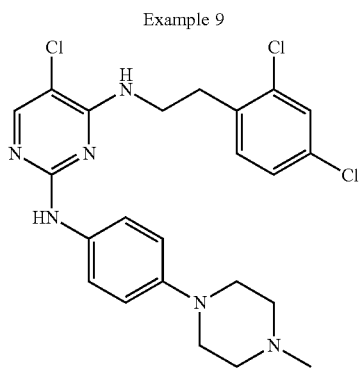 | 36.49 | |
| Example 10 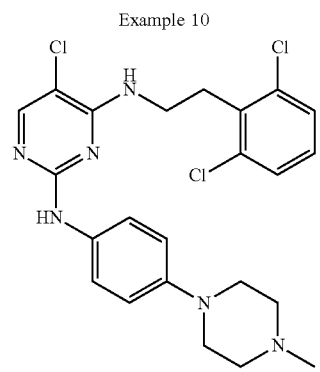 | 96.99 | |
| Example 11 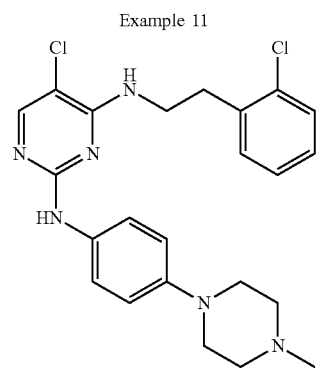 | 90.95 | |

-continued
| Example, Structure | ACK1 ELISA % inhibition at 10 μM | IC$_{50}$ |
|---|---|---|
| Example 12 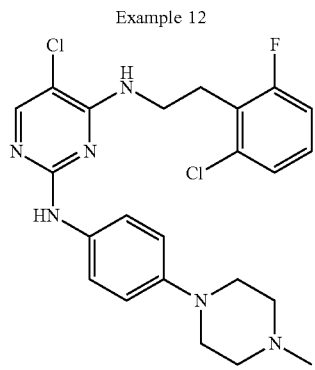 | 92.96 | |
| Example 13 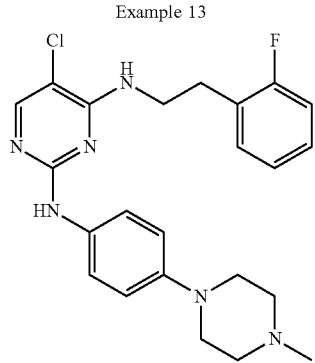 | 91 | |
| Example 14 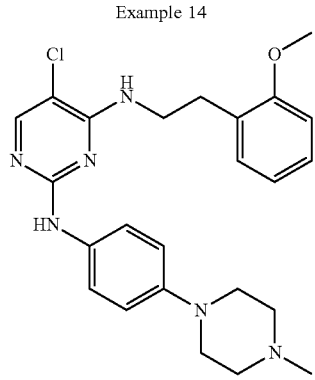 | 97.96 | |
| Example 15 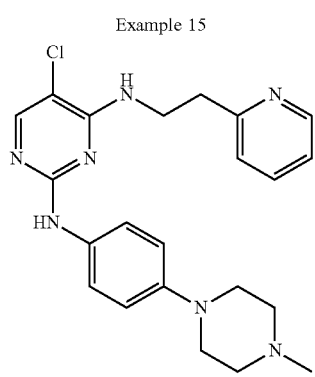 | 91.90 | |

-continued
| Example, Structure | ACK1 ELISA % inhibition at 10 μM | IC$_{50}$ |
|---|---|---|
| Example 16 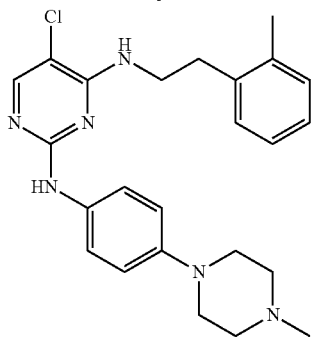 | 90.96 | |
| Example 17 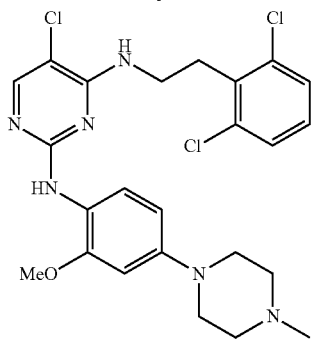 | | |
| Example 18 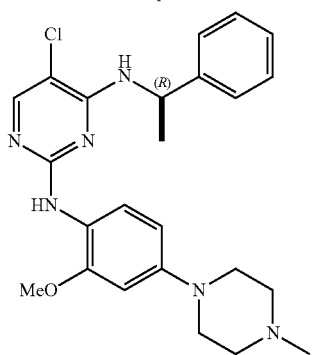 | | |
| Example 19 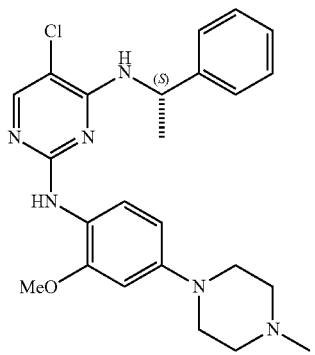 | | |

-continued

| Example, Structure | ACK1 ELISA % inhibition at 10 μM | $IC_{50}$ |
|---|---|---|
| Example 20 | | ACK1 27 nM (RB)<br>JAK2 1721 nM (RB)<br>ALK 7 nM (RB)<br>c-Src 11470 nM (RB) |
| Example 21 | | ACK1 24 nM (RB)<br>JAK2 860 nM (RB)<br>ALK 2 nM (RB)<br>c-Src 8252 nM, (RB) |
| Example 22 | | |
| Example 23 | | |

| Example, Structure | ACK1 ELISA % inhibition at 10 μM | IC$_{50}$ |
|---|---|---|
| Example 24 | 86.82 | |
| Example 25 | 86.87 | |
| Example 26 | | ACK1 39 nM, (RB)<br>JAK2 1076 nM, (RB)<br>ALK 34 nM (RB)<br>c-Src 16750 nM (RB) |

Method

Further provided herein are methods of treating or preventing cancer in a subject, comprising administering to the subject an effective amount of a compound or composition as disclosed herein. The methods can further comprise administering a second compound or composition, such as, for example, anticancer agents or anti-inflammatory agents. Additionally, the method can further comprise administering an effective amount of ionizing radiation to the subject.

Methods of killing a tumor cell are also provided herein. The methods comprise contacting a tumor cell with an effective amount of a compound or composition as disclosed herein. The methods can further include administering a second compound or composition (e.g., an anticancer agent or an anti-inflammatory agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation.

Also disclosed are methods for treating oncological disorders in a patient. In one embodiment, an effective amount of one or more compounds or compositions disclosed herein is administered to a patient having an oncological disorder and who is in need of treatment thereof. The disclosed methods can optionally include identifying a patient who is or can be in need of treatment of an oncological disorder. The patient can be a human or other mammal, such as a primate (monkey, chimpanzee, ape, etc.), dog, cat, cow, pig, or horse, or other animals having an oncological disorder. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Other examples of cancers that can be treated according to the methods disclosed herein are adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma, hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lung cancer, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenstrom's macroglobulinemia, and Wilms' tumor.

In some aspect, disclosed are methods for treating a tumor or tumor metastases in a subject by the administration to the subject a combination of at least one compound or composition as disclosed herein and at least one cancer immunotherapeutic agent. The disclosed compounds can be administered alone or in combination with a cancer immunotherapeutic agent. The subject can receive the therapeutic compositions prior to, during or after surgical intervention to remove all or part of a tumor. Administration may be accomplished via direct immersion; systemic or localized intravenous (i.v.), intraperitoneal (i.p.), subcutaneous (s.c.), intramuscular (i.m.), or direct injection into a tumor mass; and/or by oral administration of the appropriate formulations.

A cancer immunotherapeutic agent suitable for use in the methods disclosed herein is an immunotherapeutic agent which comprises a cell effector component joined to a tumor associated antigen targeting component. Suitable cell effector components can include cytotoxic chemicals, cytotoxic radioisotopes, and cell signaling agents such as cytokines. Suitable tumor targeting components are polypeptide chains which bind to tumor associated antigens present on or in the surrounding tissue matrix of a tumor cell such as receptor protein chains or immunoglobulin chains.

Tumor associated antigens which can be used for targets of the immunotherapeutic agents include a tumor associated antigen selected from the group consisting of AFP, CA 125, CEA, CD19, CD20, CD44, CD45, EGF Receptor, GD[2], GD[3], GM1, GM2, Her-2/Neu, Ep-CAM (KSA), IL-2 receptor, Lewis-Y, Lewis-X (CD 15), melanoma-associated proteoglycan MCSP, PSA and Transferrin Receptor.

Examples of immunotherapeutic agents have an effector component that is a cytokine polypeptide joined to a targeting component which is an immunoglobulin (Ig) polypeptide chain. The Ig polypeptide chain comprises a variable region which binds to a tumor associated antigen. It is preferred that said immunoglobulin chain, when combined with the appropriate complementary chain (i.e. a heavy chain complements a light chain) defines an antibody active site which is specific for a tumor associated antigen.

The tumor targeting Ig portion of the immunotherapeutic agent can comprise an entire immunoglobulin chain amino acid sequence, or at least the fragment of which comprises the antigen binding specificity portion of the protein. Thus, a suitable Ig polypeptide chain will have at least an Ig variable region specific for a tumor associated antigen.

An antibody and polypeptide chains therefrom, suitable for use in the disclosed methods, will have an amino acid sequence that can be of any mammalian origin. Where such antibody protein is not of the same origin as the anticipated patient, fragments of the antibody protein, such as F(ab')2, Fab, Fv or engineered Fv single chain antibody protein can be used. To further reduce antigenicity of the antibody protein, modification of the antibody amino acid sequence may be accomplished to reduce such by making the protein appear more like the patients normal antibody components. For example, monoclonal murine antibody amino acid sequences can be modified to appear more human, for administration to human patients by a variety of processes for humanization of the antibody.

Specific examples of cancer immunotherapeutic agents include an antibody that specifically binds CLTA-4, such as ipilimumab (Bristol-Myers Squibb), anti-PD-1, anti-PDL1. Other immunotherapeutic agents include the TNFα antagonists (e.g. etanercept), the B cell depleting agent rituximab, the anti-IL-6 receptor tocilizumab, and the costimulation blocker abatacept can be administered with the compounds or compositions disclosed herein.

The disclosed compounds can also be administered with toll like receptor (TLR) agonist. TLR agonist is a ligand for a TLR selected from the group consisting of TLR1, TLR2, TLR3, TLR4, and TLR9. For example, the TLR agonist can be a ligand selected from the group consisting of Pam3CSK4, Pam3CSK4, poly I:C, Ribomunyl, and CpG ODN.

The disclosed compounds can also be administered with an angiogenesis inhibiting agent, which is one which can inhibit the formation of new blood vessels (neovascularization) or enlargement of existing capillary networks into the tissues near a tumor cell. Suitable angiogenesis inhibiting agents can be peptides with angiogenesis inhibiting activity, such as the tumor associated antigen PSA. Other suitable angiogenesis inhibiting agents can be antagonists of VEGF associated angiogenesis, for example antagonists of the VEGF receptor on the surface of cells. One monoclonal antibody which can be used is LM609 (ATCC HB 9537).

Administration

The disclosed compounds can be administered either sequentially or simultaneously in separate or combined pharmaceutical formulations. When one or more of the disclosed compounds is used in combination with a second therapeutic agent, the dose of each compound can be either the same as or differ from that when the compound is used alone. Appropriate doses will be readily appreciated by those skilled in the art.

The term "administration" and variants thereof (e.g., "administering" a compound) in reference to a compound as described herein means introducing the compound or a prodrug of the compound into the system of the animal in need of treatment. When a compound as described herein or prodrug thereof is provided in combination with one or more other active agents (e.g., a cytotoxic agent, etc.), "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 2003/0032594 and 2002/0120100 disclose amino acid sequences that can be coupled to another composition and that allows the composition to be translocated across biological membranes. U.S. Application Publication No. 2002/0035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex virus in the treatment of non-small cell lung cancer (Toyoizumi, et al., "Combined therapy with chemotherapeutic agents and herpes simplex virus type IICP34.5 mutant (HSV-1716) in human non-small cell lung cancer," *Human Gene Therapy,* 1999, 10(18):17).

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and U.S. Pat. No. 4,820,508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions disclosed herein can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions disclosed herein can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation; East Hanover, N.J.) and HERCEPTIN (Genentech, Inc.; South San Francisco, Calif.), respectively. These other substances or radiation treatments can be given at the same as or at different times from the compounds disclosed herein. Examples of other suitable chemotherapeutic agents include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafur-uracil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of suitable immunotherapeutic agents include, but are not limited to, alemtuzumab, cetuximab (ERBITUX), gemtuzumab, iodine 131 tositumomab, rituximab, trastuzamab (HERCEPTIN). Cytotoxic agents include, for example, radioactive isotopes (e.g., $I^{131}$, $I^{125}$, $Y^{90}$, $P^{32}$, etc.), and toxins of bacterial, fungal, plant, or animal origin (e.g., ricin, botulinum toxin, anthrax toxin, aflatoxin, jellyfish venoms (e.g., box jellyfish, etc.) Also disclosed are methods for treating an oncological disorder comprising administering an effective amount of a compound and/or agent disclosed herein prior to, subsequent to, and/or in combination with administration of a chemotherapeutic agent, an immunotherapeutic agent, a radiotherapeutic agent, or radiotherapy.

Kits

Kits for practicing the methods described herein are further provided. By "kit" is intended any manufacture (e.g., a package or a container) comprising at least one reagent, e.g., anyone of the compounds described in Table 1. The kit can be promoted, distributed, or sold as a unit for performing the methods described herein. Additionally, the kits can contain a package insert describing the kit and methods for its use. Any or all of the kit reagents can be provided within containers that protect them from the external environment, such as in sealed containers or pouches.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

Method of Screening

Also disclosed herein are methods of identifying a putative anti-cancer compound comprising contacting an ACK1 tyrosine kinase with a target compound and determining whether the compound binds the kinase in a DFG-out configuration, wherein a compound that binds the DFG-out configuration is identified as a putative anti-cancer compound.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in QC or is at ambient temperature, and pressure is at or near atmospheric.

ACK1, Activated CDC42 associated Kinase 1; DMF, Dimethylformamide; DMSO, Dimethylsulfoxide; DCM, Dichloromethane; ELISA, Enzyme-Linked Immunosorbent Assay; ESI, Electrospray Ionization; HRMS, High Resolution Mass Spectroscopy; HPLC, High Performance Liquid Chromatography; HCL, Hydrochloric Acid; LC-MS, Liquid Chromatography Mass Spectrometry; mCPBA, meta-Chloroperoxybenzoic Acid; SAR, Structure Activity Relationship; TFA, Trifluoroacetic Acid; THF, Tetrahydrofuran.

Compound Synthesis

The compounds disclosed herein can be prepared by the following route:

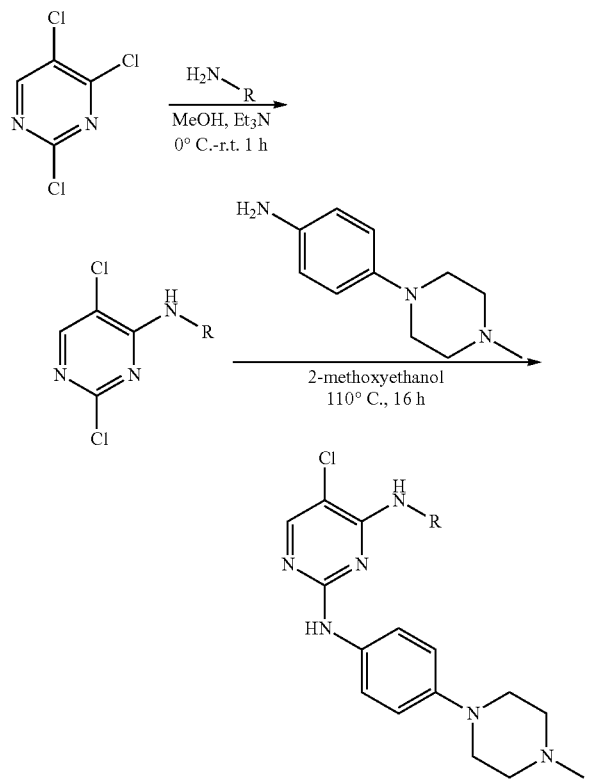

For example, the compounds can be prepared by a route disclosed in WO2015/021149, which is incorporated by reference herein for its synthetic techniques and characterization assays.

Intermediate 1

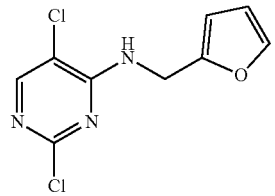 [SMILES: Clc1ncc(Cl)c(NCc2ccco2)n1]

2,5-Dichloro-N-(furan-2-ylmethyl)pyrimidin-4-amine (Int-1)

To a solution of furan-2-ylmethanamine (0.477 g, 4.907 mmol) in MeOH (10 mL) under Argon at 0° C. was added Et$_3$N (0.76 mL, 5.453 mmol). The reaction mixture was stirred at 0° C. for 10 min., followed by addition of 2,4,5-trichloropyrimidine (1.000 g, 5.453 mmol) in MeOH slowly. The reaction mixture was warmed up to r.t. after addition and stirred for 2 h. The solvent was removed and the resulting residue was diluted with EtOAc (50 mL) and washed with water (25 mL), then brine (20 mL). The organic layer was dried over Na$_2$SO$_4$, filtered and concentrated. The crude material was purified by SiO$_2$ flash chromatography to obtain the title compound as a white solid (0.951 g, 72%). $^1$H NMR (400 MHz, CDCl$_3$): δ 8.05 (s, 1H), 7.40 (t, J=0.8 Hz, 1H), 6.36-6.34 (m, 2H), 5.81 (brs, 1H), 4.70 (d, J=5.6 Hz, 2H); LC-MS (ESI+) m/z 244.1 (M+H)$^+$.

Intermediate 2

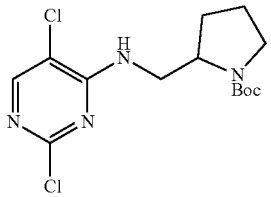 [SMILES: CC(C)(C)OC(=O)N1CCCC1CNc1nc(Cl)ncc1Cl]

tert-Butyl 2-(((2,5-dichloropyrimidin-4-yl)amino) methyl)pyrrolidine-1-carboxylate (Int-2)

This compound was synthesized using the procedure described for Int-1 except using tert-butyl 2-(aminomethyl) pyrrolidine-1-carboxylate (1.037 g, 5.180 mmol). The crude material, yellow oil (1.765 g, 98%) was used in the next step without purification. $^1$H NMR (400 MHz, CDCl$_3$): δ 8.06 (brs, 1H), 7.97 (s, 1H), 4.26 (appt, J=9.6 Hz, 1H), 3.57-3.52 (m, 1H), 3.41-3.33 (m, 3H), 2.10-2.03 (m, 1H), 1.96-1.88 (m, 2H), 1.78-1.71 (m, 2H overlapping with water), 1.47 (s, 9H); LC-MS (ESI+) m/z 347.2 (M+H)$^+$.

Intermediate 3

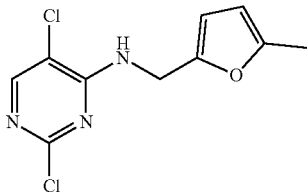 [SMILES: Cc1ccc(CNc2nc(Cl)ncc2Cl)o1]

tert-Butyl 2-(((2,5-dichloropyrimidin-4-yl)amino)
methyl)-5-methyl-1H-pyrrole-1-carboxylate (Int-3)

This compound was synthesized using the procedure described for Int-1 except using (5-methylfuran-2-yl)methanamine (0.576 g, 5.180 mmol). The crude material was triturated with DCM/Hexane to afford the title compound as a white solid. (1.11 g, 85%). $^1$H NMR (400 MHz, CDCl$_3$): δ 8.06 (s, 1H), 6.22 (d, J=2.8 Hz, 1H), 5.93-5.92 (m, 1H), 5.85 (brs, 1H), 4.64 (d, J=5.2 Hz, 2H), 2.28 (s, 3H); LC-MS (ESI+) m/z 258.1 (M+H)$^+$.

Intermediate 4

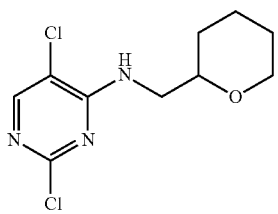 [SMILES: Clc1ncc(Cl)c(NCC2CCCCO2)n1]

2,5-Dichloro-N-((tetrahydro-2H-pyran-2-yl)methyl)
pyrimidin-4-amine (Int-4)

This compound was synthesized using the procedure described for Int-1 except using (tetrahydro-2H-pyran-2-yl)methanamine (0.525 g, 4.558 mmol) to afford the title compound as a white solid (0.923 g, 77%). $^1$H NMR (400 MHz, CDCl$_3$): δ 8.01 (s, 1H), 6.00 (s, 1H), 4.04-4.00 (m, 1H), 3.80 (ddd, J=13.6, 6.8, 2.8 Hz, 1H), 3.53-3.43 (m, 1H), 3.28 (ddd, J=13.6, 8.4, 3.6 Hz, 1H), 1.89-1.85 (m, 1H), 1.66-1.47 (m, 4H overlapping with water peak), 1.39-1.30 (m, 1H); LC-MS (ESI+) m/z 262.1 (M+H)$^+$.

Intermediate 5

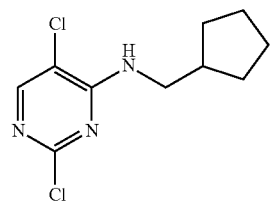 [SMILES: Clc1ncc(Cl)c(NCC2CCCC2)n1]

2,5-Dichloro-N-(cyclopentylmethyl)pyrimidin-4-
amine (Int-5)

This compound was synthesized using the procedure described for Int-1 except using cyclopentylmethanamine (0.186 g, 1.879 mmol) to afford the title compound as a colorless oil (0.337 g, 73%). $^1$H NMR (400 MHz, CDCl$_3$): δ 8.00 (s, 1H), 5.49 (s, 1H), 3.45 (dd, J=7.2, 5.6 Hz, 2H), 2.22-2.14 (m, 1H), 1.86-1.78 (m, 2H), 1.68-1.57 (m, 4H), 1.31-1.23 (m, 2H); LC-MS (ESI+) m/z 246.2 (M+H)$^+$.

Intermediate 6

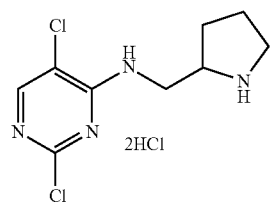 [SMILES: Clc1ncc(Cl)c(NCC2CCCN2)n1]

2,5-Dichloro-N-(pyrrolidin-2-ylmethyl)pyrimidin-4-
amine dihydrochloride salt

A mixture of Int-2 (0.500 g, 1.441 mmol) and 4 M HCl in dioxane (4 mL) was stirred at r.t for 30 min. The solvent was removed and the resulting residue was triturated in DCM/Hex and sonicated. The solvent was decanted. The solid was dried under high vacuum to afford Int-6 as a white solid (0.370 g, 80%). $^1$H NMR (400 MHz, CDCl$_3$): δ 8.16 (s, 1H), 3.84-3.75 (m, 3H), 2.23-2.19 (m, 1H), 2.14-2.02 (m, 2H), 1.88-1.79 (m, 1H); LC-MS (ESI+) m/z 247.1 (M+H)$^+$.

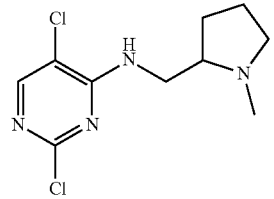 [SMILES: CN1CCCC1CNc1nc(Cl)ncc1Cl]

2,5-Dichloro-N-((1-methylpyrrolidin-2-yl)methyl)
pyrimidin-4-amine (Int-6)

To a suspension of 2,5-dichloro-N-(pyrrolidin-2-ylmethyl)pyrimidin-4-amine dihydrochloride salt (0.160 g, 0.5 mmol) in DMF (2 mL) was added Et$_3$N (0.223 mL, 1.6 mmol), followed by CH$_3$I (0.078 g, 0.55 mmol). The reaction mixture was stirred at r.t. for 4 h. The solvent was removed and water (2 mL) was added to the resulting residue and extracted with DCM (5 mL×6) until the product was completely extracted from the aqueous phase. The combined organic layers was dried over Na$_2$SO$_4$, filtered and concentrated to dryness. The crude material was purified by SiO$_2$ flash chromatography (gradient 0-5% MeOH in DCM) to afford the title compound as a light yellow sticky foaming solid (0.11 g, 84% contained some Et$_3$N HCl salt). This was used without further purification in the next step. $^1$H NMR (400 MHz, CDCl$_3$): δ 10.20 (brs, 1H), 8.11 (s, 1H), 4.17-4.09 (m, 1H), 4.01-3.84 (m, 3H), 2.90-2.82 (m, 1H), 2.80 (s, 3H), 2.45-2.36 (m, 1H), 2.29-2.15 (m, 2H), 2.01-1.95 (m, 1H); LC-MS (ESI+) m/z 261.1 (M+H)⁺.

Intermediate 7

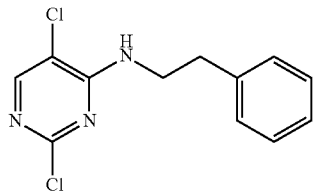 [SMILES: Clc1ncc(Cl)c(NCCc2ccccc2)n1]

2,5-Dichloro-N-phenethylpyrimidin-4-amine (Int-7)

To a solution of phenylethylamine (0.628 g, 5.180 mmol) in MeOH (10 mL) under Argon at 0° C. was added Et₃N (0.76 mL, 5.453 mmol). The reaction mixture was stirred at 0° C. for 10 min., followed by adding solution of 2,4,5-trichloropyrimidine (1.000 g, 5.453 mmol) in MeOH slowly. The reaction mixture was warmed up to r.t. after addition and stirred for 2 h. The solvent was removed and the resulting residue was diluted with EtOAc (50 mL) and washed with water (25 mL), then brine (20 mL). The organic layer was dried (Na₂SO₄), filtered and concentrated to obtain the title compound as an orange liquid (1.290 g, 92.8%). ¹H NMR (400 MHz, CDCl₃): δ 7.98 (s, 1H), 7.35-7.21 (m, 5H), 5.57 (brs, 1H), 3.80-3.75 (m, 2H), 2.95-2.92 (t, J=6.8 Hz, 2H).

Intermediate 8

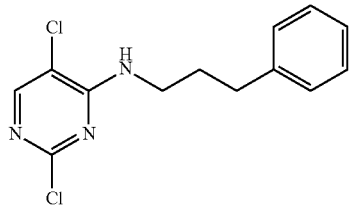 [SMILES: Clc1ncc(Cl)c(NCCCc2ccccc2)n1]

2,5-Dichloro-N-(3-phenylpropyl)pyrimidin-4-amine (Int-8)

This was prepared in the same way as Int-7 using 3-phenylpropylamine (0.700 g, 5.180 mmol) to provide the title compound as a yellow liquid (1.447 g, 99.0%). ¹H NMR (400 MHz, CDCl₃): δ 7.98 (s, 1H), 7.32-7.19 (m, 5H), 5.48 (s, 1H), 3.58-3.53 (m, 2H), 2.74-2.71 (t, J=7.2 Hz, 2H), 2.04-1.96 (m, 2H).

Intermediate 9

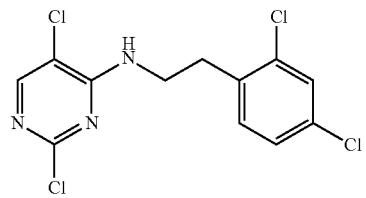 [SMILES: Clc1ccc(CCNc2nc(Cl)ncc2Cl)c(Cl)c1]

2,5-Dichloro-N-(2,4-dichlorophenethyl)pyrimidin-4-amine (Int-9)

This was prepared in the same way as Int-7 using 2,4-dichlorophenethylamine (0.984 g, 5.180 mmol) to provide the title compound as an orange liquid (1.483 g, 85%). ¹H NMR (400 MHz, CDCl₃): δ 8.02 (s, 1H), 7.41 (d, J=2.0 Hz, 1H), dd (7.20, J=8.4, 2.0 Hz, 1H), 7.12 (s, 1H), 7.15 (s, 1H), 5.58 (s, 1H), 3.81-3.76 (m, 2H), 3.08-3.04 (t, J=6.8 Hz, 2H).

Intermediate 10

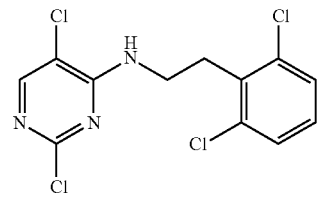 [SMILES: Clc1ncc(Cl)c(NCCc2c(Cl)cccc2Cl)n1]

2,5-Dichloro-N-(2,6-dichlorophenethyl)pyrimidin-4-amine (Int-10)

This was prepared in the same way as Int-7 using 2,6-dichlorophenethylamine (0.984 g, 5.180 mmol) to provide the title compound as an orange liquid (1.097 g, 63%). ¹H NMR (400 MHz, DMSO): δ 9.83 (brs, 1H), 8.14 (brt, J=6.0 Hz, 1H, partially overlapped with the singlet), 8.12 (s, 1H), 7.40 (d, J=8.0 Hz, 2H), 7.24 (t, J=8.0 Hz, 2H), 3.65-3.60 (m, 2H), 3.18-3.14 (t, J=6.8 Hz, 2H).

Intermediate 11

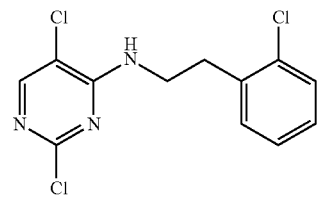 [SMILES: Clc1ncc(Cl)c(NCCc2ccccc2Cl)n1]

2,5-Dichloro-N-(2-chlorophenethyl)pyrimidin-4-amine (Int-11)

This was prepared in the same way as Int-7 using 2-chlorophenylethylamine (0.806 g, 5.180 mmol) to provide the title compound as a white powder (0.700 g, 45%). ¹H NMR (400 MHz, CD3OD): δ 7.98 (s, 1H), 7.36-7.34 (m, 1H), 7.28-7.26 (m, 1H), 7.22-7.17 (m, 2H), 3.74 (t, J=6.8 Hz, 2H), 3.07 (t, J=8.0 Hz, 2H).

Intermediate 12

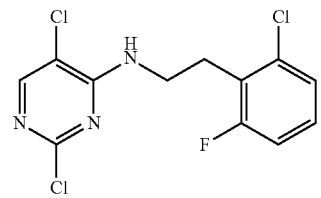 [SMILES: Fc1cccc(Cl)c1CCNc1nc(Cl)ncc1Cl]

2,5-Dichloro-N-(2-chloro-6-fluorophenethyl)pyrimidin-4-amine (Int-12)

This was prepared in the same way as Int-7 using 2-fluoro-6-chlorophenylethylamine (0.984 g, 5.180 mmol) to provide the title compound as a white powder (0.972 g, 59%). $^1$H NMR (400 MHz, CD3OD): δ 7.98 (s, 1H), 7.20-7.18 (m, 2H), 7.03-6.99 (m, 1H), 3.775 (t, J=6.8 HZ, 2H), 3.14 (dt, J=2.0 Hz, 6.4 Hz, 2H).

Intermediate 13

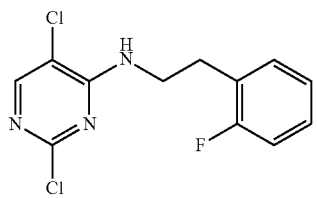 [SMILES: Fc1ccccc1CCNc1nc(Cl)ncc1Cl]

2,5-Dichloro-N-(2-fluorophenethyl)pyrimidin-4-amine (Int-13)

This was prepared in the same way as Int-7 using 2-fluorophenylethylamine (0.721 g, 5.180 mmol) to provide the title compound as a white powder (1.102 g, 74%). $^1$H NMR (400 MHz, CD3OD): δ 7.97 (s, 1H), 7.25-7.19 (m, 2H), 7.08-7.00 (m, 2H), 3.72 (t, J=6.8 Hz, 2H), 2.96 (t, J=6.8 Hz, 2H).

Intermediate 14

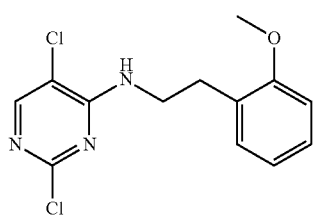 [SMILES: COc1ccccc1CCNc1nc(Cl)ncc1Cl]

2,5-Dichloro-N-(2-methoxyphenethyl)pyrimidin-4-amine (Int-14)

This was prepared in the same way as Int-7 using 2-methoxyphenethylamine (0.783 g, 5.180 mmol) to provide the title compound as a yellow powder (1.350 g, 87%). $^1$H NMR (400 MHz, DMSO): δ 8.10 (s, 1H), 7.86 (t, J=5.6 Hz, 1H), 7.17 (dt, J=1.6 Hz, 7.6 Hz, 1H), 7.09 (dd, J=1.6 Hz, 7.2 Hz, 1H), 6.93 (apptdd, J=1.6 Hz, 7.2 Hz, 1H), 6.83 (dt, J=1.6 Hz, 7.6 Hz, 1H), 3.77 (s, 3H), 3.57-3.62 (m, 2H), 2.852 (t, J=7.6 Hz, 2H).

Intermediate 15

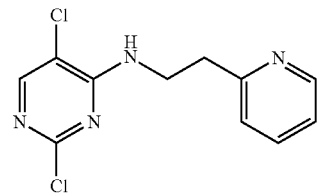 [SMILES: Clc1ncc(Cl)c(NCCc2ccccn2)n1]

2,5-Dichloro-N-(2-(pyridin-2-yl)ethyl)pyrimidin-4-amine (Int-15)

This was prepared in the same way as Int-7 using 2-(2-pyridyl)ethylamine (0.631 g, 5.180 mmol) to provide the title compound as a white solid (1.230 g, 88%). $^1$H NMR (400 MHz, CD3OD): δ 8.44 (ddd, J=0.8, 1.6, 4.8 Hz, 1H), 7.98 (s, 1H), 7.73 (td, J=1.6 Hz, 7.6 Hz, 1H), 7.33 (td, J=0.8, 8 Hz, 1H), 7.25 (ddd, J=1.2, 4.8, 7.6 Hz) 3.83 (t, J=7.2 Hz, 2H), 3.08 (t, J=6.8 Hz, 2H).

Intermediate 16

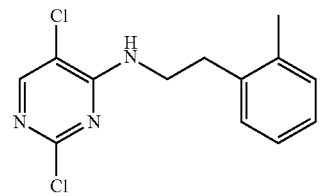 [SMILES: Cc1ccccc1CCNc1nc(Cl)ncc1Cl]

2,5-Dichloro-N-(2-methylphenethyl)pyrimidin-4-amine (Int-16)

This was prepared in the same way as Int-7 using 2-Methylphenylethylamine (0.700 g, 5.179 mmol) to provide the title compound as yellow oil (1.478 g, 96%). This intermediate was used without further purification. $^1$H NMR (400 MHz, CD3OD): δ 7.93 (s, 1H), 7.12-7.03 (m, 4H), 3.61-3.58 (m, 2H), 2.90-2.86 (m, 2H), 2.38 (s, 3H).

Intermediate 17

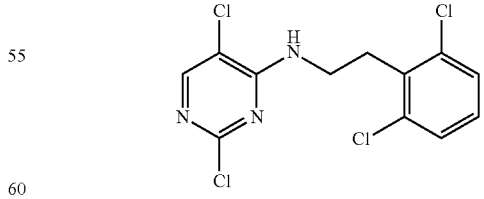

2,5-Dichloro-N-(2,6-dichlorophenethyl)pyrimidin-4-amine (Int-17)

To a solution of 2,6-dichlorophenethylamine (2.07 g, 10.9 mmol) in MeOH (20 mL) was slowly added triethylamine (1.52 mL) at 0° C. To the mixture was then added a solution of 2,4,5-trichloropyrimidine (2.00 g, 10.9 mmol) in MeOH (20 mL). The mixture was stirred for 2.5 hours and then partitioned using EtOAc and water. The aqueous layer was re-extracted from EtOAc. The organic layers were combined and dried (Na$_2$SO$_4$), filtered, and concentrated under reduced pressure. The resulting crude oil was re-triturated using EtOH, EtOAc, and hexanes to give the title compound as a white solid (1.508 g, 41%). Mp: 158-159° C. HPLC-MS (ESI+): m/z 360.0 [20%, (M$^{35}$Cl$^{35}$Cl$^{35}$Cl$^{35}$Cl+Na)$^+$], 358.1 [20%, (M$^{35}$Cl$^{35}$Cl$^{35}$Cl$^{37}$Cl+Na)$^+$], 338.0 [100%, (M$^{35}$Cl$^{35}$Cl$^{35}$Cl+H)$^+$], 336.0 [90%, (M$^{35}$Cl$^{35}$Cl$^{35}$Cl$^{37}$Cl+H)$^+$], 340.0 [50%, (M$^{35}$Cl$^{35}$Cl$^{37}$Cl$^{37}$Cl+H)$^+$]. $^1$H NMR (400 MHz, DMSO-d$_6$): δ 8.13 (t, J=6.5 Hz, 1H, disappeared on D$_2$O shake), 8.12 (s, 1H), 7.40 (d, J=8.0 Hz, 2H), 7.24 (t, J=8.0 Hz, 1H), 3.63 (q, J=6.5 Hz, 2H), 3.16 (t, J=6.5 Hz, 2H).

Intermediate 18

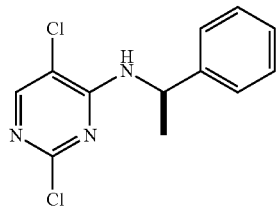 [SMILES: C[C@@H](Nc1nc(Cl)ncc1Cl)c1ccccc1]

(R)-2,5-Dichloro-N-(1-phenylethyl)pyrimidin-4-amine (Int-18)

A mixture of (R)-1-phenylethan-1-amine (1.32 g, 10.9 mmol), 2,4,5-trichloropyrimidine (2 g, 10.9 mmol), and DIPEA in isopropanol (20 mL) was stirred and heated at 80° C. (oil bath) overnight for 19 h. Once removed from heat, the reaction was concentrated under reduced pressure. The resulting oil was dissolved in EtOAc (50 mL) and washed with water (2×30 mL). The aqueous layer was then re-extracted with EtOAc (2×30 mL). The organic layers were combined, dried (Na$_2$SO$_4$), and concentrated under reduced pressure. The crude oil solidified upon standing at room temperature. Hexanes were added and decanted from the flask. Then, hexanes/EtOAc (9:1) was added, which dissolved the solid. The flask was set on ice to allow recrystallization to provide the title compound as a light-tan solid (1.071 g, 37%). Mp: 66-67° C. HPLC-MS (ESI+): m/z 290.0 [25%, (M$^{35}$Cl$^{35}$Cl+Na)$^+$], 270.1 [60%, (M$^{35}$Cl$^{37}$Cl+H)$^+$], 268.1 [100%, (M$^{35}$Cl$^{35}$Cl+H)$^+$]. $^1$H NMR (400 MHz, DMSO-d$_6$): δ 8.19 (d, J=8.1 Hz, 1H, disappeared on D$_2$O shake), 8.16 (s, 1H), 7.38 (d, J=7.5 Hz, 2H), 7.31 (t, J=7.5 Hz, 2H), 7.21 (t, J=7.5 Hz, 1H), 5.28 (pentet, J=7.1 Hz, 1H), 1.52 (d, J=7.1 Hz, 3H).

Intermediate 19

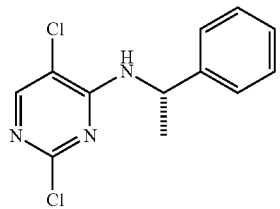 [SMILES: C[C@H](Nc1nc(Cl)ncc1Cl)c1ccccc1]

(S)-2,5-Dichloro-N-(1-phenylethyl)pyrimidin-4-amine (Int-19)

This was prepared in the same way as Int-18 from (S)-1-phenylethan-1-amine (1.32 g, 10.9 mmol). After work-up the resulting yellow oil was purified by flash chromatography (SiO$_2$) eluting with hexanes in EtOAc (0-50%) to provide the title compound as an off-white, crystalline powder (1.638 g, 56%). Mp: 66-67° C. HPLC-MS (ESI+): m/z 290.0 [25%, (M$^{35}$Cl$^{35}$Cl+Na)$^+$], 270.1 [60%, (M$^{35}$Cl$^{37}$Cl+H)$^+$], 268.1 [100%, (M$^{35}$Cl$^{35}$Cl+H)$^+$]. $^1$H NMR (400 MHz, DMSO-d$_6$): δ 8.19 (d, J=8.1 Hz, 1H, disappeared on D$_2$O shake), 8.16 (s, 1H), 7.38 (d, J=7.4 Hz, 2H), 7.31 (t, J=7.4 Hz, 2H), 7.21 (t, J=7.2 Hz, 1H), 5.28 (pentet, J=7.1 Hz, 1H), 1.52 (d, J=7.1 Hz, 3H).

Example 1

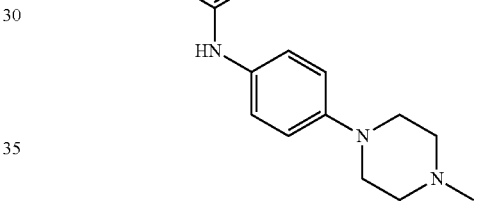

5-Chloro-N4-(furan-2-ylmethyl)-N2-(4-(4-methylpiperazin-1-yl)phenyl)pyrimidine-2,4-diamine (Ex-1)

A mixture of YL11-096 (0.100 g, 0.410 mmol), 4-(4-methylpiperazin-1-yl)aniline (0.086 g, 0.45 mmol) and 4 M HCl in dioxane (0.11 mL, 0.44 mmol) in 2-methoxyethan-1-ol (2 mL) was sealed in a microwave vial and heated in an oil bath at 110° C. for 18 h. The solvent was evaporated using V-10 evaporator upon cooling. The resulting residue was dissolved in saturated NaHCO$_3$ (10 mL) and extracted with chloroform (20 mL×2). The combined organic phase was dried over Na$_2$SO$_4$, filtered and concentrated to dryness. The crude solid was purified by SiO$_2$ flash chromatography. The solid obtained triturated with DCM/Hex to afford the title compound was a white solid (0.11 g, 67%). HPLC 99.4% (t$_R$=9.52 min, 30% CH$_3$OH in 0.1% TFA water, 20 min); $^1$H NMR (400 MHz, CDOD$_3$): δ 7.79 (s, 1H), 7.45-7.41 (m, 3H), 6.92 (appd, J=8.8 Hz, 2H), 6.31 (dd, J=3.2, 2.0 Hz, 1H), 6.18 (dd, J=3.0, 0.8 Hz, 1H), 4.63 (s, 2H), 3.13 (t, J=5.2 Hz, 4H), 2.62 (t, J=5.2 Hz, 4H), 2.34 (s, 3H); LC-MS (ESI+) m/z 200.2 (M+2H)$^{2+}$, 399.2 (M+H)$^+$; HRMS (ESI+) m/z calculated for C$_{20}$H$_{24}$ClN$_6$O (M+H)$^+$ 398.1616, found 398.1597.

Example 2

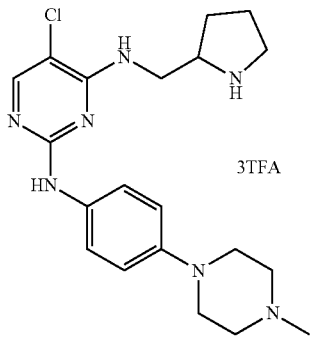 [SMILES: CN1CCN(c2ccc(Nc3ncc(Cl)c(NCC4CCCN4)n3)cc2)CC1]

5-Chloro-N2-(4-(4-methylpiperazin-1-yl)phenyl)-
N4-(pyrrolidin-2-ylmethyl)pyrimidine-2,4-diamine
tri-TFA salt (Ex-2)

This compound was synthesized using the procedure described for Ex-1 except using Int-2 (0.178 g, 0.515 mmol), 4-(4-methylpiperazin-1-yl)aniline (0.093 g, 0.489 mmol) and 4 M HCl in dioxane (0.122 mL, 0.489 mmol) in 2-methoxyethan-1-ol (3 mL). The crude material was purified by prep-HPLC (Gradient MeOH in 0.1% TFA water 15-65%, 30 min) to afford the title compound as a light purple color solid (0.098 g, 27%). HPLC 96% ($t_R$=12.97 min, Gradient CH$_3$OH in 0.1% TFA water 15-65, 30 min); $^1$H NMR (400 MHz, CDOD$_3$): δ 7.95 (s, 1H), 7.39 (d, J=8.8 Hz, 2H), 7.11 (d, J=8.8 Hz, 2H), 3.90-3.71 (m, 6H), 3.63 (d, J=10.8 Hz, 2H), 3.28-3.25 (m, 3H), 3.09-3.03 (m, 2H), 2.98 (s, 3H), 2.16-1.97 (m, 3H), 1.85-1.75 (m, 1H); LC-MS (ESI+) m/z 201.7 (M+2H)$^{2+}$, 402.3 (M+H)$^+$; HRMS (ESI+) m/z calculated for C$_{20}$H$_{29}$ClN$_7$ (M+H)$^+$ 402.2168, found 402.2163.

Example 3

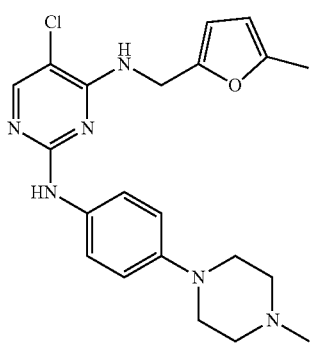 [SMILES: Cc1ccc(CNc2nc(Nc3ccc(N4CCN(C)CC4)cc3)ncc2Cl)o1]

5-Chloro-N4-((5-methylfuran-2-yl)methyl)-N2-(4-
(4-methylpiperazin-1-yl)phenyl)-pyrimidine-2,4-
diamine (Ex-3)

This compound was synthesized using the procedure described for Ex-1 except using Int-3 (0.065 g, 0.250 mmol), 4-(4-methylpiperazin-1-yl)aniline (0.045 g, 0.237 mmol) and 4 M HCl in dioxane (0.063 mL, 0.250 mmol) in 2-methoxyethan-1-ol (2 mL) to afford the title compound as a white color solid (0.069 g, 70%). HPLC 93% ($t_R$=20.53 min, 30% CH$_3$OH in 0.1% TFA water, 30 min); $^1$H NMR (400 MHz, CDOD$_3$): δ 7.78 (s, 1H), 7.45 (d, J=9.2 Hz, 2H), 6.92 (d, J=9.2 Hz, 2H), 6.05 (d, J=3.2 Hz, 1H), 5.89 (dd, J=3.2, 1.2 Hz, 1H), 4.57 (s, 2H), 3.14 (t, J=4.8 Hz, 4H), 2.63 (t, J=4.8 Hz, 4H), 2.35 (s, 3H), 2.24 (s, 3H); LC-MS (ESI+) m/z 207.2 (M+2H)$^{2+}$, 413.3 (M+H)$^+$; HRMS (ESI+) m/z calculated for C$_{21}$H$_{26}$ClN$_6$O (M+H)$^+$ 412.1773, found 412.1767.

Example 4

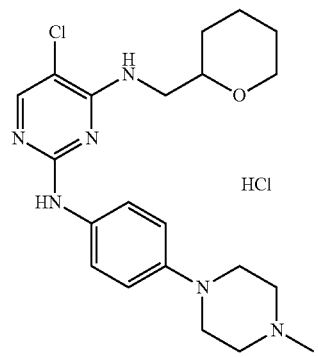 [SMILES: CN1CCN(c2ccc(Nc3ncc(Cl)c(NCC4CCCCO4)n3)cc2)CC1 ; Cl]

5-Chloro-N2-(4-(4-methylpiperazin-1-yl)phenyl)-
N4-((tetrahydro-2H-pyran-2-yl)methyl)pyrimidine-
2,4-diamine hydrochloride (Ex-4)

This compound was synthesized using the procedure described for Ex-1 except using Int-4 (0.100 g, 0.382 mmol), 4-(4-methylpiperazin-1-yl)aniline (0.066 g, 0.344 mmol) and 4 M HCl in dioxane (0.086 mL, 0.344 mmol) in 2-methoxyethan-1-ol (2 mL). The solvent was removed and the resulting residue was slurried with DCM (5 mL), filtered and washed with DCM (3 mL×2), dried under high vacuum to afford the title compound as a grey solid (0.133 g, 85%). HPLC 99% ($t_R$=13.69 min, 30% CH$_3$OH in 0.1% TFA water, 20 min); $^1$H NMR (400 MHz, CDOD$_3$): δ 7.88 (s, 1H), 7.40 (d, J=8.8 Hz, 2H), 7.11 (d, J=9.2 Hz, 2H), 3.96-3.86 (m, 3H), 3.66-3.36 (m, 8H), 3.08 (t, J=11.2 Hz, 2H), 2.98 (s, 3H), 1.87-1.85 (m, 1H), 1.59-1.49 (m, 4H), 1.30-1.22 (m, 1H); LC-MS (ESI+) m/z 209.2 (M+2H)$^{2+}$, 417.3 (M+H)$^+$; HRMS (ESI+) m/z calculated for C$_{21}$H$_{30}$ClN$_6$O (M+H)$^+$ 417.2164, found 417.2164.

Example 5

YL11-143

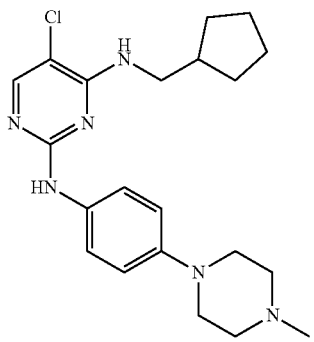 [SMILES: CN1CCN(c2ccc(Nc3ncc(Cl)c(NCC4CCCC4)n3)cc2)CC1]

5-Chloro-N4-(cyclopentylmethyl)-N2-(4-(4-methyl-piperazin-1-yl)phenyl)pyrimidine-2,4-diamine (Ex-5)

This compound was synthesized using the procedure described for Ex-1 excepting using Int-5 (0.105 g, 0.427 mmol), 4-(4-methylpiperazin-1-yl)aniline (0.073 g, 0.384 mmol) and 4 M HCl in dioxane (0.096 mL, 0.384 mmol) in 2-methoxyethan-1-ol (2 mL) to afford the title compound as a beige solid (0.090 g, 59%). HPLC 99.6% ($t_R$=5.04 min, 30% CH$_3$OH in 0.1% TFA water, 20 min); $^1$H NMR (400 MHz, CDOD$_3$): δ 7.85 (s, 1H), 7.47 (d, J=8.8 Hz, 2H), 6.90 (d, J=8.8 Hz, 2H), 6.76 (s, 1H), 5.29 (appt, J=5.6 Hz, 1H), 3.41 (dd, J=7.2, 5.6 Hz, 2H), 3.32 (appt, 4H), 2.87 (brs, 4H), 2.55 (s, 3H), 2.26-2.18 (m, 1H), 1.85-1.78 (m, 2H), 1.68-1.56 (m, 5H), 1.32-1.26 (m, 2H); LC-MS (ESI+) m/z 201.2 (M+2H)$^{2+}$, 401.3 (M+H)$^+$; HRMS (ESI+) m/z calculated for C$_{21}$H$_{30}$ClN$_6$ (M+H)$^+$ 401.2215, found 401.2210.

Example 6

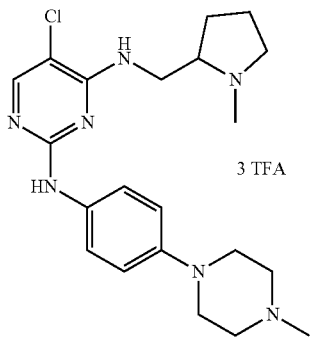 [SMILES: CN1CCN(c2ccc(Nc3ncc(Cl)c(NCC4CCCN4C)n3)cc2)CC1]

3 TFA

5-Chloro-N2-(4-(4-methylpiperazin-1-yl)phenyl)-N4-((1-methylpyrrolidin-2-yl)methyl)pyrimidine-2,4-diamine tri TFA salt (Ex-6)

This compound was synthesized using procedure described for Ex-1 except using Int-6 (0.050 g, 0.192 mmol), 4-(4-methylpiperazin-1-yl)aniline (0.033 g, 0.172 mmol) and 4 M HCl in dioxane (0.043 mL, 0.172 mmol) in 2-methoxyethan-1-ol (1 mL). The crude material was purified by prep-HPLC (Gradient MeOH in 0.1% TFA water 5-65%, 30 min) to afford the title compound as a light brown color solid (0.068 g, 52%). HPLC 99% ($t_R$=9.47 min, Gradient CH$_3$OH in 0.1% TFA water 5-65, 30 min); $^1$H NMR (400 MHz, CDOD$_3$): δ 7.98 (s, 1H), 7.36 (appd, J=8.8 Hz, 2H), 7.12 (appd, J=8.8 Hz, 2H), 3.87 (appd, J=4.8 Hz, 4H), 3.70-3.55 (m, 4H), 3.30-3.24 (m, 2H), 3.13-3.06 (m, 3H), 2.98 (s, 3H), 2.79 (s, 3H), 2.26-2.19 (m, 1H), 2.12-1.87 (m, 3H); LC-MS (ESI+) m/z 208.8 (M+2H)$^{2+}$, 416.3 (M+H)$^+$; HRMS (ESI+) m/z calculated for C$_{21}$H$_{31}$ClN$_7$ (M+H)$^+$ 416.2324, found 416.2318.

Example 7

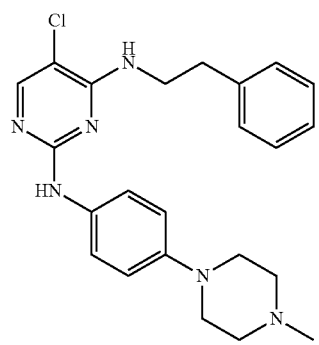

5-chloro-N2-(4-(4-methylpiperazin-1-yl)phenyl)-N4-phenethylpyrimidine-2,4-diamine (Ex-7)

A mixture of Int-7 (0.100 g, 0.37 mmol), 4-(4-methylpiperazin-1-yl)aniline (0.064 g, 0.33 mmol) and 4M HCl in dioxane (0.08 mL, 0.33 mmol) in 2-methoxyethan-1-ol (2 mL) was sealed in microwave vial and heated in an oil bath at 110° C. for 18 h. The solvent was evaporated using a V-10 evaporator upon cooling. The resulting residue was dissolved in saturated NaHCO$_3$ (10 mL) and extracted with chloroform (20 mL×2). The combined organic phase was dried over Na$_2$SO$_4$, filtered and concentrated to dryness. The solid obtained was triturated with DCM and hexane, filtered, and washed with methanol to yield the title compound as a white solid (0.081 g, 57%). HPLC 98% ($t_R$=7.89 min, 40% CH$_3$OH in 0.1% TFA water, 20 min); HPLC-MS (ESI+) m/z 423 (M+H)$^+$; LC-MS (ESI+) m/z 423 (M+H)$^+$.

Example 8

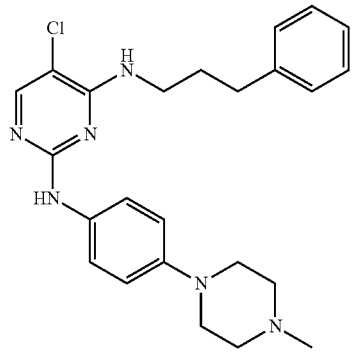 [SMILES: CN1CCN(c2ccc(Nc3ncc(Cl)c(NCCCc4ccccc4)n3)cc2)CC1]

5-Chloro-N2-(4-(4-methylpiperazin-1-yl)phenyl)-N4-(3-phenylpropyl)pyrimidine-2,4-diamine (Ex-8)

This was prepared from Int-8 (0.100 g, 0.35 mmol), 4-(4-methylpiperazin-1-yl)aniline (0.061 g, 0.32 mmol) and 4 M HCl in dioxane (0.1 mL, 0.32 mmol) in the same way as Ex-7 to provide the title compound as a white solid (0.041 g, 30%). HPLC 96% ($t_R$=13.01 min, 40% CH$_3$OH in 0.1% TFA water, 20 min); HPLC-MS (ESI+) m/z 437 (M+H)$^+$; LC-MS (ESI+) m/z 437 (M+H)$^+$.

Example 9

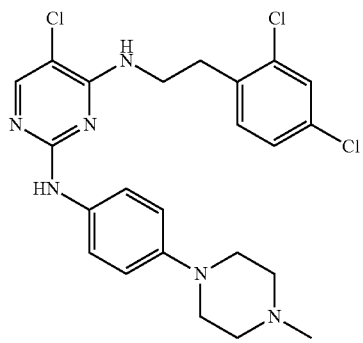 [SMILES: CN1CCN(c2ccc(Nc3ncc(Cl)c(NCCc4ccc(Cl)cc4Cl)n3)cc2)CC1]

5-Chloro-N4-(2,4-dichlorophenethyl)-N2-(4-(4-methylpiperazin-1-yl)phenyl)pyrimidine-2,4-diamine (Ex-9)

This was prepared from Int-9 (0.100 g, 0.30 mmol), 4-(4-methylpiperazin-1-yl)aniline (0.051 g, 0.27 mmol) and 4 M HCl in dioxane (0.07 mL, 0.27 mmol) in the same way as Ex-7 to provide the title compound (0.073 g, 55%). HPLC 95% ($t_R$=3.90 min, 40% CH$_3$OH in 0.1% TFA water, 20 min); HPLC-MS (ESI+) m/z 491 and 493 (M+H)$^+$—Cl isotope; LC-MS (ESI+) m/z 491 (M+H)$^+$.

Example 10

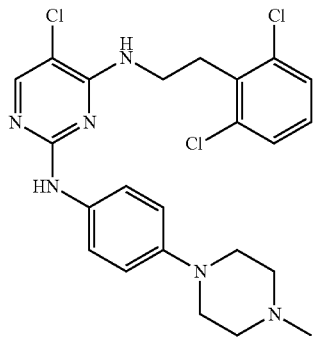 [SMILES: CN1CCN(c2ccc(Nc3ncc(Cl)c(NCCc4c(Cl)cccc4Cl)n3)cc2)CC1]

5-Chloro-N4-(2,6-dichlorophenethyl)-N2-(4-(4-methylpiperazin-1-yl)phenyl)pyrimidine-2,4-diamine (Ex-10)

This was prepared from Int-10 (0.100 g, 0.30 mmol), 4-(4-methylpiperazin-1-yl)aniline (0.051 g, 0.27 mmol) and 4M HCl in dioxane (0.07 mL, 0.27 mmol) in the same way as Ex-7 to provide a crude solid which was purified by SiO$_2$ flash chromatography. The white solid was triturated with DCM/Hex to afford the titled compound (0.070 g, 54%). HPLC 95% ($t_R$=8.6 min, 45% CH$_3$OH in 0.1% TFA water, 20 min); HPLC-MS (ESI+) m/z 491 and 493 (M+H)$^+$—Cl isotope; LC-MS (ESI+) m/z 491 (M+H)$^+$.

Example 11

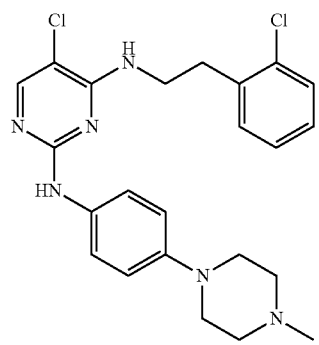 [SMILES: CN1CCN(c2ccc(Nc3ncc(Cl)c(NCCc4ccccc4Cl)n3)cc2)CC1]

5-Chloro-N4-(2-chlorophenethyl)-N2-(4-(4-methylpiperazin-1-yl)phenyl)pyrimidine-2,4-diamine (Ex-11)

This was prepared from Int-11 (0.100 g, 0.33 mmol), 4-(4-methylpiperazin-1-yl)aniline (0.060 g, 0.31 mmol) and 4 M HCl in dioxane (0.08 mL, 0.31 mmol) in the same way as Ex-7 to provide crude material which was purified by flash chromatography. The white solid obtained was triturated with DCM/Hex to afford the titled compound (0.080 g, 56%). HPLC 96% ($t_R$=13.6 min, 45% CH$_3$OH in 0.1% TFA water, 20 min); HPLC-MS (ESI+) m/z 457 and 459 (M+H)$^+$—Cl isotopes; LC-MS (ESI+) m/z 457 (M+H)$^+$; HRMS (ESI+) m/z calculated for C$_{23}$H$_{26}$Cl$_2$N$_6$(M+H)$^+$ 457.1669, found 457.1649.

Example 12

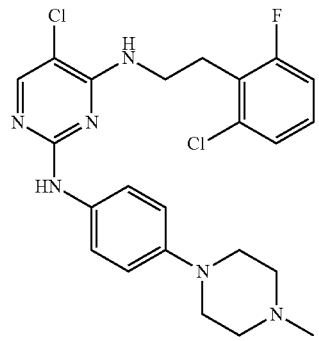 [SMILES: CN1CCN(c2ccc(Nc3ncc(Cl)c(NCCc4c(F)cccc4Cl)n3)cc2)CC1]

5-Chloro-N4-(2-chloro-6-fluorophenethyl)-N2-(4-(4-methylpiperazin-1-yl)phenyl)pyrimidine-2,4-diamine (Ex-12)

This compound was synthesized using the procedure described for Ex-1 using Int-12 (0.648 g, 2.031 mmol), 4-(4-methylpiperazin-1-yl)aniline (0.369 g, 1.930 mmol) and 4 M HCl in dioxane (0.508 mL, 2.031 mmol) in 2-methoxyethan-1-ol (10 mL) to afford the title compound as a white solid (0.641 g, 70%). HPLC 99.9% ($t_R$=11.91 min, 40% $CH_3OH$ in 0.1% TFA water, 40 min); $^1H$ NMR (400 MHz, $CDOD_3$): δ 7.72 (s, 1H), 7.43 (appd, J=9.2 Hz, 2H), 7.21-7.14 (m, 2H), 7.00-6.93 (m, 3H), 3.77 (t, J=6.8 Hz, 2H), 3.16-3.12 (m, 6H), 2.64 (t, J=5.2 Hz, 4H), 2.36 (s, 3H); LC-MS (ESI+) m/z 238.2 $(M+2H)^{2+}$, 475.2 $(M+H)^+$; HRMS (ESI+) m/z calculated for $C_{23}H_{26}Cl_2FN_6$ $(M+H)^+$ 475.1575, found 475.1569.

Example 13

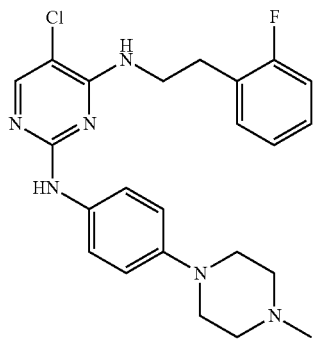

5-Chloro-N4-(2-fluorophenethyl)-N2-(4-(4-methyl-piperazin-1-yl)phenyl)pyrimidine-2,4-diamine (Ex-13)

This was prepared from Int-13 (0.100 g, 0.35 mmol), 4-(4-methylpiperazin-1-yl)aniline (0.063 g, 0.33 mmol) and 4 M HCl in dioxane (0.08 mL, 0.33 mmol) in the same way as Ex-7 to provide crude material which was purified by flash chromatography. The white solid obtained was triturated with DCM/Hex to afford the title compound (0.089 g, 56%). HPLC 93% ($t_R$=13.6 min, 45% $CH_3OH$ in 0.1% TFA water, 20 min); HPLC-MS (ESI+) m/z 441 (M+H); LC-MS (ESI+) m/z 441 $(M+H)^+$; HRMS (ESI+) m/z calculated for $C_{23}H_{26}ClFN_6$ $(M+H)^+$ 441.1964, found 441.1953.

Example 14

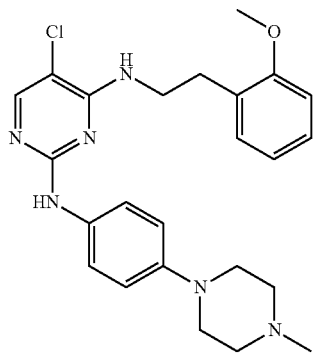 [SMILES: COc1ccccc1CCNc1nc(Nc2ccc(N3CCN(C)CC3)cc2)ncc1Cl]

5-Chloro-N4-(2-methoxyphenethyl)-N2-(4-(4-methylpiperazin-1-yl)phenyl)pyrimidine-2,4-diamine (Ex-14)

This compound was synthesized according to the procedure for Ex-1 using Int-14 (1.180 g, 3.957 mmol), 4-(4-methylpiperazin-1-yl)aniline (0.719 g, 3.760 mmol) and 4 M HCl in dioxane (0.989 mL, 3.957 mmol) in 2-methoxyethan-1-ol (15 mL) to afford the title compound as a white solid (0.777 g, 46%). HPLC 99.6% ($t_R$=11.65 min, 40% $CH_3OH$ in 0.1% TFA water, 40 min); $^1H$ NMR (400 MHz, $CDOD_3$): δ 7.73 (s, 1H), 7.49 (appd, J=8.8 Hz, 2H), 7.18 (ddd, J=8.4, 7.6, 2.0 Hz, 1H), 7.11 (d, J=7.6, 2.0 Hz, 1H), 6.93-6.84 (m, 4H), 3.79 (s, 2H), 3.67 (t, J=7.2 Hz, 2H), 3.14 (t, J=5.2 Hz, 4H), 2.93 (t, J=7.2 Hz, 2H), 2.63 (t, J=4.8 Hz, 4H), 2.35 (s, 3H); LC-MS (ESI+) m/z 227.2 $(M+2H)^{2+}$, 453.3 $(M+H)^+$; HRMS (ESI+) m/z calculated for $C_{24}H_{30}ClN_6O$ $(M+H)^+$ 453.2164, found 453.2169.

Example 15

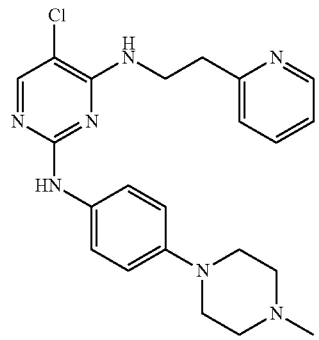 [SMILES: CN1CCN(c2ccc(Nc3ncc(Cl)c(NCCc4ccccn4)n3)cc2)CC1]

5-Chloro-N2-(4-(4-methylpiperazin-1-yl)phenyl)-N4-(2-(pyridin-2-yl)ethyl)pyrimidine-2,4-diamine (Ex-15)

This was prepared from Int-15 (0.100 g, 0.35 mmol), 4-(4-methylpiperazin-1-yl)aniline (0.064 g, 0.33 mmol) and 4 M HCl in dioxane (0.08 mL, 0.33 mmol) in the same way as Ex-7 to provide crude material which was purified by $SiO_2$ flash chromatography. The tan solid obtained was triturated with DCM/Hex to afford the titled compound (0.090 g, 60%). HPLC 99% ($t_R$=13.7 min, 15% $CH_3OH$ in 0.1% TFA water, 20 min); HPLC-MS (ESI+) m/z 424 (M+H); LC-MS (ESI+) m/z 424 $(M+H)^+$; HRMS (ESI+) m/z calculated for $C_{22}H_{26}ClN_7$ $(M+H)^+$ 424.2011, found 424.2005.

Example 16

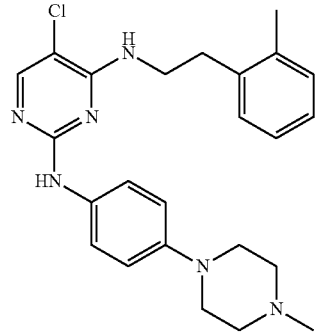 [SMILES: Cc1ccccc1CCNc1nc(Nc2ccc(N3CCN(C)CC3)cc2)ncc1Cl]

5-Chloro-N4-(2-methylphenethyl)-N2-(4-(4-methyl-piperazin-1-yl)phenyl)pyrimidine-2,4-diamine (Ex-16)

This was prepared from Int-16 (0.100 g, 0.35 mmol), 4-(4-methylpiperazin-1-yl)aniline (0.064 g, 0.33 mmol) and 4 M HCl in dioxane (0.08 mL, 0.33 mmol) in 2-methoxyethan-1-ol (2 mL) in the same way as Ex-7 to provide crude material which was purified by $SiO_2$ flash chromatography. The white solid obtained was triturated with DCM/Hex to afford the titled compound as a solid (0.042 g, 30%). HPLC 97% ($t_R$=13.0 min, 40% $CH_3OH$ in 0.1% TFA water, 20 min); HPLC-MS (ESI+) m/z 437 (M+H); LC-MS (ESI+) m/z 437 (M+H)$^+$; HRMS (ESI+) m/z calculated for $C_{24}H_{29}ClN_6$ (M+H)$^+$ 437.2215, found 437.2209.

Example 17

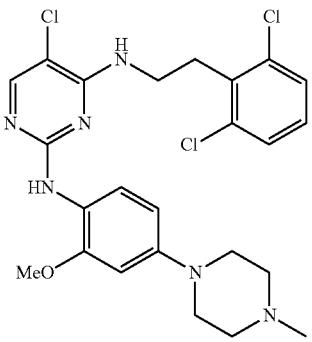 [SMILES: COc1cc(N2CCN(C)CC2)ccc1Nc1ncc(Cl)c(NCCc2c(Cl)cccc2Cl)n1]

5-Chloro-$N^4$-(2,6-dichlorophenethyl)-$N^2$-[2-methoxy-4-(4-methylpiperazin-1-yl)phenyl]pyrimidine-2,4-diamine (Ex-17)

To Int-17 (50 mg, 0.148 mmol) and 2-methoxy-4-(4-methylpiperazin-1-yl) aniline (33 mg, 0.148 mmol) in MeOH (1 mL), 2 drops of 4 M HCl (aq.) was added. The solution was irradiated under microwave conditions for 30 minutes at 160° C. The solution was transferred to a separatory funnel with EtOAc (40 mL), and washed with saturated $NaHCO_3$ (10 mL). The aqueous layer was re-extracted with EtOAc (2×20 mL). The organic layers were combined, dried ($Na_2SO_4$), filtered, and concentrated under reduced pressure. The resulting crude mixture was purified by flash chromatography ($SiO_2$) eluting with DCM in MeOH (0% to 10%) to provide the title compound as a thin film (27 mg, 35%). HPLC: 94% [$t_R$=5.9 min, 45% MeOH, 55% water (with 0.1% TFA), 20 min]. $^1$H NMR (400 MHz, DMSO-$d_6$): δ 7.87 (d, J=8.8 Hz, 1H), 7.85 (s, 1H), 7.40 (d, J=8.1 Hz, 2H), 7.31 (t, J=6.8 Hz, 1H), 7.29 (s, 1H, disappeared on $D_2O$ shake), 7.23 (t, J=8.1 Hz, 1H), 6.60 (d, J=2.5 Hz, 1H), 6.43 (dd, J=8.8, 2.5 Hz, 1H), 3.82 (s, 3H), 3.59 (q, J=6.8 Hz, 2H), 3.18 (d, J=6.8 Hz, 3H from methanol), 3.10-3.04 (m, 4H), 2.46-2.41 (m, 4H), 2.20 (s, 3H). HPLC-MS (ESI+): m/z 523.2 [25%, ($M^{35}Cl^{35}Cl^{37}Cl$+H)$^+$], 521.2 [25%, ($M^{35}Cl^{35}Cl^{35}Cl$+H)$^+$], 262.2 [100%, ($M^{35}Cl^{35}Cl^{37}Cl$+2H)$^{2+}$], 261.2 [95%, ($M^{35}Cl^{35}Cl^{35}Cl$+2H)$^{2+}$]. LC-MS (ESI+): 521.2 [100%, ($M^{35}Cl^{35}Cl^{35}Cl$+H)$^+$]. HRMS (ESI+): m/z calcd for $C_{24}H_{27}Cl_3N_6O$ (M+H)$^+$ 521.1385, found 521.1390.

Example 18

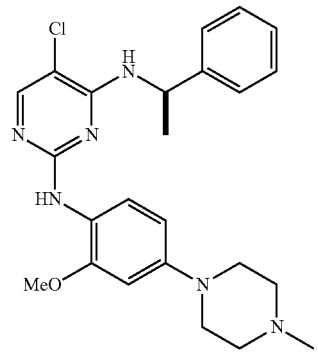

(R)5-Chloro-$N^4$-(1-phenylethyl)-$N^2$-[2-methoxy-4-(4-methylpiperazin-1-yl)phenyl]pyrimidine-2,4-diamine (Ex-18)

This was prepared from JM1-080 (50 mg, 0.186 mmol) and 2-methoxy-4-(4-methylpiperazin-1-yl) aniline (41 mg, 0.186 mmol) in the same way as Ex-17 to provide the title compound as a thin film (27 mg, 35%). HPLC: 93% [$t_R$=7.0 min, 35% MeOH, 65% water (with 0.1% TFA), 20 min]. $^1$H NMR (400 MHz, DMSO-$d_6$): δ 7.84 (s, 1H), 7.58 (d, J=8.8 Hz, 1H), 7.41 (s, 1H, disappeared on $D_2O$ shake), 7.38-7.23 (m, 5H; 1H disappeared on $D_2O$ shake), 7.17 (t, J=7.2 Hz, 1H), 6.57 (d, J=2.5 Hz, 1H), 6.42 (dd, J=8.8, 2.5 Hz, 1H), 5.20 (pentet, J=7.4 Hz, 1H), 3.75 (s, 3H), 3.12-3.05 (m, 4H), 2.47-2.41 (m, 4H), 2.21 (s, 3H), 1.48 (d, J=7.1 Hz, 3H). HPLC-MS (ESI+): m/z 453.3 [30%, ($M^{35}Cl$+H)$^+$], 227.9 [35%, ($M^{37}Cl$+2H)$^{2+}$], 227.2 [100%, ($M^{35}Cl$+2H)$^{2+}$]. LC-MS (ESI+): 453.2 [100%, ($M^{35}Cl$+H)$^+$]. HRMS (ESI+): m/z calcd for $C_{24}H_{29}ClN_6O$ (M+H)$^+$ 453.2164, found 453.2157.

Example 19

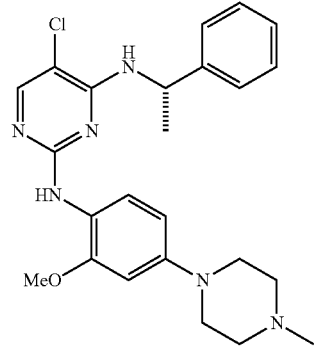 [SMILES: COc1cc(N2CCN(C)CC2)ccc1Nc1ncc(Cl)c(N[C@@H](C)c2ccccc2)n1]

(S)5-Chloro-$N^4$-(1-phenylethyl)-$N^2$-[2-methoxy-4-(4-methylpiperazin-1-yl)phenyl]pyrimidine-2,4-diamine (Ex-19)

This was prepared from Int-19 (50 mg, 0.186 mmol) and 2-methoxy-4-(4-methylpiperazin-1-yl) aniline (41 mg, 0.186 mmol) in the same way as Ex-17 to provide the title compound as a thin film (28 mg, 35%). HPLC: 98% [$t_R$=8.9 min, 35% MeOH, 65% water (with 0.1% TFA), 20 min]. $^1$H NMR (400 MHz, DMSO-$d_6$): δ 7.84 (s, 1H), 7.58 (d, J=8.8 Hz, 1H), 7.42 (s, 1H 1H disappeared on $D_2O$ shake), 7.38-7.23 (m, 5H; 1H disappeared on $D_2O$ shake), 7.17 (t, J=7.2 Hz, 1H), 6.57 (d, J=2.4 Hz, 1H), 6.42 (dd, J=8.8, 2.4 Hz, 1H), 5.21 (pentet, J=7.4 Hz, 1H), 3.75 (s, 3H), 3.12-3.05 (m, 4H), 2.47-2.41 (m, 4H), 2.21 (s, 3H), 1.48 (d, J=7.1 Hz, 3H). HPLC-MS (ESI+): m/z 453.2 [30%, $(M^{35}Cl+H)^+$], 228.0 [35%, $(M^{37}Cl+2H)^{2+}$], 227.2 [100%, $(M^{35}Cl+2H)^{2+}$]. LC-MS (ESI+): 453.2 [100%, $(M^{35}Cl+H)^+$]. HRMS (ESI+): m/z calcd for $C_{24}H_{29}ClN_6O$ $(M+H)^+$ 453.2164, found 453.2162.

Example 20

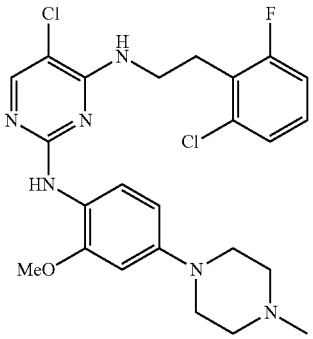 [SMILES: COc1cc(N2CCN(C)CC2)ccc1Nc1ncc(Cl)c(NCCc2c(F)cccc2Cl)n1]

5-Chloro-$N^4$-(2-chloro-6-fluorophenethyl)-$N^2$-[2-methoxy-4-(4-methylpiperazin-1-yl)phenyl]pyrimidine-2,4-diamine (Ex-20)

To a solution of Int-12 (100 mg, 0.312 mmol) and 2-methoxy-4-(4-methylpiperazin-1-yl)aniline (75 mg, 0.343 mmol) in 2-methoxyethanol (2 mL) was added 4 M HCl in dioxane (0.086 mL, 0.343 mmol). The solution was stirred and heated at 110° C. for 14 h. Then, additional 2-methoxy-4-(4-methylpiperazin-1-yl)aniline (18 mg, 0.081 mmol) and 1 drop of 4 M HCl (aq) were added and the mixture was further irradiated under microwave conditions for 15 minutes at 160° C. The solution was concentrated under reduced pressure and partitioned between saturated $NaHCO_3$ and DCM (20 mL each). The aqueous layer was re-extracted with DCM (20 mL). The organic layers were combined, dried ($Na_2SO_4$), filtered, and concentrated under reduced pressure. The resulting crude mixture was purified by flash chromatography ($SiO_2$) eluting with DCM in MeOH (0% to 10%) to provide the title compound as a brown foam (75 mg, 48%). HPLC: 98% [$t_R$=8.7 min, 45% MeOH, 55% water (with 0.1% TFA), 20 min. $^1$H NMR (400 MHz, DMSO-$d_6$): δ 7.87 (d, J=8.8 Hz, 1H), 7.84 (s, 1H), 7.33-7.22 (m, 4H; 1H disappeared on $D_2O$ shake), 7.19-7.11 (m, 1H), 6.60 (d, J=2.5 Hz, 1H), 6.42 (dd, J=8.8, 2.5 Hz, 1H), 3.81 (s, 3H), 3.58 (q, J=6.6 Hz, 2H), 3.10-3.05 (m, 4H), 3.03 (t, J=6.6 Hz, 2H), 2.46-2.42 (m, 4H), 2.21 (s, 3H). HPLC-MS (ESI+): m/z 507.2 [45%, $(M^{35}Cl^{37}Cl+H)^+$], 505.2 [50%, $(M^{35}Cl^{35}Cl+H)^+$], 254.2 [60%, $(M^{35}Cl^{37}Cl+2H)^{2+}$], 253.2 [100%, $(M^{35}Cl^{35}Cl+2H)^{2+}$]. LC-MS (ESI+): 505.2 [100%, $(M^{35}Cl^{35}Cl+H)$]. HRMS (ESI+): m/z calcd for $C_{24}H_{27}Cl_2FN_6OS$ $(M+H)^+$ 505.1680, found 505.1683.

Example 21

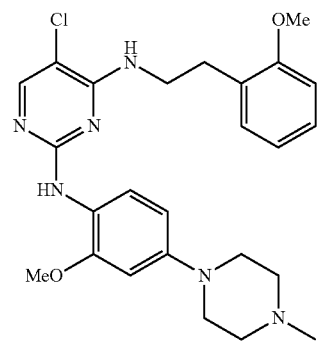 [SMILES: COc1ccccc1CCNc1nc(Nc2ccc(N3CCN(C)CC3)cc2OC)ncc1Cl]

5-Chloro-$N^2$-[2-methoxy-4-(4-methylpiperazin-1-yl)phenyl]-$N^4$-(2-methoxyphenethyl)pyrimidine-2,4-diamine (Ex-21)

To a solution of Int-14 (100 mg, 0.335 mmol) and 2-methoxy-4-(4-methylpiperazin-1-yl)aniline (82 mg, 0.369 mmol) in 2-methoxyethanol (2 mL) was added 4 M HCl in dioxane (0.086 mL, 0.343 mmol). The solution was stirred and heated at 110° C. for 14 h. Then, additional 2-methoxy-4-(4-methylpiperazin-1-yl)aniline (40 mg, 0.180 mmol) and 1 drop of 4 M HCl (aq) were added and the mixture was further irradiated under microwave conditions for 15 minutes at 160° C. Work up in the same way as Ex-20 provided the title compound as a light brown foam (97 mg, 60%). HPLC: 99% [$t_R$=8.7 min, 45% MeOH, 55% water (with 0.1% TFA), 20 min. $^1$H NMR (400 MHz, DMSO-$d_6$): δ 7.83 (d, J=8.8 Hz, 1H), 7.82 (s, 1H), 7.42 (s, 1H, disappeared on $D_2O$ shake), 7.18 (ddd, J=8.2, 7.4, 1.7 Hz, 1H), 7.14 (t, J=6.3 Hz, 1H, reduced by 50% on $D_2O$ shake), 7.07 (dd, J=7.4, 1.7 Hz, 1H), 6.94 (dd, J=8.2, 0.9 Hz, 1H), 6.85 (td, J=7.4, 0.9 Hz, 1H), 6.60 (d, J=2.5 Hz, 1H), 6.34 (dd, J=8.8, 2.5 Hz, 1H), 3.79 (s, 3H), 3.76 (s, 3H), 3.50 (q, J=6.3 Hz, 2H), 3.10-3.03 (m, 4H), 2.82 (t, J=6.3 Hz, 2H), 2.47-2.41 (m, 4H), 2.21 (s, 3H). HPLC-MS (ESI+): m/z 483.3 [50%, $(M^{35}Cl+H)^+$], 242.2 [100%, $(M^{35}Cl+2H)^{2+}$]. LC-MS (ESI+): 483.2 [100%, $(M^{35}Cl+H)^+$]. HRMS (ESI+): m/z calcd for $C_{25}H_{31}Cl_2N_6O_2$ $(M+H)^+$ 483.2270, found 483.2272.

Example 22

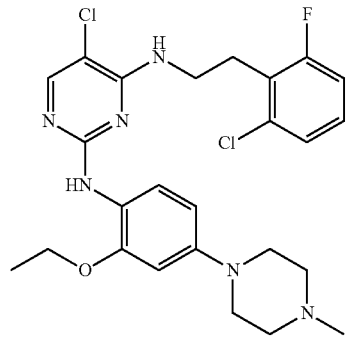 [SMILES: CCOc1cc(N2CCN(C)CC2)ccc1Nc1ncc(Cl)c(NCCc2c(F)cccc2Cl)n1]

5-Chloro-$N^4$-(2-chloro-6-fluorophenethyl)-$N^2$-[2-ethoxy-4-(4-methylpiperazin-1-yl)phenyl]pyrimidine-2,4-diamine (Ex-22)

To a solution of 2,5-dichloro-N-(2-chloro-6-fluorophenethyl)pyrimidin-4-amine (Int-12) (100 mg, 0.312 mmol) and 2-ethoxy-4-(4-methylpiperazin-1-yl)aniline (81 mg, 0.343 mmol) in 2-methoxyethanol (2 mL), 86 µL of 4 M HCl in dioxane was added. The solution was stirred and heated to 110° C. for 14 h, then irradiated under microwave conditions for 15 minutes at 160° C. The mixture was concentrated in vacuo. Then saturated $NaHCO_3$ (20 mL) and dichloromethane (20 mL) were added and transferred to a separatory funnel. The aqueous layer was re-extracted with dichloromethane (2×20 mL). The organic layers were combined, dried ($Na_2SO_4$), filtered, and concentrated under reduced pressure. The resulting residue was purified by preparative TLC eluting with dichloromethane and acetone (2:1, v/v) to provide the title compound as brown foam (50 mg, 31%). HPLC: 97% [$t_R$=9.03 min, 45% MeOH, 55% water (with 0.1% TFA), 20 min]. $^1$H NMR (400 MHz, DMSO-$d_6$): δ 8.02 (d, J=8.8, 1H), 7.88 (s, 1H), 7.37 (t, J=5.9 Hz, 1H), 7.32-7.23 (m, 3H), 7.20-7.12 (m, 1H), 6.63 (d, J=2.5 Hz, 1H), 6.46 (dd, J=8.9, 2.5 Hz, 1H), 4.10 (q, J=7.0 Hz, 2H), 3.60 (q, J=6.5 Hz, 2H), 3.15 (brs, 4H), 3.05 (t, J=6.4 Hz, 2H), 2.70 (brs, 4H), 2.40 (s, 3H), 1.38 (t, J=7.0 Hz, 3H). HPLC-MS (ESI+): m/z 521.3 [20%, $(M^{35}Cl^{37}Cl+H)^+$], 519.2 [35%, $(M^{35}Cl^{35}Cl+H)^+$], 261.1 [66%, $(M^{35}Cl^{37}Cl+2H)^{2+}$], 260.3 [100%, $(M^{35}Cl^{35}Cl+2H)^{2+}$].

Example 23

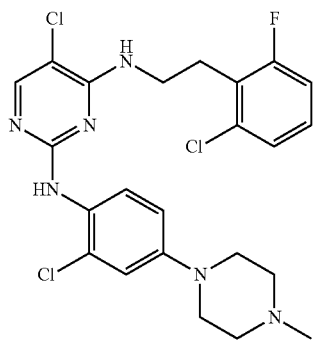 [SMILES: CN1CCN(c2ccc(Nc3ncc(Cl)c(NCCc4c(F)cccc4Cl)n3)c(Cl)c2)CC1]

5-Chloro-$N^2$-[2-chloro-4-(4-methylpiperazin-1-yl)phenyl]-$N^4$-(2-chloro-6-fluorophenethyl)pyrimidine-2,4-diamine (Ex-23)

To a solution of 2,5-dichloro-N-(2-chloro-6-fluorophenethyl)pyrimidin-4-amine (Int-12) (50 mg, 0.156 mmol) and 2-chloro-4-(4-methylpiperazin-1-yl)aniline (42 mg, 0.186 mmol) in 2-methoxyethanol (1 mL), 47 µL of 4 M HCl in dioxane was added. The solution was stirred and heated to 110° C. for 14 h, then irradiated under microwave conditions for 15 minutes at 160° C. The mixture was concentrated in vacuo. Then saturated $NaHCO_3$ (10 mL) and dichloromethane (10 mL) were added and transferred to a separatory funnel. The aqueous layer was re-extracted with dichloromethane (2×10 mL). The organic layers were combined, dried ($Na_2SO_4$), filtered, and concentrated under reduced pressure. The resulting residue was purified by preparative TLC eluting with dichloromethane and acetone (2:1, v/v) to provide the title compound as a yellow thin film (13 mg, 17%). HPLC: 98% [$t_R$=6.88 min, 45% MeOH, 55% water (with 0.1% TFA), 20 min]. $^1$H NMR (400 MHz, DMSO-$d_6$): δ 7.92 (s, 1H), 7.82 (s, 1H), 7.56 (d, J=8.9 Hz, 1H), 7.31-7.21 (m, 3H), 7.19-7.09 (m, 1H), 6.97 (d, J=2.8 Hz, 1H), 6.88 (dd, J=9.0, 2.8 Hz, 1H), 3.59-3.46 (q, J=6.4 Hz, 2H), 3.16-3.07 (m, 4H), 2.99 (t, J=6.4 Hz, 2H), 2.47-2.39 (m, 4H), 2.21 (s, 3H). HPLC-MS (ESI+): m/z 511.2 [35%, $(M^{35}Cl^{35}Cl^{37}Cl+H)^+$], 509.1 [35%, $(M^{35}Cl^{35}Cl^{35}Cl+H)^+$], 256.1 [100%, $(M^{35}Cl^{35}Cl^{37}Cl+2H)^{2+}$], 255.2 [98%, $(M^{35}Cl^{35}Cl^{35}Cl+2H)^{2+}$].

Example 24

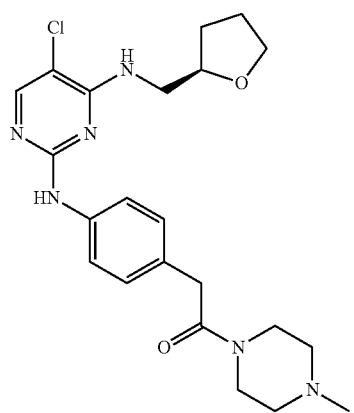 [SMILES: CN1CCN(C(=O)Cc2ccc(Nc3ncc(Cl)c(NC[C@H]4CCCO4)n3)cc2)CC1]

(R)-2-(4-((5-chloro-4-(((tetrahydrofuran-2-yl)methyl)amino)pyrimidin-2-yl)amino)phenyl)-1-(4-methylpiperazin-1-yl)ethan-1-one (Ex-24)

This compound was synthesized using the procedure described for Ex-1 except using (R)-2,5-dichloro-N-((tetrahydrofuran-2-yl)methyl)pyrimidin-4-amine (Lawrence, H. R.; et al. (2015) Development of Novel ACK1/TNK2 Inhibitors Using a Fragment Based Approach. J. Med. Chem. 58 (6), 2746-2763) (0.100 g, 0.403 mmol), 2-(4-aminophenyl)-1-(4-methylpiperazin-1-yl)ethan-1-one (0.089 g, 0.383 mmol) and 4 M HCl in dioxane (0.1 mL, 0.403 mmol) in 2-methoxyethan-1-ol (2 mL) to afford the title compound as a beige color solid (0.109 g, 64%). HPLC 97.6% ($t_R$=6.88 min, 30% $CH_3OH$ in 0.1% TFA water, 20 min); $^1$H NMR (400 MHz, $CDOD_3$): δ 7.01 (s, 1H), 6.78 (appd, J=8.8 Hz, 2H), 6.34 (d, J=8.8 Hz, 2H), 3.39-3.33 (m, 1H), 3.10-3.05 (m, 1H), 2.95 (aapt, 1H), 2.92 (s, 2H), 2.83-2.69 (m, 6H), 1.58 (t, J=5.2 Hz, 2H), 1.46 (t, J=4.8 Hz, 2H), 1.44 (s, 3H), 1.24-1.03 (m, 3H), 0.91-0.82 (m, 1H); LC-MS (ESI+) m/z 223.2 $(M+2H)^{2+}$, 445.2 $(M+H)^+$; HRMS (ESI+) m/z calculated for $C_{22}H_{30}ClN_6O_2(M+H)^+$ 445.2113, found 445.2109.

Example 25

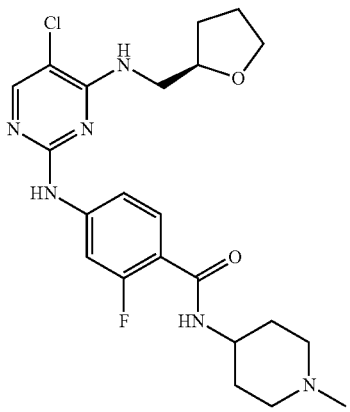 [SMILES: CN1CCC(NC(=O)c2ccc(Nc3ncc(Cl)c(NC[C@H]4CCCO4)n3)cc2F)CC1]

(R)-4-((5-chloro-4-(((tetrahydrofuran-2-yl)methyl)amino)pyrimidin-2-yl)amino)-2-fluoro-N-(1-methyl-piperidin-4-yl)benzamide (Ex-25)

This compound was synthesized using the procedure described for Ex-1 from (R)-2,5-dichloro-N-((tetrahydrofuran-2-yl)methyl)pyrimidin-4-amine (Lawrence, H. R.; et al. (2015) Development of Novel ACK1/TNK2 Inhibitors Using a Fragment Based Approach. J. Med. Chem. 58 (6), 2746-2763) (0.100 g, 0.403 mmol), 4-amino-2-fluoro-N-(1-methylpiperidin-4-yl)benzamide (0.096 g, 0.383) and 4 M HCl in dioxane (0.1 mL, 0.403 mmol) in 2-methoxyethan-1-ol (2 mL) to afford the title compound as a white solid (0.097 g, 55%). HPLC 99.6% ($t_R$=12.21 min, 30% $CH_3OH$ in 0.1% TFA water, 20 min); $^1H$ NMR (400 MHz, $CDOD_3$): δ 9.69 (s, 1H), 8.00 (s, 1H), 7.85-7.81 (m, 2H), 7.49-7.40 (m, 2H), 7.31 (t, J=6.0 Hz, 1H), 4.13-4.07 (m, 1H), 3.79-3.74 (m, 1H), 3.67-3.59 (m, 2H), 3.48-3.44 (m, 2H), 2.69 (brd, J=11.2 Hz, 2H), 2.13 (s, 3H), 1.94-1.72 (m, 7H), 1.63-1.49 (m, 3H); $^{19}F$ NMR (376 MHz, DMSO-$d_6$): δ −112.25-−112.30 (m); LC-MS (ESI+) m/z 232.2 $(M+2H)^{2+}$, 463.2 $(M+H)^+$; HRMS (ESI+) m/z calculated for $C_{22}H_{29}ClFN_6O_2$ $(M+H)^+$ 463.2019, found 463.2012.

Example 26

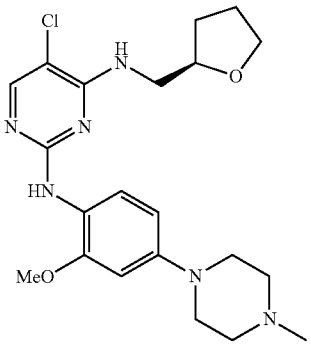 [SMILES: COc1cc(N2CCN(C)CC2)ccc1Nc1ncc(Cl)c(NC[C@H]2CCCO2)n1]

(R)-5-Chloro-$N^2$-[2-methoxy-4-(4-methylpiperazin-1-yl)phenyl]-$N^4$-[(tetrahydrofuran-2-yl)methyl]pyrimidine-2,4-diamine (Ex-26)

To a solution of (R)-2,5-dichloro-N-((tetrahydrofuran-2-yl)methyl)pyrimidin-4-amine (Lawrence, H. R.; et al. (2015) Development of Novel ACK1/TNK2 Inhibitors Using a Fragment Based Approach. J. Med. Chem. 58 (6), 2746-2763) (0.100 g, 0.403 mmol) and 2-methoxy-4-(4-methylpiperazin-1-yl)aniline (98 mg, 0.443 mmol) in 2-methoxyethanol (2 mL) was added 4 M HCl in dioxane (0.110 mL, 0.443 mmol). The solution was stirred and heated at 110° C. for 18 h. Then, the mixture was concentrated under reduced pressure and partitioned between saturated $NaHCO_3$ and $CHCl_3$ (20 mL each). The aqueous layer was re-extracted with $CHCl_3$ (20 mL). The organic layers were combined, dried ($Na_2SO_4$), filtered, and concentrated under reduced pressure. The resulting crude mixture was purified by flash chromatography ($SiO_2$) eluting with DCM in MeOH (0% to 10%) to provide the title compound as a brown oil (79 mg, 54%). HPLC: 95% [$t_R$=6.8 min, 30% MeOH, 70% water (with 0.1% TFA), 20 min. $^1H$ NMR (400 MHz, DMSO-$d_6$): δ 7.84 (s, 1H), 7.78 (d, J=8.8 Hz, 1H), 7.45 (s, 1H, disappeared on $D_2O$ shake), 7.00 (t, J=6.0 Hz, 1H, disappeared on $D_2O$ shake), 6.59 (d, J=2.6 Hz, 1H), 6.42 (dd, J=8.8, 2.6 Hz, 1H), 4.03 (pentet, J=6.0 Hz, 1H), 3.79 (s, 3H), 3.76-3.69 (m, 1H), 3.62-3.56 (m, 1H), 3.36 (t, J=6.0 Hz, 2H), 3.10-3.04 (m, 4H), 2.46-2.40 (m, 4H), 2.20 (s, 3H), 1.90-1.71 (m, 3H), 1.60-1.50 (m, 1H). HPLC-MS (ESI+): m/z 433.2 [30%, $(M^{35}Cl+H)^+$], 218.2 [40%, $(M^{37}Cl+2H)^{2+}$], 217.2 [100%, $(M^{35}Cl+2H)^{2+}$]. LC-MS (ESI+): 433.2 [100%, $(M^{35}Cl+H)$]. HRMS (ESI+): m/z calcd for $C_{21}H_{29}ClN_6O_2(M+H)^+$ 433.2113, found 433.2106.

Biological Activity

Androgen receptor (AR) plays a paramount role in the onset and progression of prostate cancer (PC) (Burnstein, K. L. (2005). Regulation of androgen receptor levels: implications for prostate cancer progression and therapy. J. Cell. Biochem. 95, 657-669; Grossmann, M. E., et al. (2001). Androgen receptor signaling in androgen-refractory prostate cancer. J. Nat. Cancer Inst. 93, 1687-1697; Lonergan, P. E., and Tindall, D. J. (2011). Androgen receptor signaling in prostate cancer development and progression. J. Carcinogenesis 10, 20; Watson, P. A., et al. (2015). Emerging mechanisms of resistance to androgen receptor inhibitors in prostate cancer. Nature Rev. 15, 701-711). Emerging mechanisms of resistance to androgen receptor inhibitors in prostate cancer. Nature Rev. 15, 701-711). Despite initial response, AR antagonists are ineffective long term in stifling AR activity due to their inability to repress expression of AR or its splice variant, AR-V7. PC cells reinvigorate AR gene transcription as a swift response to antiandrogens and progress to a lethal stage, Castration Resistant Prostate Cancer (CRPC) (Grasso, C. S., et al. (2012). The mutational landscape of lethal castration-resistant prostate cancer. Nature 487, 239-243; Robinson, D., et al. (2015). Integrative clinical genomics of advanced prostate cancer. Cell 161, 1215-1228). The intrinsic ability of CRPCs to increase AR and AR-V7 levels reiterates that inhibition of AR protein activity is not enough; to achieve effective remission, ablation of AR transcription is critical. However, targeted inhibition of AR and its splice variant, AR-V7 transcription with small molecule inhibitors has not yet been accomplished. We uncovered that the AR-interacting non-receptor tyrosine kinase (NRTK), ACK1 (also known as TNK2), frequently deregulated in CRPCs (Mahajan, K., and Mahajan, N. P. (2015). ACK1/TNK2 tyrosine kinase: molecular signaling and evolving role in cancers. Oncogene 34, 4162-4167; Mahajan, N. P., et al. (2007). Activated Cdc42-associated kinase ACK1 promotes prostate cancer progression via androgen receptor tyrosine phosphorylation. Proc. Nat. Acad. Sci. U.S.A. 104, 8438-8443), phosphorylates histone H4 at tyrosine88. ACK1 is directly recruited to AR locus and deposits pY88-H4 marks, which are 'read' by WDR5 and MLL2 histone-Lysine N-methyltransferase complex, facilitating deposition of the H3K4 trimethyl activating marks. This autonomous epigenetic circuitry driving AR and AR-V7 expression is not only androgen-independent, but also insensitive to the second generation anti-androgen, enzalutamide (Tran et al., 2009). Consistently, reversal of the pY88-H4 epigenetic marks by ACK1 inhibitor, (R)-9bMS (DZ1-067 mesylate salt), not only repressed AR and its variant levels and sensitized enzalutamide-resistant cancer cells, but also mitigated in vivo CRPC tumor growth. Combined together, these reveal a positive feedback circuitry driven by a histone tyrosine kinase that reinforces AR and its variant transcription, fostering CRPC growth. Further, these data signal the emergence of a new class of epigenetic inhibitor, (R)-9bMS as a viable treatment option for CRPCs. Moreover, we observed that ACK1 inhibitor (R)-9bMS acts as an immunomodulatory inhibitor. Suppression of ACk1 causes significant increase in CD4 helper, CD8 cytotoxic and natural killer (NK) cells. Further, a significant increase in MDSC (myloid-derived suppressor cells) was also observed. Interestingly, the tumors developed in mice lacking ACK1 activity were significantly smaller than in mice with ACK1. Taken together, these data demonstrate that ACK1 kinase activity is critical for cancer cells to keep immune cells 'quiescent'. Thus treatment with ACK1 inhibitor causes tumor suppression by activating immune cells anti-tumor response.

CRPCs invariably overcome enzalutamide blockade (Arora, V. K., et al. (2013). Glucocorticoid receptor confers resistance to antiandrogens by bypassing androgen receptor blockade. Cell 155, 1309-1322; Balbas, M. D., et al. (2013). Overcoming mutation-based resistance to antiandrogens with rational drug design. eLife 2, e00499) and the AR-V7 splice variant (Dehm, S. M., et al. (2008). Splicing of a novel androgen receptor exon generates a constitutively active androgen receptor that mediates prostate cancer therapy resistance. Cancer Res. 68, 5469-5477) may be one of the mechanism for resistance to enzalutamide and androgen-synthesis inhibitor, abiraterone (Antonarakis, E. S., et al. (2014). AR-V7 and resistance to enzalutamide and abiraterone in prostate cancer. New England J. Med. 371, 1028-1038). Thus, it reveals two major caveats for tackling this complex disease; first, not all CRPCs are the same and second, other signaling events e.g. activation of tyrosine kinases may be driving the disease (Drake, J. M., et al. (2012). Oncogene-specific activation of tyrosine kinase networks during prostate cancer progression. Proc. Nat. Acad. Sci. U.S.A. 109, 1643-1648). NRTK such as ACK1 interacts with AR in androgen-independent manner (Mahajan, N. P., et al. (2007). Activated Cdc42-associated kinase ACK1 promotes prostate cancer progression via androgen receptor tyrosine phosphorylation. Proc. Nat. Acad. Sci. U.S.A. 104, 8438-8443) and is frequently upregulated in PCs (Taylor, B. S., et al. (2010). Integrative genomic profiling of human prostate cancer. Cancer Cell 18, 11-22). Importantly, majority of CRPCs exhibit 5- to >100-fold ACK1 overexpression (van der Horst, E. H., et al. (2005). Metastatic properties and genomic amplification of the tyrosine kinase gene ACK1. Proc. Natl. Acad. Sci. U.S.A. 102, 15901-15906) and its expression correlates positively with the progression of disease to CRPC stage (Mahajan, K., et al. (2010). Effect of ACK1 tyrosine kinase inhibitor on ligand-independent androgen receptor activity. The Prostate 70, 1274-1285). However, whether ACK1 modify epigenetic landscape to promote CRPC progression is not known.

The expression of full length AR has been shown to be needed for the genesis of AR-V7 (Watson, P. A., et al. (2010). Constitutively active androgen receptor splice variants expressed in castration-resistant prostate cancer require full-length androgen receptor. Proc. Nat. Acad. Sci. U.S.A. 107, 16759-16765). We assessed AR-V7 mRNA levels upon treatment with (R)-9bMS (DZ1-067 mesylate salt). Both, AR-V7 mRNA and variant protein levels were significantly reduced upon ACK1 inhibition (FIG. 1A-1C). Further, to examine the requirement of ACK1 kinase activity in AR expression, transfection of PC3 cells, which exhibit undetectable levels of AR, was carried out. The constitutively active ACK1, but, not kinase dead ACK1, not only induced significant AR (and PSA) mRNA expression, but also lead to detectable AR protein levels (FIG. 1D-1F).

Figure 2B:
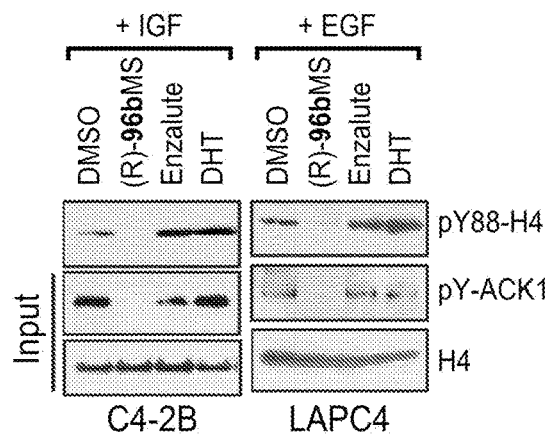
Figure 2C:
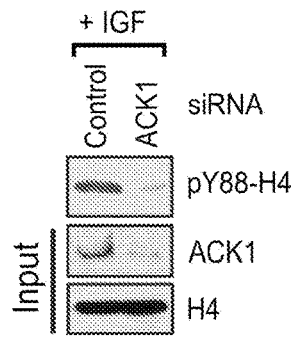

To assess endogenous H4-phosphorylation, serum and androgen starved PC cells were treated with ligands to activate ACK1. It led to robust H4 Y88-phosphorylation, suppressed upon (R)-9bMS treatment (FIG. 2A). Further, H4 Y88-phosphorylation remained unaffected by DHT or enzalutamide treatment (FIG. 2B), however, silencing of ACK1 resulted in a significant loss of H4 Y88-phosphorylation (FIG. 2C). Moreover, H4 Y88-phosphorylation was also detected in human CRPCs using mass spectrometry, which was validated by immunoblotting (FIG. 3A-3C).

Figures 4A, 4B:
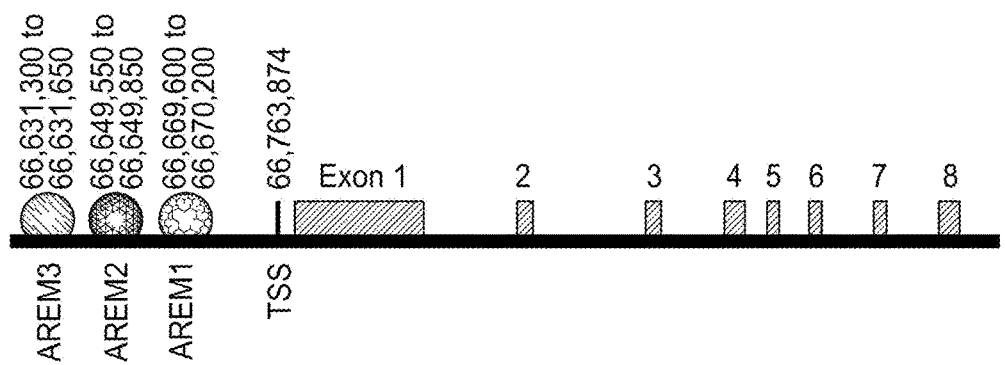
FIGS. 4A and 4B. Deposition of pY88-H4 epigenetic marks upstream of AR gene by ACK1.
Figures 5A, 5B, 5C, 5D:
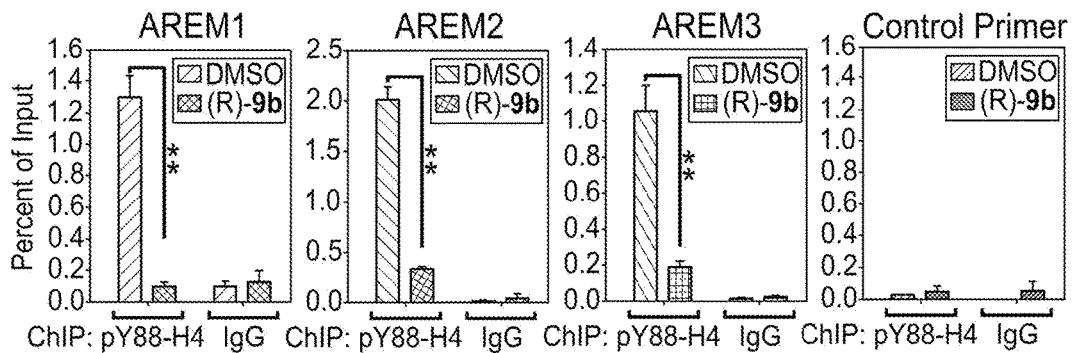
FIG. 5A through 5J. AR transcription is regulated by epigenetic modification of histone H4 at tyrosine 88 is sensitized byc(R)-9bMS.
Figures 5E, 5F, 5G:
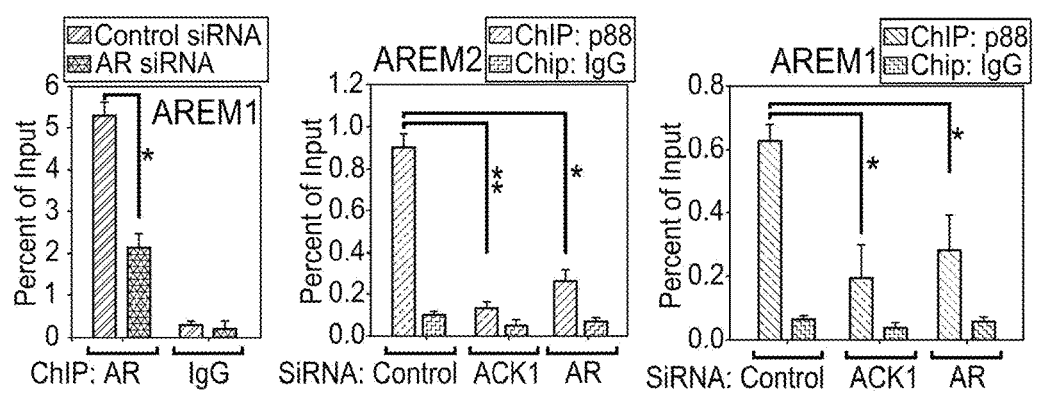

To decipher the pY88-H4 epigenetic landscape in CRPCs, chromatin prepared from vehicle or (R)-9bMS treated C4-2B cells was immunoprecipitated (ChIP) with pY88-H4 antibodies followed by sequencing. A closer examination of X chromosome revealed pY88-H4 deposition at 3 distinct locations upstream of AR transcription start site; AREM1 (nt:66,669,600-66,670,200), AREM2 (nt:66,649,550-66,649,850) and AREM3 (nt:66,631,300-66,631,650) (FIGS. 4A and 4B). ChIP followed by real time PCR revealed that pY88-H4 marks were specifically deposited at these sites and were erased upon (R)-9bMS treatment (FIG. 5A-5D), suggesting that deposition of pY88-H4 epigenetic marks is a reversible event in CRPCs. Further, AR bound upstream of the AR gene (FIG. 5E), and ACK1 or AR knockdown significantly reduced pY88-H4 deposition at AREM1 and 2 site (FIGS. 5F, 5G and 5H), indicating that AR recruits ACK1 upstream of AR gene.

Figures 5H, 5I, 5J:
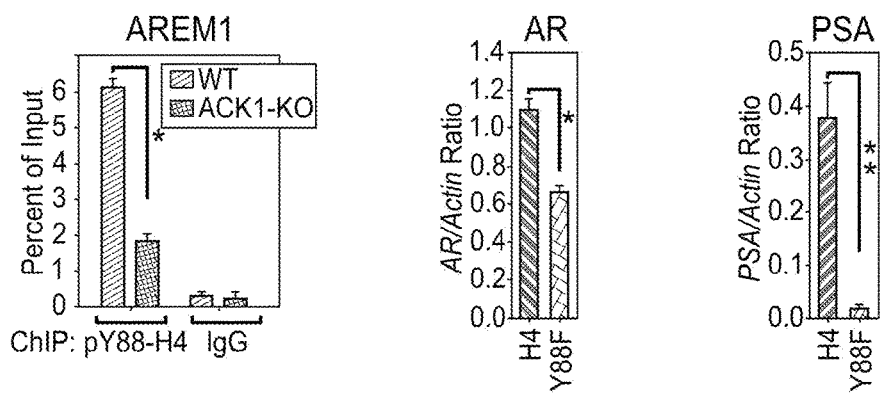

To examine whether the deposition of pY88-H4 marks upstream of AR is necessary for its transcriptional activation, RNA was prepared from cells that were either transfected with the Y88F mutant of H4 or WT-H4. Overexpression of Y88F-H4 mutant resulted in a significant decrease in AR and PSA mRNA levels (FIGS. 5I and 5J).

Figure 6A:
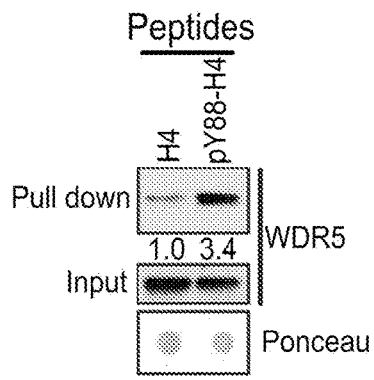
FIG. 6A through 6F. Recruitment of the MLL2/WDR5 complex and deposition of H3K4me3 epigenetic marks upstream of the AR gen can be erased by (R)-9bMS.
Figure 6B:
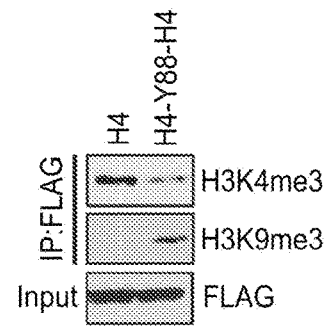
Figure 6C:
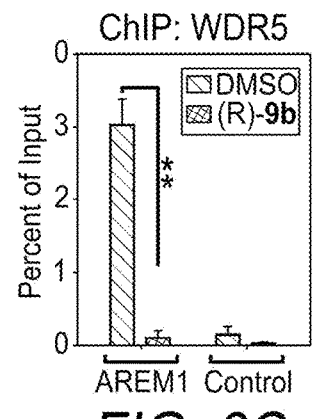
Figure 6D:
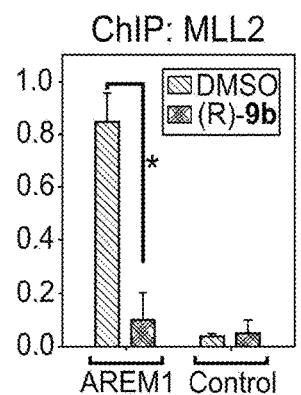
Figure 6E:
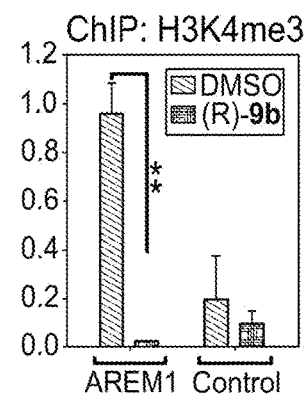
Figure 6F:
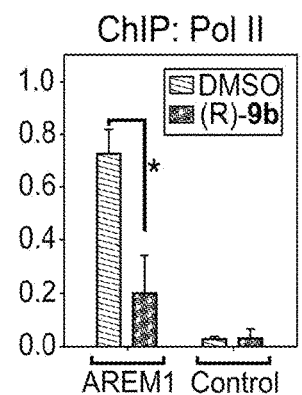

We observed that WDR5 exhibited preferential binding to Y88-phosphorylated-H4, as compared to H4 (FIG. 6A). Further, trimethylation of H3K9, a transcriptionally repressive mark was significantly increased when the deposition of H3K4me3 was compromised, suggesting that the interplay of activating/repressive marks may fine-tune AR mRNA output (FIG. 6B). Moreover, WDR5, MLL2, H3K4me3 methyl marks and RNA Pol II were found to be specifically enriched at the AREM1-3 sites in the absence of androgen and were significantly reduced upon treatment with (R)-9bMS (FIG. 6C-6F). Overall, these data indicate that the H4 Y88-phosphorylation marks may be recognized by the epigenetic reader WDR5 that operate in trans by further recruitment of MLL2, an 'epigenetic scribe', leading to deposition of H3K4me3.

Figure 7A:
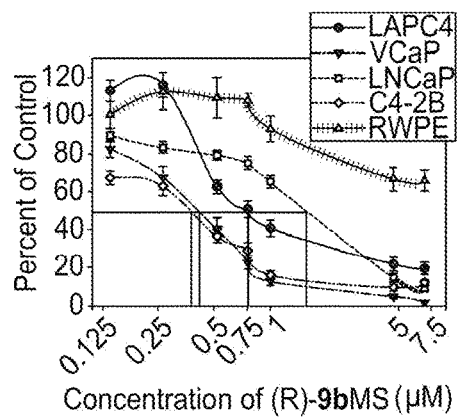
FIG. 7A through 7F. (R)-9bMS overcome enzalutamide-resistance of CRPCs.
Figure 7B:
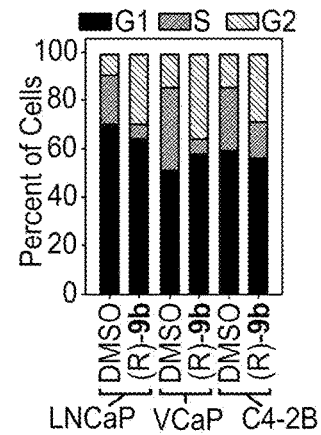
Figure 7C:
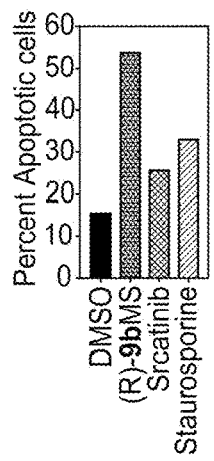

To investigate the anti-tumor activity of ACK1 inhibitor, we first analyzed the ability (R)-9bMS to suppress proliferation of PC cell lines. C4-2B, VCaP, LAPC4 and LNCaP were found to be sensitive to the (R)-9bMS treatment with $IC_{50}$ of 400 nM, 450 nM, 750 nM and 1.8 uM, respectively (FIG. 7A). (R)-9bMS treatment arrest PC cells in G2 phase (FIG. 7B), inducing apoptosis (FIG. 7C).

Figure 7D:
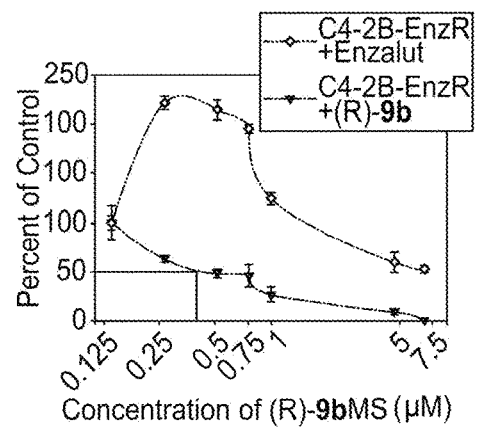
Figure 7E:
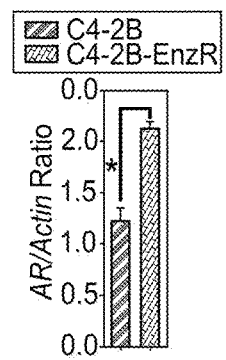
Figure 7F:
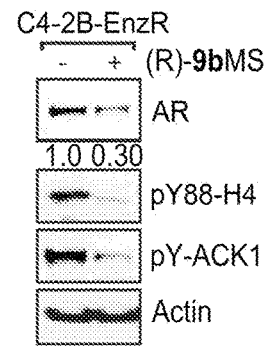

To examine relative sensitivity of CRPCs to enzalutamide and (R)-9bMS, we generated enzalutamide-resistant C4-2B cell line. Although, enzalutamide-resistant cells exhibited considerable resistance to enzalutamide ($IC_{50}$>7.5 uM), cells retained sensitivity for (R)-9bMS treatment (FIG. 7D). Interestingly, these cells exhibited significant increase in AR expression (FIG. 7E), and (R)-9bMS was able to suppress AR expression (FIG. 7F). Taken together, these data suggest that (R)-9bMS can overcome enzalutamide-resistance by downregulating AR transcription, promoting cell cycle arrest and eventual apoptosis.

Figure 8A:
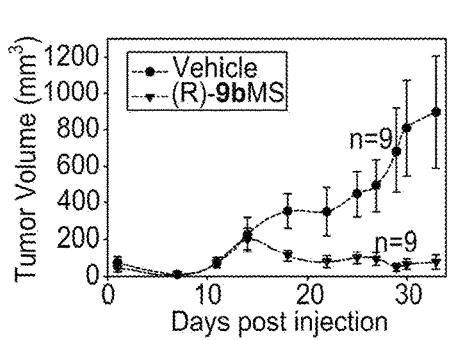
FIG. 8A through 8F. (R)-9bMS mitigates CRPC tumor growth.
Figure 8B:
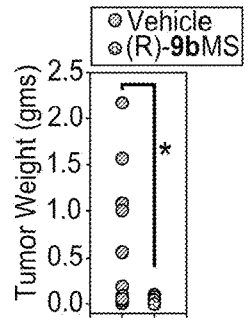
Figure 8C:
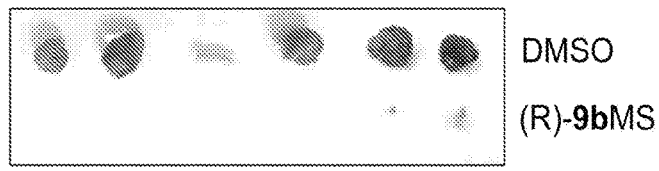
Figure 8D:
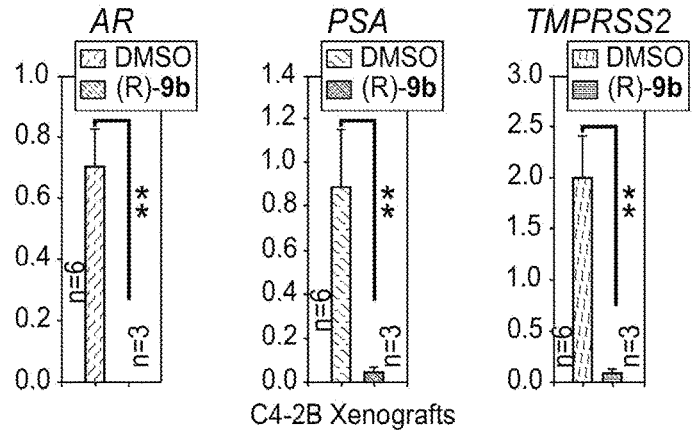
Figure 8E:
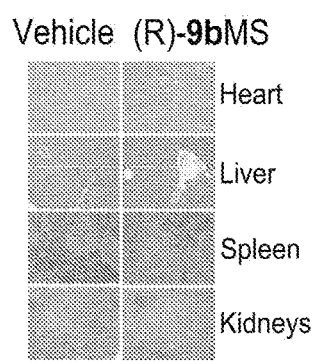
Figure 8F:
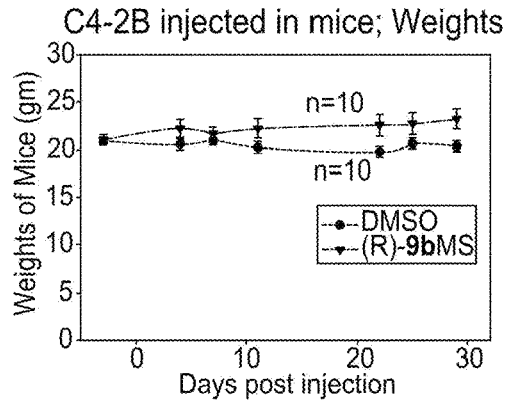

To investigate the effect of (R)-9bMS on CRPC xenograft tumor growth, C4-2B cells were implanted in castrated SCID mice. A significant decrease in CRPC tumor growth and tumor weight was observed in mice injected with (R)-9bMS (FIGS. 8A, 8B and 8C). The (R)-9bMS treated tumors exhibited a significant reduction in AR, PSA & TMPRSS2 mRNAs levels (FIG. 8D). The organs from DMSO or (R)-9bMS treated mice were found to be histologically normal (FIG. 8E) and there was no statistical difference in body weights (FIG. 8F).

Figure 9:
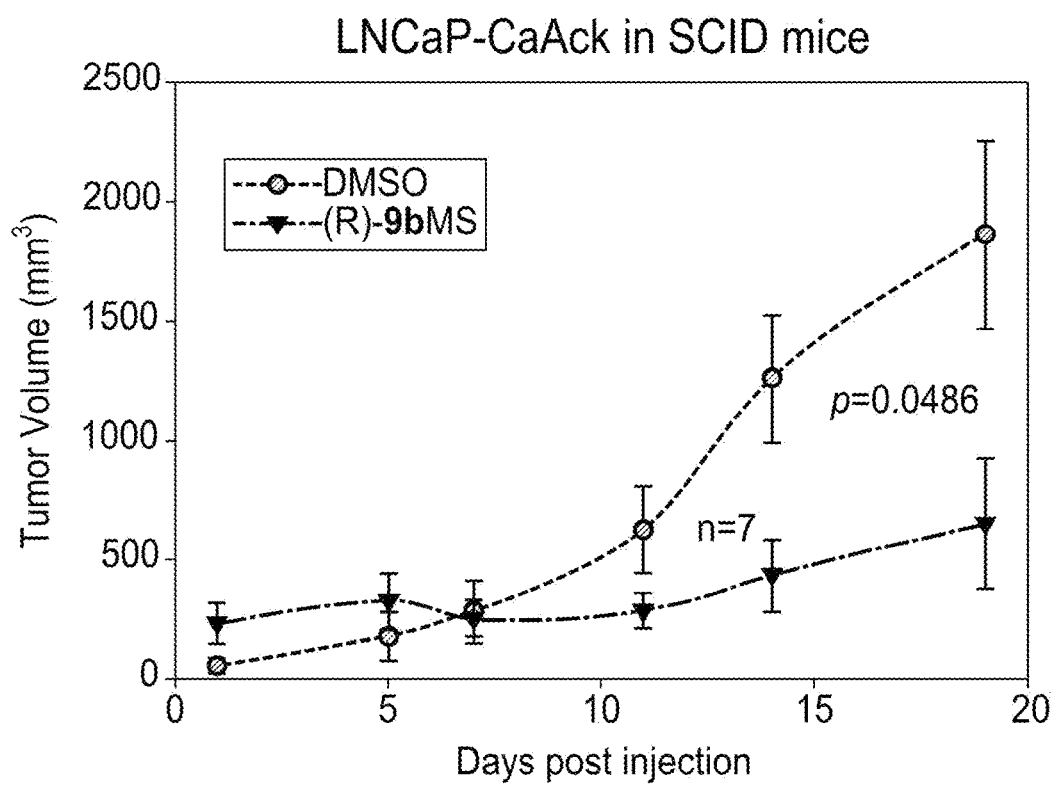
FIG. 9. ACK1 inhibitor (R)-9bMS suppresses xenograft tumor growth in castrated mice. Male SCID mice were castrated and injected with LNCaP-caAck cells. Once mice formed palpable tumors, mice were injected with vehicle (10% DMSO in PBS) or (R)-9bMS (50 mg/kg of body) for 6 days a week for four weeks (n=7 mice for each treatment). Tumor volumes were measured.
Figure 10A:
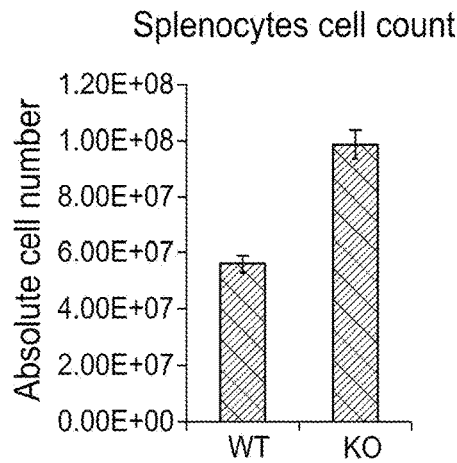
FIG. 10A through 10F. Loss of ACK1 kinase activity significantly increases immune response.
Figure 10B:
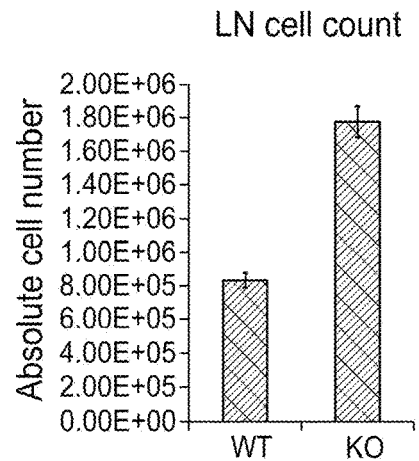
Figure 10C:
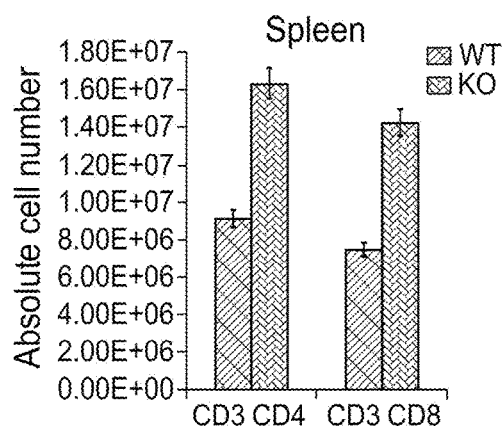
Figure 10D:
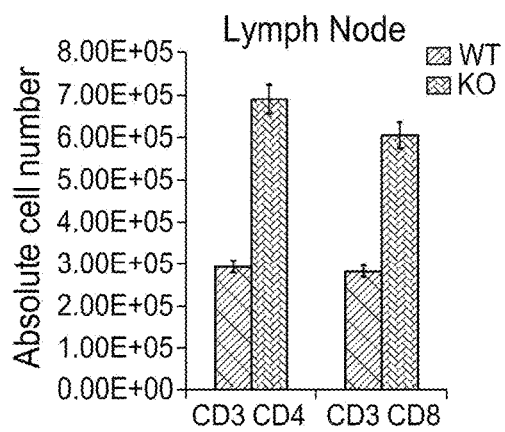
Figure 10E:
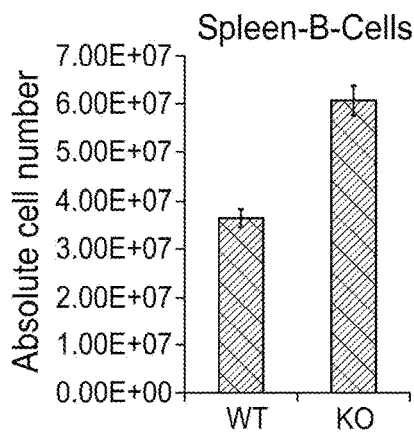
Figure 10F:
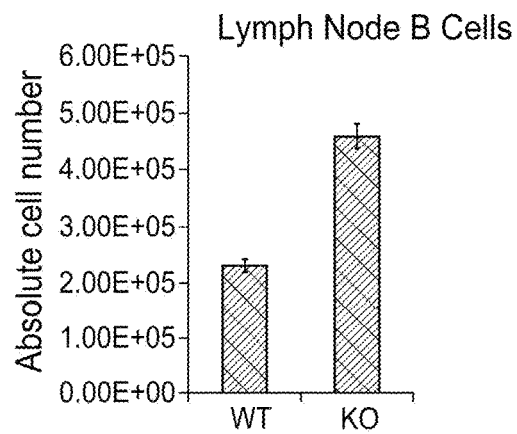
Figure 11A:
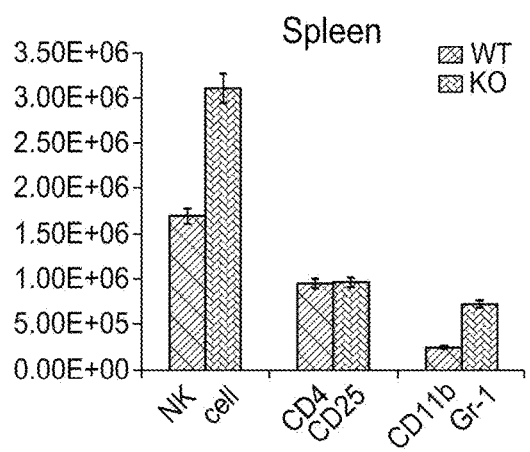
FIG. 11A through 11C. ACK1 kinase activity is critical for cancer cells to keep immune cells 'quiescent'.
Figure 11B:
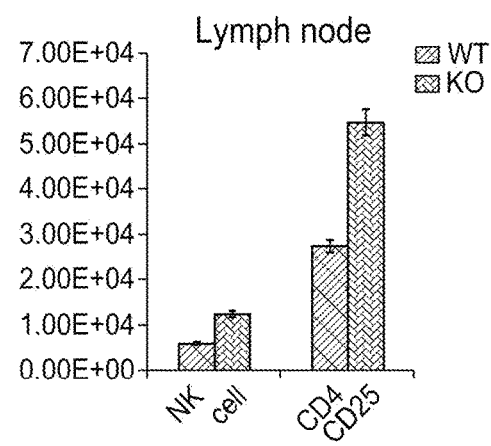
Figure 11C:
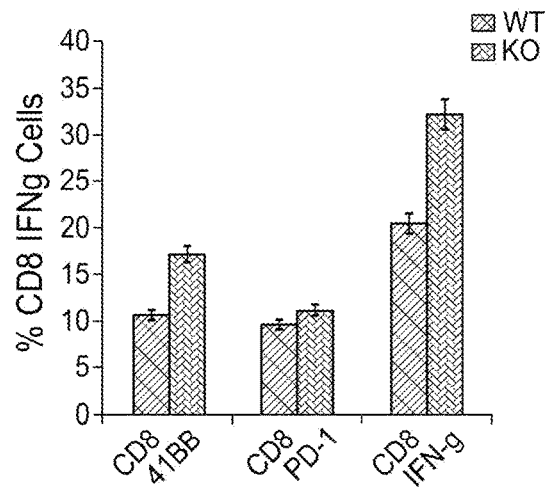

Similarly, LNCaP-caAck, another CRPC model (Mahajan, N. P., et al. (2007). Activated Cdc42-associated kinase ACK1 promotes prostate cancer progression via androgen receptor tyrosine phosphorylation. Proc. Nat. Acad. Sci. U.S.A. 104, 8438-8443), also displayed sensitivity to (R)-9bMS treatment (FIG. 9).

Taken together, these data indicate that CRPCs exploit the epigenetic activity of ACK1 tyrosine kinase to establish a transcriptionally permissive chromatin landscape, rich in dual, H4-pY88/H3K4me3 marks to promote AR transcriptional autoregulation. Overall, uncovering the novel epigenetic control of AR opens a new avenue for the treatment of CRPCs using ACK1 inhibitor.

ACK1 Inhibitor (R)-9bMS as an Immunomodulatory Inhibitor

Figure 12:
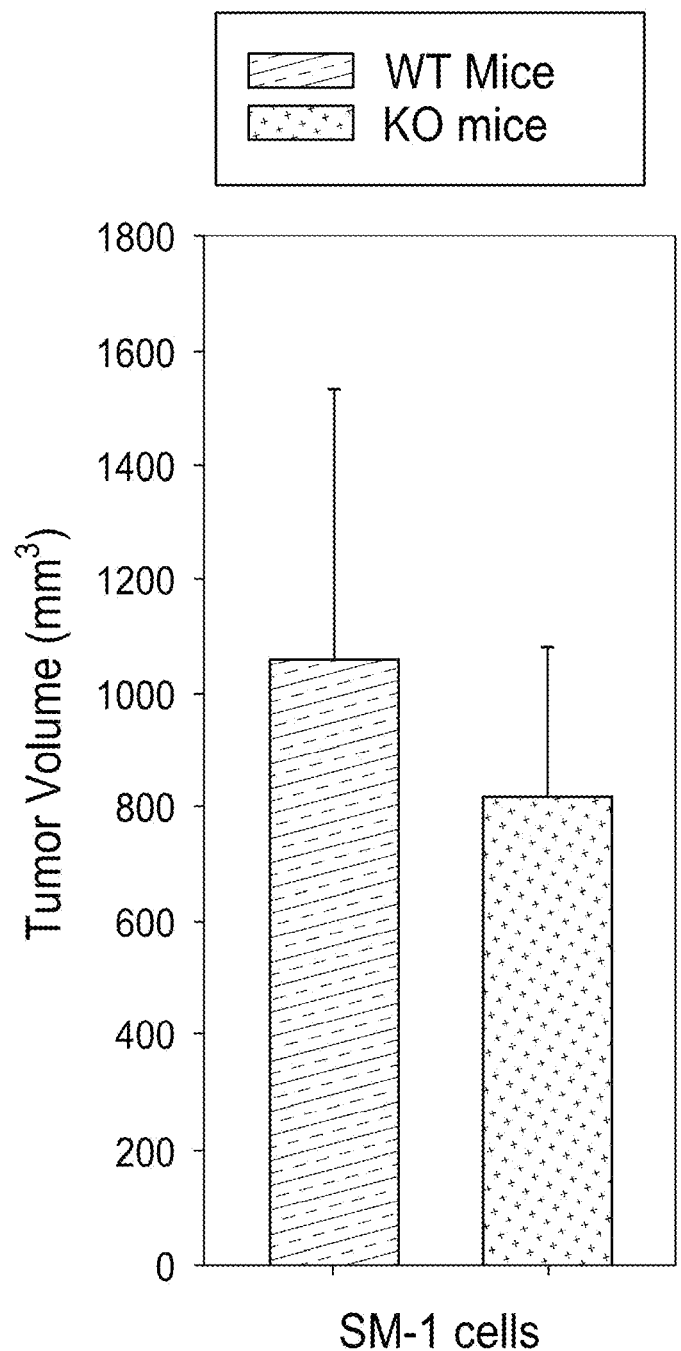
FIG. 12. ACK1 inhibitor causes tumor suppression by activating immune cells anti-tumor response. SM-1 cells were injected in WT and KO mice subcutaneously and formation of xenograft tumors was monitored over next 4-5 weeks. Tumors volumes were measures (n=7, each case) and mean tumor volumes are shown.

To understand role of ACK1 kinase in regulating immune function, ACK1 knockout mice (KO) was generated. These mice were assessed for the effect of loss of ACK1 kinase activity. ACK1 knockdown causes significant increase in CD4 helper, CD8 cytotoxic and natural killer (NK) cells (FIGS. 10A-10F and 11A-11C). Further, a significant increase in MDSC (myloid-derived suppressor cells) was also observed (FIGS. 10A-10F and 11A-11C). Further, WT and ACK1 KO mice were injected with SM-1 cancer cells and tumor growth was monitored. The tumors developed in KO mice tumors were significantly smaller than WT (FIG. 12). Taken together, these data demonstrate that ACK1 kinase activity is critical for cancer cells to keep immune cells 'quiescent'. Thus treatment with ACK1 inhibitor causes tumor suppression by activating immune cells anti-tumor response.

What is claimed is:

1. A compound having Formula III:

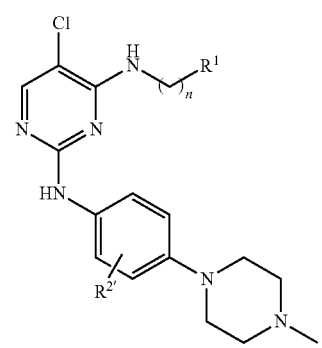

III wherein n is 1, 2, or 3;

and $R^1$ is cyclopentyl, cyclohexyl, furanyl, pyrrolidinyl, oxanyl, phenyl, or pyrimidinyl, any of which are unsubstituted or substituted with Cl, Br, F, $C_1$-$C_6$ alkyl, or $C_1$-$C_6$ alkoxyl;

$R^{2'}$ is H, Cl, Br, F, $C_1$-$C_6$ alkyl, $C_1$-$C_6$ alkoxyl;

or a pharmaceutically acceptable salt thereof.

2. The compound of claim 1, wherein $R^1$ is cyclopentyl, cyclohexyl, furanyl, pyrrolidinyl, oxane, any of which is optionally substituted with $C_1$-$C_6$ alkyl.

3. The compound of claim 1, wherein $R^1$ is phenyl optionally substituted with Cl or F.

4. The compound of claim 1, wherein $R^{2'}$ is H or OMe.

5. A compound chosen from

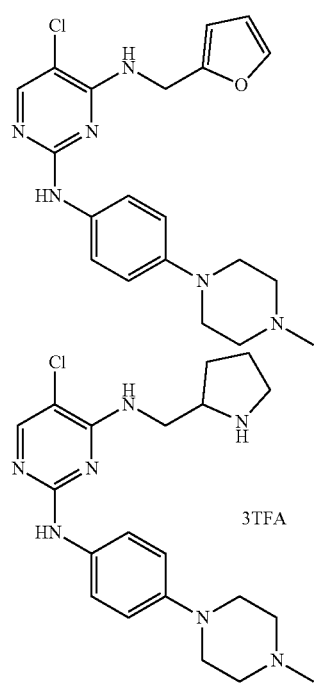

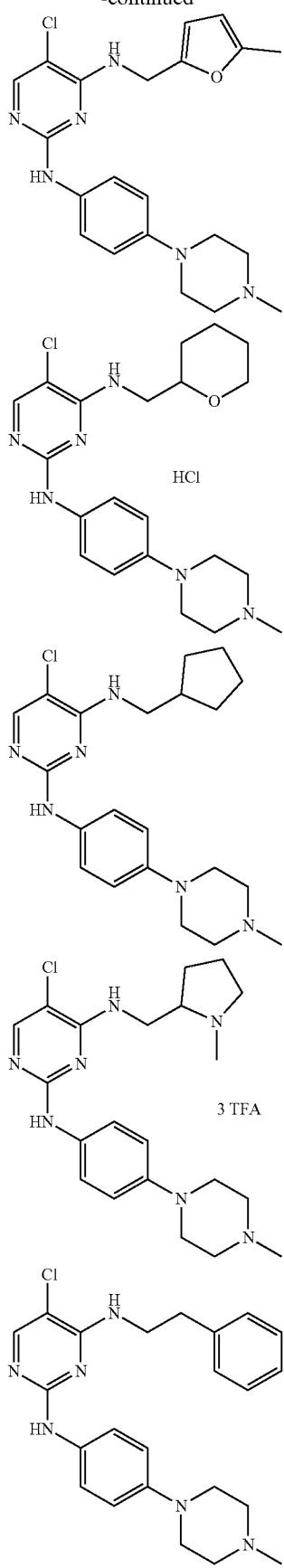

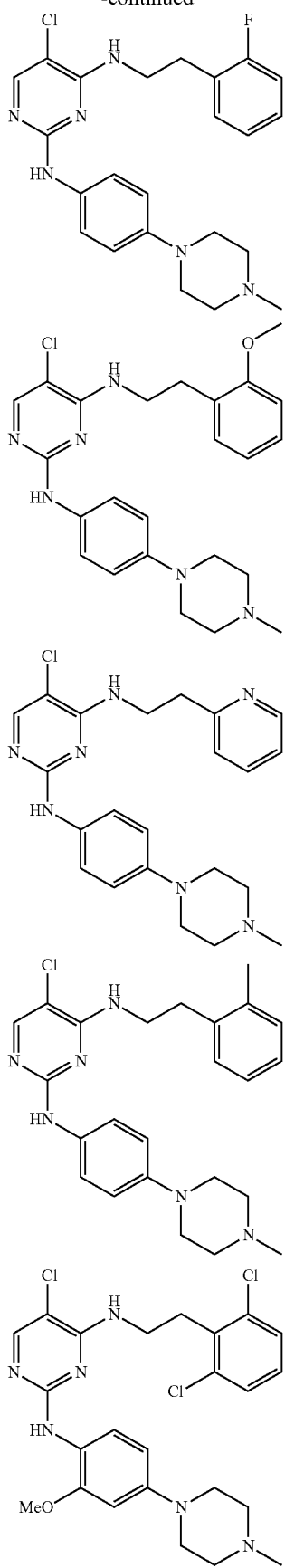
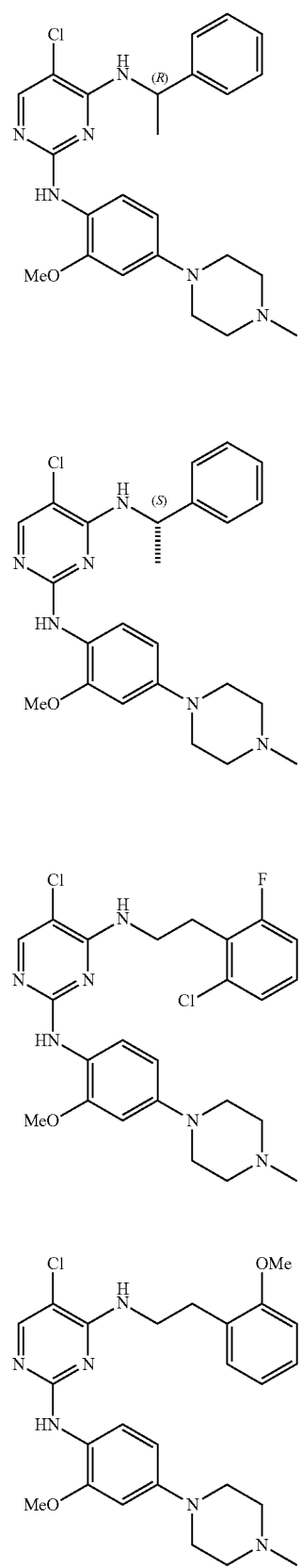

-continued

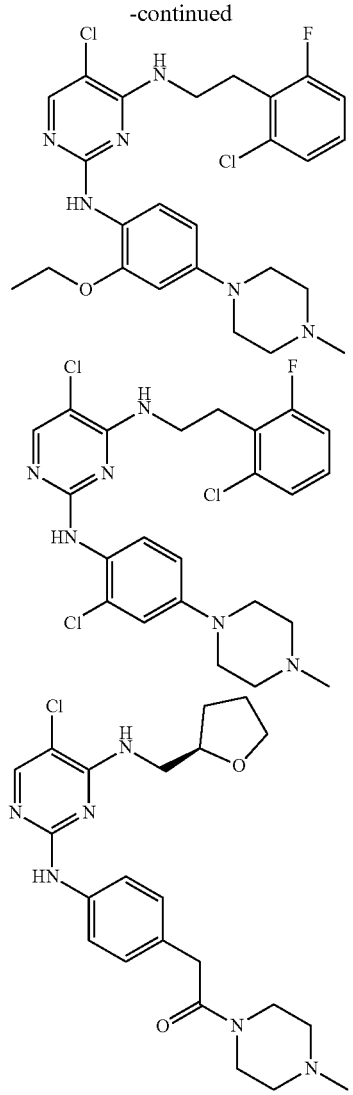

-continued

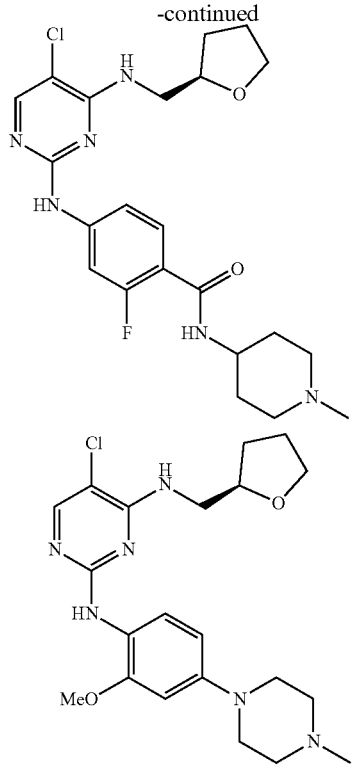

and

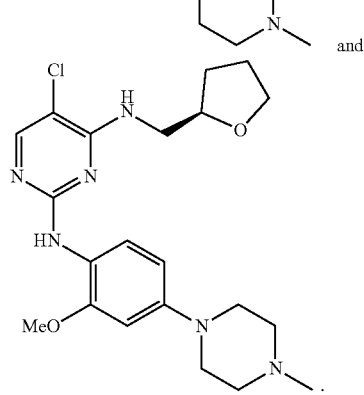

.

6. A method of treating prostate cancer in a subject, comprising administering to the subject an effective amount of a compound of claim 1.

7. A method comprising contacting a prostate tumor cell with an effective amount of a compound of claim 1.

8. A method of treating prostate cancer in a subject, comprising administering to the subject an effective amount of a compound of claim 5.

9. A method comprising contacting a prostate tumor cell with an effective amount of a compound of claim 5.

* * * * *